(12) United States Patent
Firooznia et al.

(10) Patent No.: US 8,691,993 B2
(45) Date of Patent: Apr. 8, 2014

(54) PIPERIDINYL NAPHTHYLACETIC ACIDS

(71) Applicant: Hoffman-La Roche Inc., Nutley, NJ (US)

(72) Inventors: Fariborz Firooznia, Florham Park, NJ (US); Tai-An Lin, Pequannock, NJ (US); Eric Mertz, Fair Lawn, NJ (US); Achyutharao Sidduri, West Orange, NJ (US); Sung-Sau So, Verona, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/706,497

(22) Filed: Dec. 6, 2012

(65) Prior Publication Data
US 2013/0150407 A1   Jun. 13, 2013

Related U.S. Application Data

(60) Provisional application No. 61/569,313, filed on Dec. 12, 2011.

(51) Int. Cl.
| C07D 211/00 | (2006.01) |
| C07D 295/00 | (2006.01) |
| C07D 211/06 | (2006.01) |
| A61K 31/445 | (2006.01) |

(52) U.S. Cl.
USPC ........... 546/194; 546/184; 546/205; 514/318; 514/319

(58) Field of Classification Search
None
See application file for complete search history.

(56) References Cited

FOREIGN PATENT DOCUMENTS

| WO | 2010/055006 | 5/2010 |
| WO | WO 2010/055006 A1 * | 5/2010 |

OTHER PUBLICATIONS

The Internation Search Report and Written Opinion, issued on Apr. 12, 2013, in the corresponding PCT Patent Application No. PCT/EP2012/074882., pp. 9.

* cited by examiner

*Primary Examiner* — Rita Desai
*Assistant Examiner* — Ben S Michelson

(57) ABSTRACT

The invention is concerned with the compounds of formula (I):

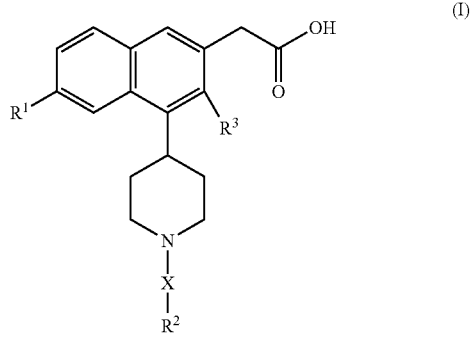

and pharmaceutically acceptable salts thereof, wherein $R^1$, $R^2$, $R^3$ and X are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

17 Claims, No Drawings

PIPERIDINYL NAPHTHYLACETIC ACIDS

PRIORITY TO RELATED APPLICATION(S)

This application claims the benefit of U.S. Provisional Application No. 61/569,313, filed Dec. 12, 2011. The entire contents of the above-identified applications are hereby incorporated by reference.

RELATED APPLICATIONS

This application is related to U.S. application Ser. No. 12/614,485, filed Nov. 9, 2009; Ser. No. 12/614,478, filed Nov. 9, 2009; and Ser. No. 12/614,497, filed Nov. 9, 2009. The entire contents of these applications are expressly incorporated by reference herein.

BACKGROUND OF THE INVENTION

The present invention relates to novel substituted naphthalene-2-yl acetic acids, their manufacture, pharmaceutical compositions containing them and their use as CRTH2 antagonists, partial agonists, inverse agonists or partial inverse agonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type 2 cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Allergy* 34:1283-1290). Sequence variants of the gene encoding CRTH2, which differentially influence its mRNA stability, are shown to be associated with asthma (Huang et al., *Hum Mol Genet*. 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention provides for a compound of formula (I):

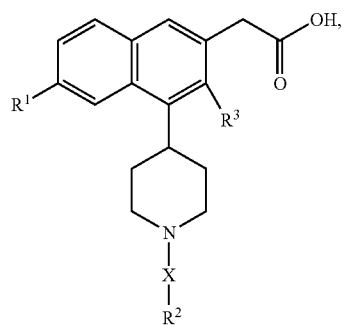

(I)

wherein:
X is $-SO_2-$ or $-C(O)-$;
$R^1$ is halogen;
$R^2$ is
  phenyl, unsubstituted or mono- or bi-substituted independently with lower alkyl, halogen, alkoxy, $-SO_2$-lower alkyl or haloalkyl,
  unsubstituted heteroaryl,
  lower alkyl, unsubstituted or substituted with unsubstituted phenyl or phenyl substituted with halogen, $NO_2$ or $NH_2$,
  unsubstituted cycloalkyl,
  unsubstituted heterocycloalkyl, or
  NH-phenyl, said phenyl being unsubstituted or substituted with halogen, lower alkyl, haloalkyl, $-SO_2$-lower alkyl or alkoxy; and
$R^3$ is lower alkyl or hydrogen,
or a pharmaceutically acceptable salt thereof.

The invention also provides for pharmaceutical compositions comprising the compounds, methods of using the compounds and methods of preparing the compounds.

All documents cited to or relied upon below are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^3$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

The term "alkoxy" denotes a group of the formula $-O-R'$, wherein R' is an alkyl group. Examples of alkoxy moieties include methoxy, ethoxy, isopropoxy, and tert-butoxy.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl.

The terms "halo", "halogen" and "halide", which may be used interchangeably, refer to a substituent fluoro, chloro, bromo, or iodo.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl.

"Cycloalkyl" means a monovalent saturated carbocyclic moiety having mono- or bicyclic rings. The cycloalkyl moiety can optionally be substituted with one or more substituents. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

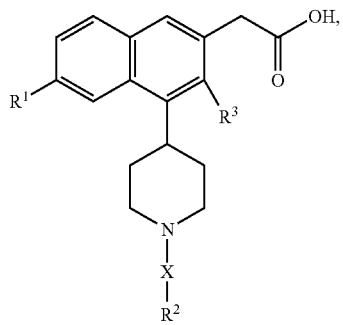

wherein:
X is —SO$_2$— or —C(O)—;
R$^1$ is halogen;
R$^2$ is
　phenyl, unsubstituted or mono- or bi-substituted independently with lower alkyl, halogen, alkoxy, —SO$_2$-lower alkyl or haloalkyl,
　unsubstituted heteroaryl,
　lower alkyl, unsubstituted or substituted with unsubstituted phenyl or phenyl substituted with halogen, NO$_2$ or NH$_2$,
　unsubstituted cycloalkyl,
　unsubstituted heterocycloalkyl, or
　NH-phenyl, said phenyl being unsubstituted or substituted with halogen, lower alkyl, haloalkyl, —SO$_2$-lower alkyl or alkoxy; and
R$^3$ is lower alkyl or hydrogen,
or a pharmaceutically acceptable salt thereof.

In another embodiment, provided is a compound of formula (I), wherein X is —SO$_2$—.

In another embodiment, provided is a compound of formula (I), wherein X is —C(O)—.

In another embodiment, provided is a compound of formula (I), wherein R$^1$ is fluorine.

In another embodiment, provided is a compound of formula (I), wherein X is —SO$_2$— and R$^2$ is phenyl, unsubstituted or mono- or bi-substituted independently with lower alkyl, halogen, alkoxy, —SO$_2$-lower alkyl or —CF$_3$; unsubstituted heteroaryl; or lower alkyl, unsubstituted or substituted with unsubstituted phenyl or phenyl substituted with halogen, NO$_2$ or NH$_2$.

In another embodiment, provided is a compound of formula (I), wherein X is —SO$_2$— and R$^2$ is unsubstituted cycloalkyl; unsubstituted heterocycloalkyl; or NH-phenyl, said phenyl being unsubstituted or substituted with halogen, lower alkyl, haloalkyl, —SO$_2$-lower alkyl or alkoxy.

In another embodiment, provided is a compound of formula (I), wherein R$^2$ is phenyl, methylphenyl, chlorophenyl, methanesulfonylphenyl, dichlorophenyl, difluorophenyl, trifluoromethylphenyl, bis-trifluoromethylphenyl, methoxyphenyl, nitrophenyl or aminophenyl.

In another embodiment, provided is a compound of formula (I), wherein R$^2$ is pyridinyl.

In another embodiment, provided is a compound of formula (I), wherein R$^2$ is methyl or methyl substituted with phenyl, chlorophenyl, nitrophenyl or aminophenyl.

In another embodiment, provided is a compound of formula (I), wherein R$^2$ is cyclopentyl.

In another embodiment, provided is a compound of formula (I), wherein R$^2$ is pyrrolidinyl.

In another embodiment, provided is a compound of formula (I), wherein R$^2$ is —NH-difluorophenyl, —NH-dichlorophenyl, —NH-chlorophenyl, —NH-phenylmethoxy or —NH-trifluoromethylphenyl.

In another embodiment, provided is a compound of formula (I), wherein R³ is methyl.

In another embodiment, provided is a compound of formula (I), wherein R³ is hydrogen.

In another embodiment, provided is a compound of formula (I), wherein the compound is:

[4-(1-Benzenesulfonyl-piperidin-4-yl)-6-fluoro-naphthalen-2-yl]-acetic acid;
{6-Fluoro-4-[1-(toluene-4-sulfonyl)-piperidin-4-yl]-naphthalen-2-yl}-acetic acid;
{6-Fluoro-4-[1-(pyridine-2-sulfonyl)-piperidin-4-yl]-naphthalen-2-yl}-acetic acid;
{6-Fluoro-4-[1-(pyridine-3-sulfonyl)-piperidin-4-yl]-naphthalen-2-yl}-acetic acid;
{6-Fluoro-4-[1-(pyridine-4-sulfonyl)-piperidin-4-yl]-naphthalen-2-yl}-acetic acid;
{4-[1-(2-Chloro-benzenesulfonyl)-piperidin-4-yl]-6-fluoro-naphthalen-2-yl}-acetic acid;
{4-[1-(3-Chloro-benzenesulfonyl)-piperidin-4-yl]-6-fluoro-naphthalen-2-yl}-acetic acid;
{4-[1-(4-Chloro-benzenesulfonyl)-piperidin-4-yl]-6-fluoro-naphthalen-2-yl}-acetic acid;
{6-Fluoro-4-[1-(3-methanesulfonyl-benzenesulfonyl)-piperidin-4-yl]-naphthalen-2-yl}-acetic acid;
{4-[1-(2,5-Dichloro-benzenesulfonyl)-piperidin-4-yl]-6-fluoro-naphthalen-2-yl}-acetic acid;
{4-[1-(2,4-Dichloro-benzenesulfonyl)-piperidin-4-yl]-6-fluoro-naphthalen-2-yl}-acetic acid;
{4-[1-(3,5-Dichloro-benzenesulfonyl)-piperidin-4-yl]-6-fluoro-naphthalen-2-yl}-acetic acid;
{4-[1-(3,5-Bis-trifluoromethyl-benzenesulfonyl)-piperidin-4-yl]-6-fluoro-naphthalen-2-yl}-acetic acid;
{4-[1-(2-Chloro-benzenesulfonyl)-piperidin-4-yl]-6-fluoro-3-methyl-naphthalen-2-yl}-acetic acid;
[6-Fluoro-4-(1-methanesulfonyl-piperidin-4-yl)-3-methyl-naphthalen-2-yl]-acetic acid;
{4-[1-(2,4-Dichloro-benzenesulfonyl)-piperidin-4-yl]-6-fluoro-3-methyl-naphthalen-2-yl}-acetic acid;
{4-[1-(2,5-Dichloro-benzenesulfonyl)-piperidin-4-yl]-6-fluoro-3-methyl-naphthalen-2-yl}-acetic acid;
{4-[1-(2,6-Dichloro-benzenesulfonyl)-piperidin-4-yl]-6-fluoro-3-methyl-naphthalen-2-yl}-acetic acid;
[6-Fluoro-3-methyl-4-(1-phenylmethanesulfonyl-piperidin-4-yl)-naphthalen-2-yl]-acetic acid;
{6-Fluoro-4-[1-(2-methoxy-benzenesulfonyl)-piperidin-4-yl]-3-methyl-naphthalen-2-yl}-acetic acid;
{4-[1-(3-Chloro-phenylmethanesulfonyl)-piperidin-4-yl]-6-fluoro-3-methyl-naphthalen-2-yl}-acetic acid;
{4-[1-(4-Chloro-phenylmethanesulfonyl)-piperidin-4-yl]-6-fluoro-3-methyl-naphthalen-2-yl}-acetic acid;
{6-Fluoro-3-methyl-4-[1-(3-trifluoromethyl-benzenesulfonyl)-piperidin-4-yl-naphthalen-2-yl}-acetic acid;
[4-(1-Cyclopentanesulfonyl-piperidin-4-yl)-6-fluoro-3-methyl-naphthalen-2-yl]-acetic acid;
{6-Fluoro-3-methyl-4-[1-(pyrrolidine-1-sulfonyl)-piperidin-4-yl]-naphthalen-2-yl}-acetic acid;
{6-Fluoro-3-methyl-4-[1-(2-nitro-phenylmethanesulfonyl)-piperidin-4-yl]-naphthalen-2-yl}-acetic acid;
{4-[1-(2-Amino-phenylmethanesulfonyl)-piperidin-4-yl]-6-fluoro-3-methyl-naphthalen-2-yl}-acetic acid;
{4-[1-(2,4-Dichloro-benzoyl)-piperidin-4-yl]-6-fluoro-3-methyl-naphthalen-2-yl}-acetic acid;
{4-[1-(2,6-Dichloro-benzoyl)-piperidin-4-yl]-6-fluoro-3-methyl-naphthalen-2-yl}-acetic acid;
{4-[1-(2,5-Difluoro-benzoyl)-piperidin-4-yl]-6-fluoro-3-methyl-naphthalen-2-yl}-acetic acid;
[6-Fluoro-3-methyl-4-(1-phenylacetyl-piperidin-4-yl)-naphthalen-2-yl]-acetic acid;
{4-[1-(2,6-Difluoro-phenylcarbamoyl)-piperidin-4-yl]-6-fluoro-3-methyl-naphthalen-2-yl}-acetic acid;
{4-[1-(2,4-Dichloro-phenylcarbamoyl)-piperidin-4-yl]-6-fluoro-3-methyl-naphthalen-2-yl}-acetic acid;
{4-[1-(2-Chloro-phenylcarbamoyl)-piperidin-4-yl]-6-fluoro-3-methyl-naphthalen-2-yl}-acetic acid;
{6-Fluoro-4-[1-(2-methoxy-phenylcarbamoyl)-piperidin-4-yl]-3-methyl-naphthalen-2-yl}-acetic acid; or
{6-Fluoro-3-methyl-4-[1-(3-trifluoromethyl-phenylcarbamoyl)-piperidin-4-yl-naphthalen-2-yl}-acetic acid.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

In another embodiment, the invention provides for the use of a compound according to formula (I) for the preparation of a medicament for the treatment or prophylaxis of a respiratory disorder.

In another embodiment, the invention provides for a compound according to formula (I) for the treatment or prophylaxis of a respiratory disorder.

In another embodiment, the invention provides for a method for treating a respiratory disorder selected from chronic obstructive pulmonary disorder (COPD), asthma, and bronchospasm, comprising the step of administering a therapeutically effective amount of a compound according to formula (I) to a subject in need thereof.

In another embodiment, provided is an invention as hereinbefore described.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

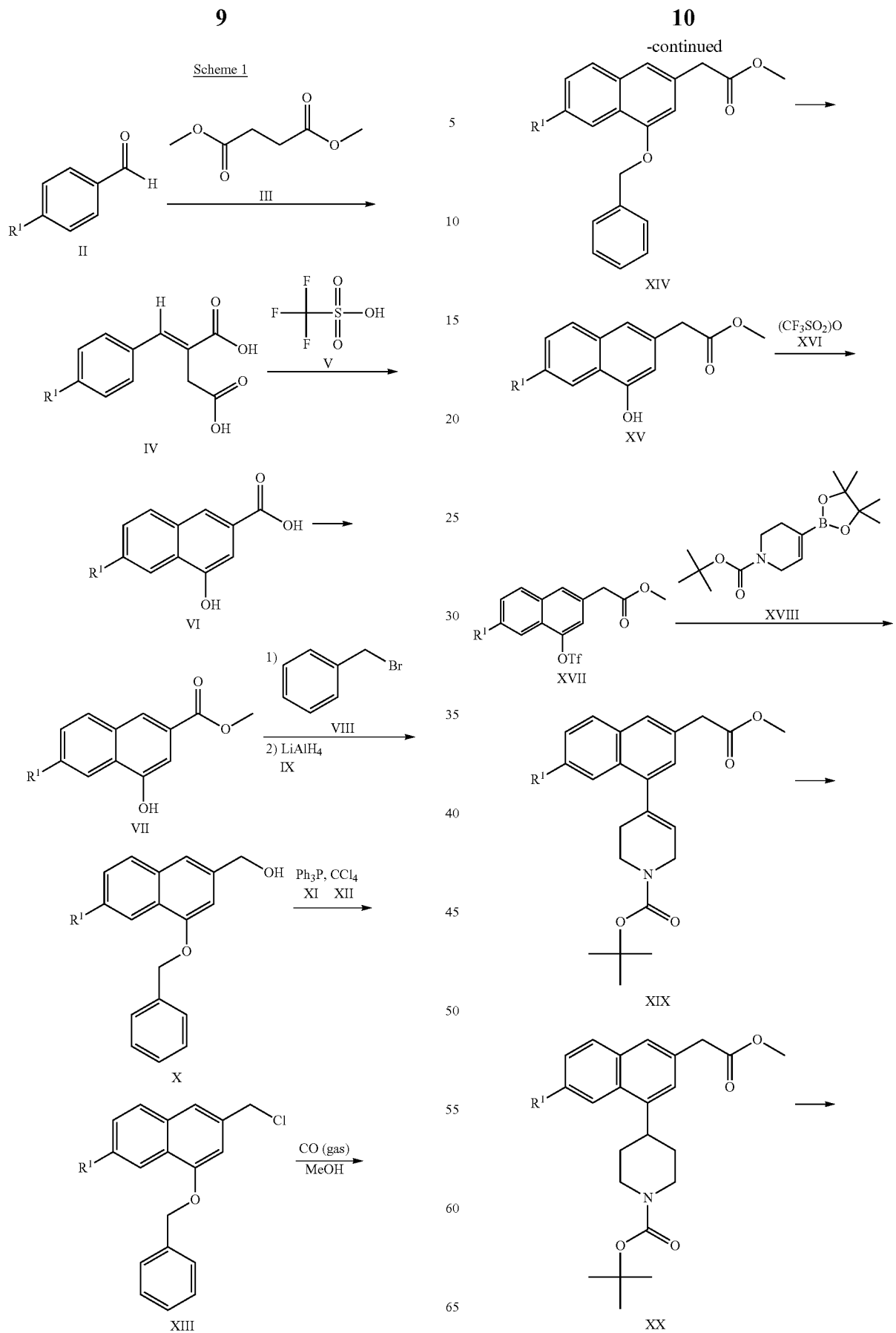

Compounds of the invention of formula XXIV can be prepared according to Scheme 1. In this process, a Stobbe condensation reaction between the substituted benzaldehydes II and dimethyl succinate (III) followed by hydrolysis gives the unsaturated di-acids IV, which subsequently undergo cyclization to produce compounds VI. The naphthalene derivatives VI are then converted to the corresponding methyl esters VII. The reaction of VII with benzyl bromide (VIII), followed by reduction using lithium aluminum hydride (IX), affords the alcohols X. Compounds X are then converted to the corresponding chloro intermediates XIII by treatment with carbon tetrachloride (XI) and triphenylphosphine (XII). Conversion of the chlorides XIII to the methyl esters XIV can be accomplished by a palladium-catalyzed carbonylation reaction in methanol. Hydrogenolysis of compounds XIV affords phenols XV, which undergo reaction with trifluoromethanesulfonic anhydride (XVI) to give the corresponding triflates XVII. Compounds of formula XVII undergo a palladium-catalyzed coupling with the vinylboronate XVIII to give the coupling products XIX. Hydrogenation of the double bond in XIX to give the piperidines XX is followed by cleavage of the tert-butyl carbamate to give the secondary amines XXI. Sulfonylation with arylsulfonyl chlorides of formula XXII gives the sulfonamides XXIII. Hydrolysis of the methyl ester gives the compounds of the invention of formula XXIV.

In the first step outlined in Scheme 1, the unsaturated di-acids IV can be prepared by a Stobbe condensation reaction between the para-substituted benzaldehydes II and dimethyl succinate (III). The reaction can be carried out in the presence of a base such as sodium methoxide, lithium methoxide, sodium tert-butoxide, sodium hydride or potassium tert-butoxide, in an organic solvent such as methanol, tert-butanol, toluene, or mixtures thereof, at a temperature between room temperature and 90° C. for several hours (reference: Dian, Y. L. et al., *Tetrahedron Lett.*, 32 (1991) 5255).

Cyclization of the dicarboxylic acids IV to form 4-hydroxy-naphthalene carboxylic acids VI can be accomplished in neat trifluoromethanesulfonic acid (V) at room temperature over several hours (Hong, W. P.; Lim, H. N.; Park, H. W.; Lee, K.-J. *Bull. Korean Chem. Soc.* 26 (2005) 655).

Intermediates VI can be readily converted to the 4-hydroxy-naphthalene carboxylic acid ester intermediates VII in the presence of a catalytic amount of concentrated sulfuric acid and methanol at temperatures between room temperature and 80° C. (or the reflux temperature) for several hours. Alternatively, the esterification reaction can be carried out in the presence of thionyl chloride and methanol at temperatures between 65° C. and 80° C. (or the reflux temperature) for several hours.

Treatment of the hydroxyl compounds VII with benzyl bromide (VIII) affords the corresponding benzyl ethers. The reaction can be carried out in the presence of a base such as potassium carbonate, or cesium carbonate, in an inert organic solvent such as acetone, acetonitrile, or N,N-dimethylformamide at a temperature between room temperature and 60° C. for several hours.

Reduction of the above benzyl ethers with lithium aluminum hydride (IX) affords the alcohols X. The reaction can be carried out in an inert organic solvent such as tetrahydrofuran, diethyl ether, toluene, or mixtures thereof, at a temperature between room temperature and 80° C. for several hours (reference: Chan W. K, et al., *J. Med. Chem.* 39 (1996) 3756-3768).

The chloride intermediates XIII can be prepared by the treatment of the alcohols X with carbon tetrachloride (XII) and triphenylphosphine (XI) in an inert organic solvent such as toluene, acetonitrile, dichloromethane, N,N-dimethylformamide, or tetrahydrofuran, at a temperature between 0 and 120° C. for several hours (reference: Kozhinov, D. V. et al., *J. Org. Chem.* 69 (2004) 1378-1379).

Conversion of the intermediates XIII to the methyl esters XIV can be accomplished by a palladium-catalyzed carbonylation reaction under an atmosphere of carbon monoxide in methanol. The reaction can be carried out in the presence of a palladium catalyst such as bis(triphenylphosphine)dichloropalladium(II) ($Pd(PPh_3)_2Cl_2$ at a temperature between room temperature and 90° C. for 10 minutes to several hours (reference: Kozhinov, D. V. et al., *J. Org. Chem.* 69 (2004) 1378-1379).

Hydrogenolysis of benzyl ethers XIV affords the intermediates XV. The reaction can be carried out in the presence of 10% palladium on carbon under an atmospheric pressure (of about 1 atm) of hydrogen, in an organic solvent such as ethyl acetate, methanol, or ethanol, at room temperature for several hours.

The hydroxyl compounds XV can be converted to the triflates XVII by treatment with trifluoromethanesulfonic anhydride (XVI). The reaction can be carried out in the presence of a base such as pyridine, triethylamine, diisopropylethylamine, N,N-dimethyl-4-pyridinamine, 2,6-dimethylpyridine, 2,4,6-trimethylpyridine, sodium hydride, or potassium carbonate, in a suitable solvent such as dichloromethane, chloroform or acetonitrile, at a temperature between −78° C. and room temperature for 30 minutes to several hours (reference: Chan W. K. et al., *J. Med. Chem.* 39 (1996) 3756-3768).

The triflates of formula XVII may be converted to the tetrahydropyridine derivatives of formula XIV by carrying out a palladium-catalyzed coupling with the vinylboronate of formula XVIII. The reaction is carried out in the presence of a base such as sodium carbonate or potassium acetate or potassium carbonate in the presence of a palladium catalyst such as tetrakis(triphenylphosphine)pallad-ium(0) or [1,1'-bis(diphenylphosphino)ferrocene]dichloropalladium(II). The reaction is conveniently carried out in a solvent such as N,N-dimethylformamide or a mixture of N,N-dimethylformamide and a second solvent such as methanol, at a temperature between about 60° C. and about 100° C. for several hours (reference: Marsilje, T. H. III et al., U.S. application Ser. No. 13/000,999).

Hydrogenation of tetrahydropyridines XIX affords the intermediates XX. The reaction can be carried out in the presence of 10% palladium on carbon under an atmospheric pressure (of about 1 atm) of hydrogen, in an organic solvent such as ethyl acetate, methanol, or ethanol, at room temperature for several hours.

Removal of the tert-butylcarbamate protective group in the compounds of formula XX to give secondary amines of formula XXI can be carried out by treating the compound of formula XX with trifluoroacetic acid in an inert solvent such as dichloromethane at about room temperature for several hours.

Sulfonamides XXIII are conveniently prepared by treating amines XXI with arylsulfonyl chlorides XXIII in the presence of a base such as triethylamine or diisopropylethylamine in an inert solvent such as dichloromethane or tetrahydrofuran at about room temperature for several hours.

The methyl ester in sulfonamides XXIII can be removed to give the compounds of the invention of formula XXIV by treating the esters with an alkali metal hydroxide such as sodium hydroxide or lithium hydroxide in the presence of water and an organic co-solvent such as tetrahydrofuran or a mixture of tetrahydrofuran and methanol, at about room temperature for several hours.

Scheme 2

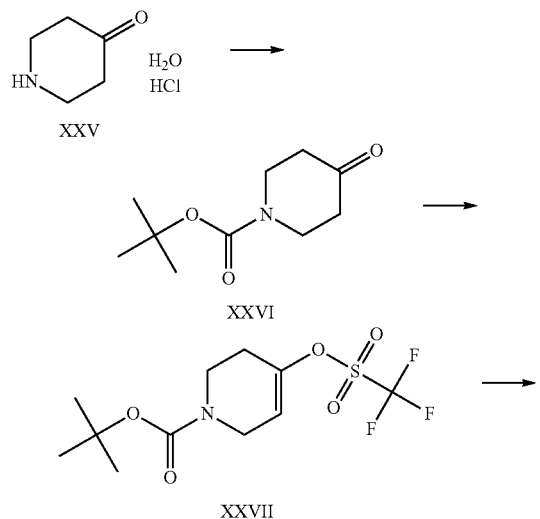

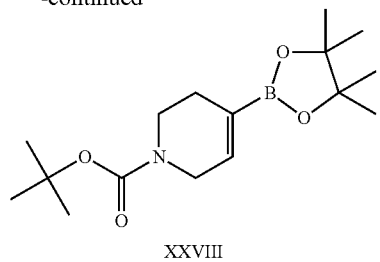

XXVIII

The compound of formula XXVIII may be prepared using any conventional means. One route is shown in Scheme 2. According to this process, 4-piperidone hydrate hydrochloride (XXV) is converted to the tert-butyl carbamate (XXVI), which undergoes triflation to give the vinyl triflate XXVII. A palladium-catalyzed coupling with bis(pinacolato)diboron then gives the vinyl boronate (XXVIII).

The conversion of piperidone XXV to tert-butyl carbamate XXVI may be conveniently carried out by treating XXV with di-tert-butyl dicarbonate in a mixture of water and dioxane in the presence of an inorganic base such as sodium carbonate or sodium bicarbonate at a temperature between about room temperature and about 70° C. for several hours.

Ketone XXVI is conveniently converted to the vinyl triflate XXVII by treating it with a strong base such as lithium diisopropylamide (which may be prepared in situ from the reaction of diisopropylamine with n-butyllithium) and then treating the resulting enolate with a triflating reagent such as N-phenyltriflimide. The reaction is initiated at a temperature of about −78° C. and then continued at room temperature for several hours. Tetrahydrofuran is a convenient solvent (reference: Kettle, J. G. U.S. application Ser. No. 12/094,365).

Vinyl triflate XXVII may be converted to the vinyl boronate of formula XXVIII by treating it with bis(pinacolato) diboron in the presence of a base such as potassium acetate, a palladium catalyst such as [1,1'-bis(diphenylphosphino)-ferrocene]dichloropalladium(II) or its complex with dichloromethane, and in the optional additional presence of a ligand such as bis(diphenylphosphino)-ferrocene. Dioxane is a convenient solvent, and the reaction is conveniently carried out at about 80-90° C. for several hours.

Compounds of the invention of formula XXXV (where $R^1$ is defined in the same manner as defined above for the genus of formula I and $R^4$ is phenyl, substituted phenyl, heteroaryl, lower alkyl, substituted lower alkyl, cycloalkyl, or heterocycloalkyl) can be prepared according to Scheme 3 below. In this process, the reaction of 4-iodo-piperidine-1-carboxylic acid tert-butyl ester XXIX with activated zinc gives a piperidin-4-yl zinc reagent which is immediately reacted with the triflate intermediate XXX to give the naphthalene derivatives XXXI. Cleavage of the tert-butyl carbamate in XXXI to give the secondary amines XXXII is followed by sulfonylation with sulfonyl chlorides of formula XXXIII (where $R^4$ is phenyl, substituted phenyl, heteroaryl, lower alkyl, substituted lower alkyl, cycloalkyl, or heterocycloalkyl) to give the sulfonamides XXXIV. Hydrolysis of the methyl ester gives the compounds of the invention of formula XXXV.

Scheme 3

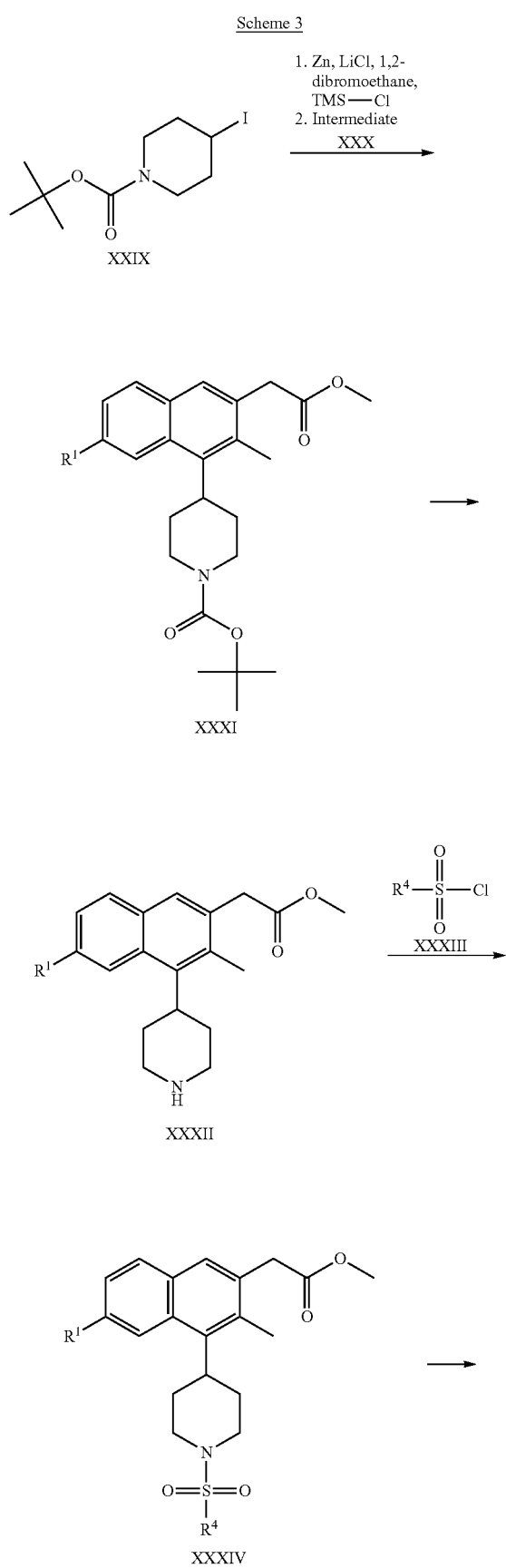

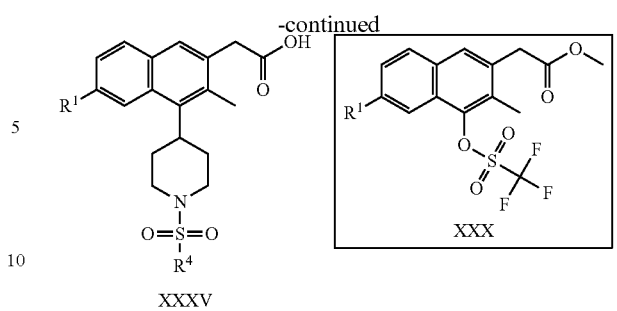

In the first step outlined in Scheme 3, the reaction of 4-iodo-piperidine-1-carboxylic acid tert-butyl ester XXIX with activated zinc dust and lithium chloride can occur in the presence of 1,2-dibromoethane and chlorotrimethylsilane. The reaction may be carried out in an inert solvent such as tetrahydrofuran at temperatures between 50° C. and 60° C. for approximately 1.5 hours. The piperidin-4-yl zinc reagent thus formed can then react with the triflate intermediate XXX in the presence of a palladium source such as palladium(II) acetate and a phosphine ligand such as 2-dicyclohexylphosphino-2',6'-dimethoxybiphenyl (S-Phos) at temperatures between 60° C. and 70° C. for approximately 15 hours.

Deprotection of the tert-butyl carbamate in XXXI to give the secondary amines XXXII can occur in the presence of an excess of trifluoroacetic acid in a convenient solvent such as dichloromethane at room temperature for several hours.

The reaction of the amines XXXII with sulfonyl chlorides XXXIII to generate the methyl ester intermediates XXXIV can occur in the presence of a base such as triethylamine or N,N-diisopropylethylamine and an inert solvent such as dichloromethane or tetrahydrofuran. The reaction can proceed at temperatures between 0° C. and room temperature for reaction times between 2 hours and 15 hours.

Hydrolysis of the methyl ester in XXXIV to afford the compounds of the invention of formula XXXV can occur in the presence of a base such as lithium hydroxide in mixtures of water and tetrahydrofuran at temperatures between room temperature and the reflux temperature for several hours.

Compounds of the invention of formula XXXVIII (where $R^1$ is defined in the same manner as defined above for the genus of formula I and $R^5$ is phenyl, substituted phenyl, lower alkyl, or substituted lower alkyl) can be prepared according to Scheme 4 below. In this process, the reaction of 2-(6-halo-3-methyl-4-(piperidin-4-yl)naphthalen-2-yl)acetic acid methyl ester (XXXII) with acid chlorides XXXVI (where $R^5$ is phenyl, substituted phenyl, lower alkyl, or substituted lower alkyl) gives the amide derivatives XXXVII. Hydrolysis of the methyl ester gives the compounds of the invention of formula XXXVIII.

Scheme 4

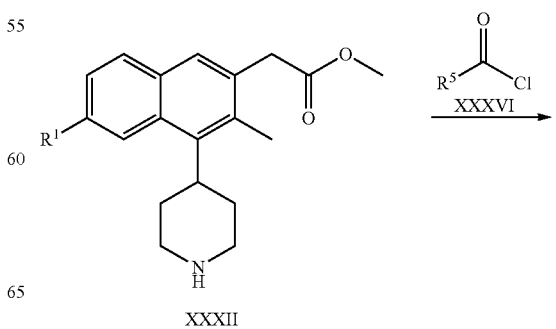

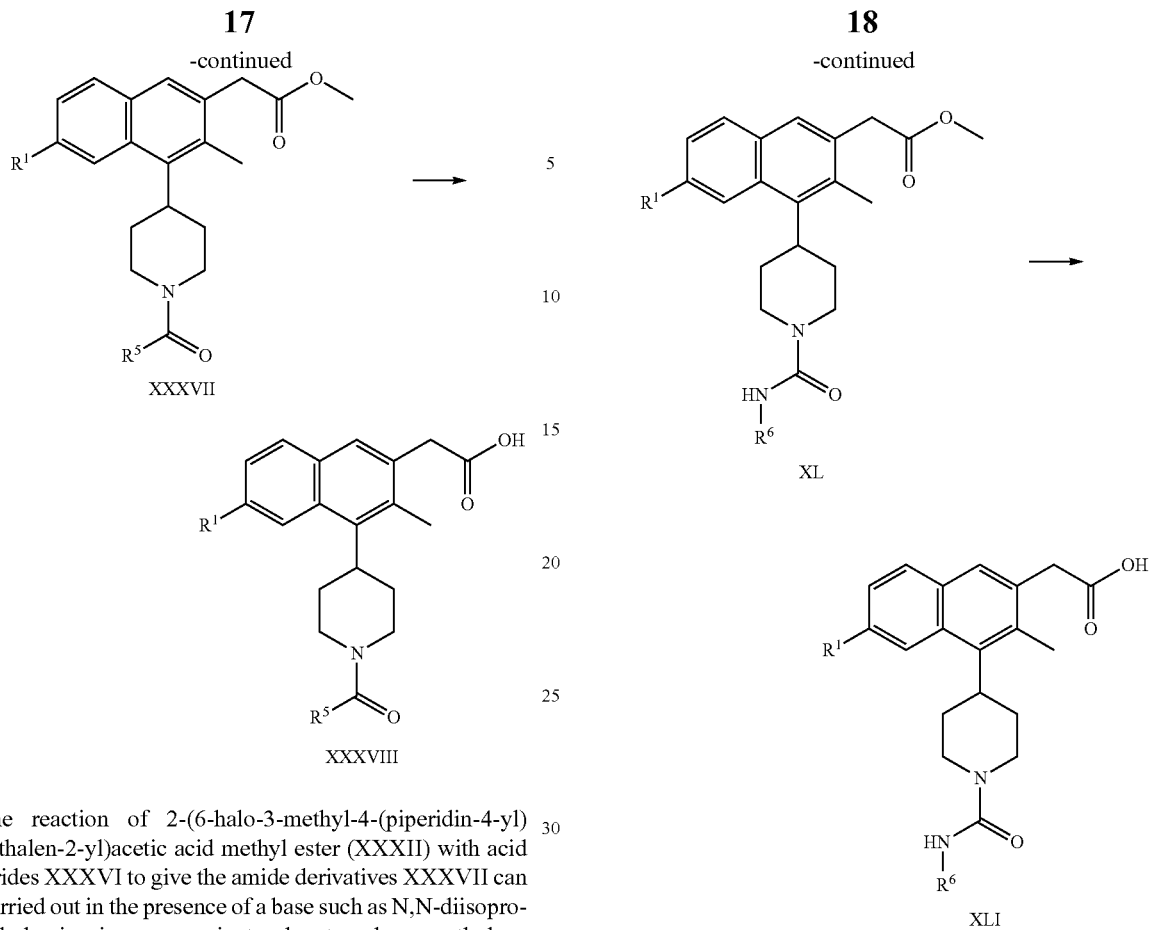

The reaction of 2-(6-halo-3-methyl-4-(piperidin-4-yl) naphthalen-2-yl)acetic acid methyl ester (XXXII) with acid chlorides XXXVI to give the amide derivatives XXXVII can be carried out in the presence of a base such as N,N-diisopropylethylamine in a convenient solvent such as methylene chloride for several hours at room temperature.

Hydrolysis of the methyl ester in XXXVII to afford compounds of interest of formula XXXVIII can occur in the presence of a base such as lithium hydroxide in mixtures of water and tetrahydrofuran at temperatures between room temperature and the reflux temperature for several hours.

Compounds of the invention of formula XLI (where $R^1$ is defined in the same manner as defined above for the genus of formula I and $R^6$ is phenyl or substituted phenyl) can be prepared according to Scheme 5 below. In this process, the reaction of 2-(6-halo-3-methyl-4-(piperidin-4-yl)naphthalen-2-yl)acetic acid methyl ester (XXXII) with isocyanates XXXIX (where $R^6$ is phenyl or substituted phenyl) gives the urea derivatives XL. Hydrolysis of the methyl ester gives the compounds of the invention of formula XLI.

Scheme 5

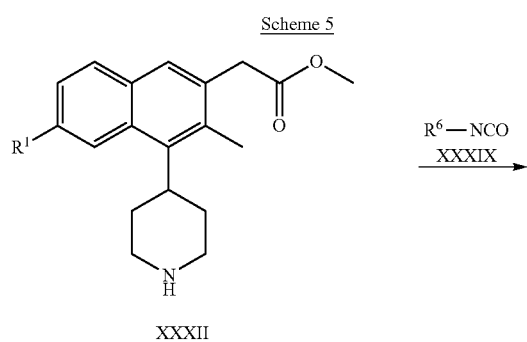

The reaction of 2-(6-halo-3-methyl-4-(piperidin-4-yl) naphthalen-2-yl)acetic acid methyl ester (XXXII) with isocyanates XXXIX to give the urea derivatives XL can be carried out in the presence or absence of a base such as N,N-diisopropyl-ethylamine in a convenient solvent such as methanol or methylene chloride for several hours at temperatures between room temperature and the reflux temperature.

Hydrolysis of the methyl ester in XL to afford compounds of interest of formula XLI can occur in the presence of a base such as lithium hydroxide in mixtures of water and tetrahydrofuran at temperatures between room temperature and the reflux temperature for several hours.

Compounds of the invention of formula XLIV and XLVI (where $R^1$ is defined in the same manner as defined above for the genus of formula I) can be prepared according to Scheme 6 below. In this process, the reaction of 2-(6-halo-3-methyl-4-(piperidin-4-yl)naphthalen-2-yl)acetic acid methyl ester (XXXII) with (2-nitrophenyl)-methanesulfonyl chloride XLII gives the sulfonamide derivative XLIII. Hydrolysis of the methyl ester group in XLIII gives the compound of the invention of formula XLIV. Reduction of the nitro group in XLIII generates the amine intermediate XLV. Hydrolysis of the methyl ester group in XLV gives the compound of the invention of formula XLVI.

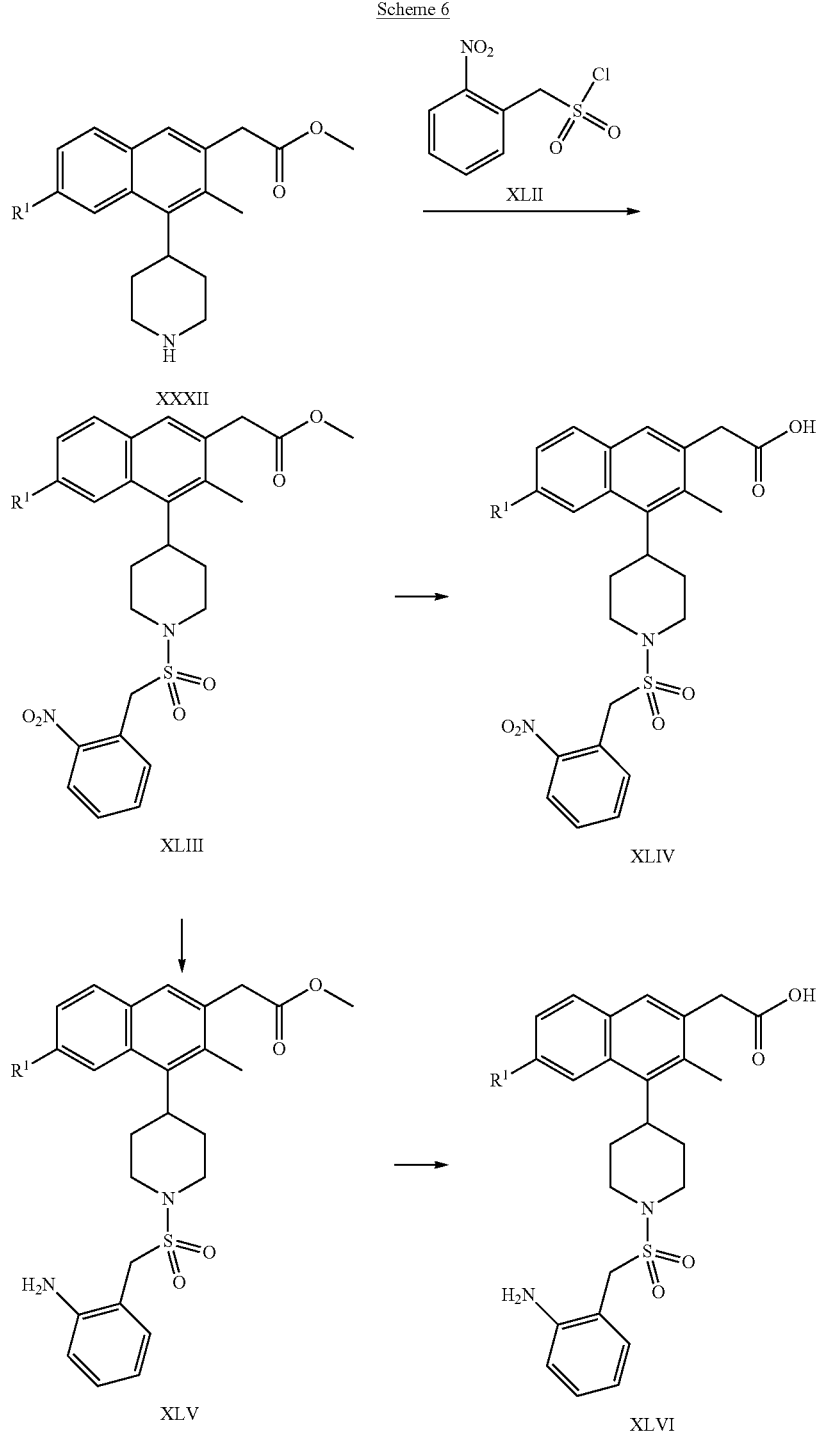

Scheme 6

The reaction of (6-Fluoro-3-methyl-4-piperidin-4-yl-naphthalen-2-yl)-acetic acid methyl ester(XXXII) with (2-nitrophenyl)-methanesulfonyl chloride XLII to give the sulfonamide derivative XLIII can be carried out in the presence of a base such as N,N-diisopropylethylamine in a convenient solvent such as THF or methylene chloride for several hours at temperatures between 0° C. and room temperature.

Hydrolysis of the methyl ester in XLIII to afford compound of interest of formula XLIV can occur in the presence of a base such as lithium hydroxide in mixtures of water and tetrahydrofuran at temperatures between room temperature and the reflux temperature for several hours.

The reduction of the nitro group in XLIII to give the amine derivative XLV can be carried out in the presence of zinc dust and ammonium chloride in a mixture of methanol and water for several hours at temperatures between room temperature and 50° C.

Hydrolysis of the methyl ester in XLV to afford the compound of the invention of formula XLVI can occur in the presence of a base such as lithium hydroxide in mixtures of water and tetrahydrofuran at temperatures between room temperature and the reflux temperature for several hours.

The naphthalene intermediate XXX can be prepared according to Scheme 7 (U.S. application Ser. No. 12/614,478).

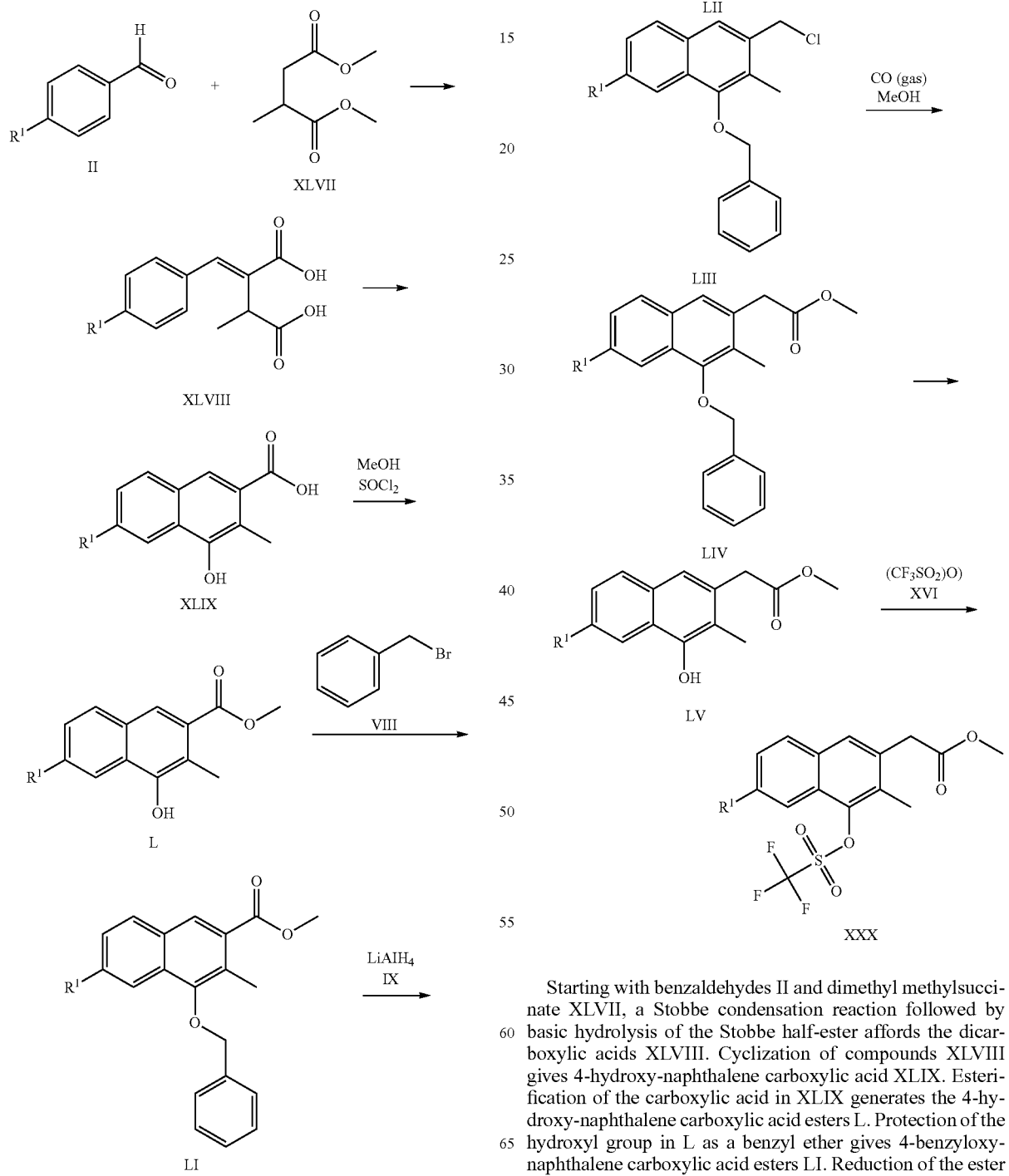

Starting with benzaldehydes II and dimethyl methylsuccinate XLVII, a Stobbe condensation reaction followed by basic hydrolysis of the Stobbe half-ester affords the dicarboxylic acids XLVIII. Cyclization of compounds XLVIII gives 4-hydroxy-naphthalene carboxylic acid XLIX. Esterification of the carboxylic acid in XLIX generates the 4-hydroxy-naphthalene carboxylic acid esters L. Protection of the hydroxyl group in L as a benzyl ether gives 4-benzyloxy-naphthalene carboxylic acid esters LI. Reduction of the ester group in LI affords naphthalen-2-yl methanol compounds LII, which can be transformed to chloromethyl substituted naphthalenes LIII. A carbonylation reaction of LIII in the presence of methanol gives 4-benzyloxy-naphthylacetic acid esters LIV. Deprotection of the benzyl ether in LIV affords 4-hydroxy-naphthylacetic acid esters LV which can undergo sulfonylation to afford the trifluoromethanesulfonate intermediates XXX.

The Stobbe condensation reactions of aldehydes II with dimethyl methylsuccinate XLVII can be carried out using a base such as sodium methoxide, sodium ethoxide, potassium tert-butoxide, or sodium hydride in a suitable solvent such as methanol, ethanol, tert-butanol, toluene, benzene, or mixtures thereof, at temperatures between room temperature and 80° C. for one hour to several hours (Bloomer, J. L.; Stagliano, K. W.; Gazzillo, J. A. *J. Org. Chem.* 58 (1993) 7906). The resulting half-ester intermediates can readily undergo hydrolysis to afford the dicarboxylic acid intermediates XLVIII. This reaction can be carried out in the presence of an aqueous solution of base such as sodium hydroxide or lithium hydroxide, in an inert solvent such as toluene, water, or mixtures thereof, at a temperature between room temperature and the reflux temperature for several hours.

Cyclization of the dicarboxylic acids XLVIII to form 4-hydroxy-naphthalene carboxylic acids XLIX can be accomplished in neat trifluoromethanesulfonic acid at room temperature over several hours (Hong, W. P.; Lim, H. N.; Park, H. W.; Lee, K.-J. *Bull. Korean Chem. Soc.* 26 (2005) 655

Intermediates XLIX can be readily converted to the 4-hydroxy-naphthalene carboxylic acid ester intermediates L in the presence of a catalytic amount of concentrated sulfuric acid and methanol at temperatures between room temperature and 80° C. (or the reflux temperature) for several hours. Alternatively, the esterification reaction can be carried out in the presence of thionyl chloride and methanol at temperatures between 65° C. and 80° C. (or the reflux temperature) for several hours.

Preparation of intermediates LI can be accomplished by treating L with benzyl chloride or benzyl bromide (VIII) in the presence of a base such as potassium carbonate, sodium carbonate, or cesium carbonate. This reaction may occur in an inert organic solvent such as acetone, acetonitrile, or N,N-dimethylformamide at a temperature between room temperature and 80° C. for several hours.

Reduction of the ester group in LI with lithium aluminum hydride (IX) gives the naphthalen-2-yl methanol compounds LII. This reaction can be carried out in an inert organic solvent such as tetrahydrofuran, diethyl ether, toluene, or mixtures thereof, at a temperature between 0° C. and 80° C. for several hours.

The chloromethyl naphthalene intermediates LIM can be prepared by the reaction of compounds LII with carbon tetrachloride and triphenylphosphine in an inert organic solvent such as toluene, acetonitrile, dichloromethane, N,N-dimethylformamide, or tetrahydrofuran at a temperature between 0° C. and 120° C. (or the reflux temperature) for several hours.

Conversion of chlorides LIII to the naphthylacetic acid esters LIV can be accomplished by a palladium catalyzed carbonylation reaction under one atmosphere of carbon monoxide in the presence of a base such as potassium carbonate in methanol and in the presence or absence of a co-solvent such as tetrahydrofuran. This transformation can be carried out using a palladium catalyst such as bis(triphenylphosphine) dichloropalladium(II) at a temperature between room temperature and 90° C. for 10 minutes to several hours (Schoenberg, A.; Bartoletti, I.; Heck, R. F. *J. Org. Chem.* 39 (1974) 3318).

Removal of the benzyl protecting group in LIV through catalytic hydrogenolysis affords the 4-hydroxy-naphthylacetic acid esters LV. This reaction can be carried out under one atmosphere of hydrogen in the presence of a catalyst such as 10% palladium on carbon or 20% palladium hydroxide on carbon in a solvent such as methanol or ethanol at room temperature for several hours. Alternatively, the benzyl ether can be removed in the presence of boron trifluoride diethyl etherate. This reaction can be performed in acetonitrile using sodium iodide as an additive at temperatures between 0° C. to room temperature for reaction times between one hour to several hours (Vankar, Y. D.; Rao, T. *J. Chem. Research (S)* (1985) 232).

Compounds LV can be converted to the trifluoromethanesulfonate esters XXX through a reaction with trifluoromethanesulfonic anhydride (XVI) in the presence of an amine base such as pyridine, triethylamine, or diisopropylethylamine. The reaction may be carried out neat or in an inert solvent such as dichloromethane for several hours at temperatures between 0° C. and room temperature.

EXAMPLES

Although certain exemplary embodiments are depicted and described herein, they should not be considered as limiting the scope of the invention, but merely as being illustrative and representative thereof. The compounds of the present invention can be prepared using appropriate starting materials according to the methods described generally herein and/or by methods available to one of ordinary skill in the art.

All reactions involving air-sensitive reagents were performed under an inert atmosphere. Reagents were used as received from commercial suppliers unless otherwise noted.

Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh. Reverse-phase preparative HPLC was performed using a Waters® Delta-Prep™ 3000 HPLC system from Waters Corporation using one or more of the following columns: a Varian Pursuit® C-18 column (10 µm, 20×150 mm) from Varian, Inc., an Xbridge™ Prep $C_{18}$ column (5 µm, OBD™ 20×100 mm) from Waters Corporation, or a SunFire™ Prep $C_{18}$ column (5 µm, OBD™ 30×100 mm) from Waters Corporation.

Mass spectrometry (MS) or high resolution mass spectrometry (HRMS) was performed using a Waters® ZQ™ 4000 (from Waters Corporation), a Waters® Quattro Micro™ API (from Waters Corporation), a Micromass® Platform II (from Micromass, a division of Waters Corporation), a Bruker® Apex®II FTICR with a 4.7 Tesla magnet (from Bruker Corporation), a Waters® Alliance® 2795-ZQ™2000 (from Waters Corporation), or an MDS Sciex™ API-2000™n API (from MDS Inc.). Mass spectra data generally only indicates the parent ions unless otherwise stated. MS or HRMS data is provided for a particular intermediate or compound where indicated. Molecular formulae and calculated mass values indicate the parent ion and any added or subtracted ions observed.

Nuclear magnetic resonance spectroscopy (NMR) was performed using a Varian® Mercury300 NMR spectrometer (for the $^1$H NMR spectra acquired at 300 MHz), a Varian® Inova400 NMR spectrometer, a Bruker® 300 MHz NMR spectrometer, or a Bruker® 400 MHz NMR spectrometer. $^1$H NMR data is provided for a particular intermediate or compound where indicated.

Part I: Preparation of Starting Materials and Intermediates

Preparation of (6-Fluoro-4-trifluoromethanesulfonyloxy-naphthalen-2-yl)-acetic acid methyl ester 2-[1-(4-Fluoro-phenyl)-meth-(E)-ylidene]-succinic acid A solution of 4-fluorobenzaldehyde (1.0 g, 8.05 mmol) and dimethylsuccinate (1.41 g, 9.66 mmol) in tert-butanol (2 mL) was added drop-wise within 30 minutes to a refluxing mixture of potassium tert-butoxide (0.994 g, 8.86 mmol) in tert-butanol (8 mL). Refluxing was continued until all the starting material was consumed as demonstrated by TLC analysis. The reaction temperature was warmed to room temperature, and tert-butanol was removed in vacuo. The residue was dissolved in 1.0 N aqueous HCl (10 mL) and was extracted with ethyl acetate (2×5 mL). The combined organic extracts were dried over anhydrous sodium sulfate and concentrated in vacuo to obtain an oil. This crude product was dissolved in methanol (10 mL). An aqueous solution of 2.0 N NaOH (10 mL) was added into the solution at room temperature and the mixture was refluxed overnight. The resulting suspension was concentrated, and the obtained residue was dissolved in water (10 mL). The resulting solution was washed with ethyl acetate (2×10 mL). The aqueous layer was acidified (pH~2) with the drop wise addition of concentrated HCl. The resulting mixture was extracted with ethyl acetate (3×10 mL). The combined organic extracts were dried over anhydrous sodium sulfate and concentrated in vacuo to obtain a crude residue. Crystallization from ether/hexane gave 2-[1-(4-fluoro-phenyl)-meth-(E)-ylidene]-succinic acid (0.74 g, 41%) as a white solid. MS cald. for $C_{11}H_8FO_4$ [(M−H)$^-$]: 223, obsd. 223.1.

6-Fluoro-4-hydroxy-naphthalene-2-carboxylic acid

A solution of 2-[1-(4-fluoro-phenyl)-meth-(E)-ylidene]-succinic acid (0.100 g, 0.44 mmol) in trifluoromethanesulfonic acid (0.5 mL) was stirred at room temperature for 16 hours. The resulting mixture was carefully poured into ice cold water with continuous stirring to obtain a solid precipitate, which was filtered, washed with water and dried under vacuum to yield 6-fluoro-4-hydroxy-naphthalene-2-carboxylic acid (0.065 g, 71%) as yellow solid. This crude product was pure enough to proceed to next step without further purification.

6-Fluoro-4-hydroxy-naphthalene-2-carboxylic acid methyl ester

To a solution of 6-fluoro-4-hydroxy-naphthalene-2-carboxylic acid (0.500 g, 2.42 mmol) in MeOH (10 mL) was added thionyl chloride (0.265 ml, 3.63 mmol) drop-wise at 0° C. and the resulting mixture was refluxed for 5 hours. Methanol was distilled off under reduced pressure, and the residue was diluted with water (5 mL) and extracted with ethyl acetate (2×10 mL). The combined organic extracts were washed with water (5 mL) followed by brine (5 mL), dried and concentrated under reduced pressure to obtain the crude product. Silica gel column chromatography (5% ethyl acetate in hexanes) afforded 6-fluoro-4-hydroxy-naphthalene-2-carboxylic acid methyl ester (0.150 g, 28%) as a light yellow solid. MS cald. for $C_{12}H_{10}FO_3$ [(M+H)$^+$]: 221, obsd. 221.2.

4-Benzyloxy-6-fluoro-naphthalene-2-carboxylic acid methyl ester

To a solution of 6-fluoro-4-hydroxy-naphthalene-2-carboxylic acid methyl ester (3.7 g, 16.8 mmol) in dry DMF (40 mL) was added $K_2CO_3$ (3.25 g, 23.5 mmol), benzyl bromide (3.44 g, 20.2 mmol) and Bu$_4$NI (0.02 g) simultaneously at room temperature under nitrogen. The reaction mixture was stirred for 3 hours at room temperature. The mixture was diluted with water (60 mL) and extracted with ethyl acetate (2×100 mL). The combined organic extracts were washed with water (30 mL), brine (30 mL), dried over anhydrous sodium sulfate and concentrated in vacuo to obtain the crude product. Silica gel column chromatography (2%-5% ethyl acetate in hexanes) afforded 4-benzyloxy-6-fluoro-naphthalene-2-carboxylic acid methyl ester (4.6 g, 88%) as an off-white solid. MS cald. for $C_{19}H_{16}FO_3$ [(M+H)$^+$]: 311, obsd. 311.0.

(4-Benzyloxy-6-fluoro-naphthalen-2-yl)-methanol

To a suspension of LiAlH$_4$ (1.76 g, 46.4 mmol) in dry THF (20 mL) was added a solution of 4-benzyloxy-6-fluoro-naphthalene-2-carboxylic acid methyl ester (4.80 g, 15.5 mmol) in THF (30 mL) drop wise at 0° C. under nitrogen. The reaction mixture was stirred at room temperature for 3 hours. The reaction mixture was quenched through the addition of an aqueous solution of HCl (50%; 50 mL) and the resulting mixture was filtered through a bed of celite. The filtrate was extracted with ethyl acetate (2×100 mL). The combined organic extracts were washed with water (30 mL) followed by brine (30 mL), dried and concentrated in vacuo to obtain (4-benzyloxy-6-fluoro-naphthalen-2-yl)-methanol (3.6 g, 82.2%). The crude product was pure enough to proceed to the next step without further purification.

1-Benzyloxy-3-chloromethyl-7-fluoro-naphthalene

To a solution of triphenylphosphine (37.2 g, 142 mmol) in dry THF (160 mL) was added CCl$_4$ (50 mL). The reaction mixture was stirred for 10 minutes and (4-benzyloxy-6-fluoro-naphthalen-2-yl)-methanol (20.0 g, 70.8 mmol) was introduced as a solid at room temperature under nitrogen. The resulting solution was refluxed for 2 hours. THF was distilled off under reduced pressure, and the remaining material diluted with water (100 mL) and extracted with ethyl acetate (2×150 mL). The combined organic extracts were washed with water (50 mL), brine (50 mL), dried over anhydrous sodium sulfate and concentrated in vacuo. The obtained crude product was purified over silica gel column chromatography (100-200 mesh, 5% ethyl acetate in hexanes) to yield compound 1-benzyloxy-3-chloromethyl-7-fluoro-naphthalene (19.3 g, 90.6%) as a white solid.

(4-Benzyloxy-6-fluoro-naphthalen-2-yl)-acetic acid methyl ester

To a stirred solution of 1-benzyloxy-3-chloromethyl-7-fluoro-naphthalene (19.3 g, 64.2 mmol) in a 2:1 THF-MeOH (300 mL) was added $K_2CO_3$ (9.75 g, 70.6 mmol) and PdCl$_2$(PPh$_3$)$_2$ (2.25 g, 3.2 mmol) at room temperature. The solution was degassed (by purging with argon for 5 minutes) and stirred under carbon monoxide (balloon pressure) at room temperature overnight. The solvents were distilled off under reduced pressure, and the obtained crude residue was diluted with water (150 ml) and extracted with ethyl acetate (2×200 mL). The combined organic extracts were washed with water (50 ml), brine (50 ml), dried over anhydrous sodium sulfate and concentrated in vacuo to obtain the crude product. Silica gel chromatography (100-200 mesh, 5% ethyl acetate in hexane) yielded (4-benzyloxy-6-fluoro-naphthalen-2-yl)-acetic acid methyl ester (18.5 g, 89%) as a white solid. MS cald. for $C_{20}H_{17}FO_3$ [(M+H)$^+$]: 325, obsd. 325.2.

(6-Fluoro-4-hydroxy-naphthalen-2-yl)-acetic acid methyl ester

To a stirred solution of (4-benzyloxy-6-fluoro-naphthalen-2-yl)-acetic acid methyl ester (18.5 g, 57.0 mmol) in methanol (200 mL) was added 10% palladium on carbon (2.78 g). The resulting mixture was vigorously stirred under a balloon of hydrogen overnight. The reaction mixture was filtered through celite. The filtrate was concentrated in vacuo to obtain a crude product. Silica gel chromatography (10% ethyl acetate-hexane) afforded (6-fluoro-4-hydroxy-naphthalen-2-yl)-acetic acid methyl ester (10.24 g, 76%) as a white solid. MS cald. for $C_{13}H_{12}FO_3$ [(M+H)$^+$]: 235, obsd. 235.2.

(6-Fluoro-4-trifluoromethanesulfonyloxy-naphthalen-2-yl)-acetic acid methyl ester To a mixture of (6-fluoro-4-hydroxy-naphthalen-2-yl)-acetic acid methyl ester (350 mg, 1.5 mmol) and trifluoromethanesulfonic anhydride (506 mg, 1.8 mmol) in dichloromethane (20 mL), which was cooled to 0° C. in an ice bath, pyridine (0.6 mL) was added dropwise. The reaction mixture was stirred at 0° C. for 2 hours and then concentrated in vacuo. The residue was dissolved in ethyl acetate (50 mL). The resulting solution was washed with water, 1 N aqueous hydrochloric acid, water, and brine, then dried over sodium sulfate, filtered, and concentrated in vacuo. The residue was purified by column chromatography (0-30% ethyl acetate in hexanes) to afford (6-fluoro-4-trifluoromethanesulfonyloxy-naphthalen-2-yl)-acetic acid methyl ester (450 mg, 82%) as a light yellow solid.

Preparation of 4-(4,4,5,5-Tetramethyl-[1,3,2]dioxaborolan-2-yl)-3,6-dihydro-2H-pyridine-1-carboxylic acid tert-butyl ester 4-Oxo-piperidine-1-carboxylic acid tert-butyl ester To a stirred solution of 4-piperidone monohydrate hydrochloride (available from Sigma-Aldrich; 50 g, 326 mmol) in 1,4-dioxane (500 mL) was added an solution of sodium bicarbonate (60 g, 714 mmol) in water (170 mL), followed by the dropwise addition of di-tert-butyl dicarbonate (97 mL, 422 mmol) at room temperature. The reaction mixture was stirred for 30 minutes at room temperature and then overnight at 70° C. The reaction mixture was concentrated to remove dioxane, and the remaining mixture was extracted with ethyl acetate (3×500 mL). The combined organic extracts were washed with brine and then evaporated under reduced pressure to give 4-oxo-piperidine-1-carboxylic acid tert-butyl ester (60.21 g, 93%) as a white solid, which was used directly in the next step without further purification.

4-Trifluoromethanesulfonyloxy-3,6-dihydro-2H-pyridine-1-carboxylic acid tert-butyl ester n-Butyllithium (1.9 M; 30.6 mL, 58 mmol) was added dropwise to a stirred solution of diisopropylamine (4.6 mL, 32.6 mmol) in THF (60 mL) at about −75° C. under nitrogen. The reaction temperature was brought to about 0° C. and the mixture was stirred for 1 h at this temperature. The reaction mixture was cooled to −75° C. and a solution of 4-oxo-piperidine-1-carboxylic acid tert-butyl ester (10.0 g, 50.2 mmol) in THF was added. The mixture was stirred for 1 h at −75° C., and then N-phenylbis(trifluoromethanesulfonimide) (19.7 g, 55.1 mmol) was added. The mixture was allowed to warm to room temperature and stir overnight. The reaction mixture was extracted with ethyl acetate and the extracts were washed with water. The organic extracts were dried over $Na_2SO_4$, filtered, evaporated, and purified by chromatography on an alumina column to give 4-trifluoromethanesulfonyloxy-3,6-dihydro-2H-pyridine-1-carboxylic acid tert-butyl ester (8 g, 48%). $^1$H NMR (300 MHz, CDCl$_3$) δ ppm: 5.75 (s, 1H), 4.03 (s, 2H), 3.60-3.63 (m, 2H), 1.46 (s, 9H); MS cald. for $C_{11}H_{17}F_3NO_5S$ [(M+H)$^+$] 332, obsd. 332.5.

4-(4,4,5,5-Tetramethyl-[1,3,2]dioxaborolan-2-yl)-3,6-dihydro-2H-pyridine-1-carboxylic acid tert-butyl ester A mixture of 4-trifluoromethanesulfonyloxy-3,6-dihydro-2H-pyridine-1-carboxylic acid tert-butyl ester (which may be prepared as described above; 900 mg, 2.7 mmol), bis(pinacolato)diboron (available from Sigma-Aldrich; 760 mg, 3 mmol), and potassium acetate (799 mg, 8.1 mmol) and dioxane (15 mL) was degassed with argon for 30 min. [1,1'-bis(diphenylphosphino)ferrocene]dichloro-palladium(II), complex with dichloromethane (available from Sigma-Aldrich; 66.5 mg, 0.08 mmol) and 1,1'-bis(diphenylphosphino)ferrocene (45 mg, 0.08 mmol) were added and the mixture was degassed with argon for 10 min. The mixture was heated overnight at 80-90° C., allowed to cool to room temperature, and then filtered through celite. The filtrate was evaporated under reduced pressure and the residue was purified by column chromatography to give 4-(4,4,5,5-tetramethyl-[1,3,2]dioxaborolan-2-yl)-3,6-dihydro-2H-pyridine-1-carboxylic acid tert-butyl ester (500 mg, 60%). $^1$H NMR (300 MHz, DMSO-d$_6$) δ ppm: 6.38 (br s, 1H), 3.82-3.90 (m, 2H), 2.05-2.10 (m, 2H), 1.40 (s, 9H), 1.20 (s, 12H); MS cald. for $C_{16}H_{29}BNO_4$ [(M+H)$^+$] 310, obsd. 310.2.

Preparation of (6-fluoro-4-piperidin-4-yl-naphthalen-2-yl)-acetic acid methyl ester trifluoroacetate salt 4-(7-Fluoro-3-methoxycarbonylmethyl-naphthalen-1-yl)-3,6-dihydro-2H-pyridine-1-carboxylic acid tert-butyl ester Anhydrous potassium carbonate (0.40 g, 2.9 mmol) was added to a stirred solution of compound (6-fluoro-4-trifluoromethanesulfonyloxy-naphthalen-2-yl)-acetic acid methyl ester (which may be prepared as described above; 0.37 g, 1 mmol) and 4-(4,4,5,5-tetramethyl-[1,3,2]dioxaborolan-2-yl)-3,6-dihydro-2H-pyridine-1-carboxylic acid tert-butyl ester (0.30 g, 0.97 mmol) in dry DMF-MeOH (4:1, 5 mL) in a pressure tube. The mixture was deoxygenated by bubbling with argon for 15 min. [1,1'-Bis(diphenylphosphino)ferrocene]dichloropalladium(II), complex with dichloromethane (available from Sigma-Aldrich; 80 mg, 0.1 mmol) was added under argon. The mixture was heated at reflux for 12 h and then cooled. Ethyl acetate (20 mL) was added and the mixture was filtered through a pad of celite. The celite was washed with ethyl acetate and the combined filtrates were concentrated under reduced pressure. The residue was purified by silica gel column chromatography (100-200 mesh), using 5% ethyl acetate/hexanes as eluent, to give 4-(7-fluoro-3-methoxycarbonylmethyl-naphthalen-1-yl)-3,6-dihydro-2H-pyridine-1-carboxylic acid tert-butyl ester (0.21 g, 54%). $^1$H NMR (300 MHz, DMSO-d$_6$) δ ppm: 7.78 (dd, J=6.6, 4.4 Hz, 1H), 7.64 (s, 1H), 7.51 (dd, J=7.1, 1.1 Hz, 1H), 7.21-7.26 (m, 2H), 5.77 (s, 1H), 4.12 (s, 2H), 3.70-3.76 (m, 7H), 2.45-2.50 (m, 2H), 1.52 (m, 9H); MS cald. for $C_{23}H_{27}FNO_4$ [(M+H)$^+$] 400, obsd. 400.2.

4-(7-Fluoro-3-methoxycarbonylmethyl-naphthalen-1-yl)-piperidine-1-carboxylic acid tert-butyl ester 10% Palladium on carbon (0.09 g) was added to a deoxygenated solution of 4-(7-fluoro-3-methoxycarbonylmethyl-naphthalen-1-yl)-3,6-dihydro-2H-pyridine-1-carboxylic acid tert-butyl ester (which may be prepared as described above; 0.64 g, 1.6 mmol) in ethanol (30 mL) in a Parr shaker vessel. The mixture was hydrogenated at 60 psi for 16 h and then filtered through a pad of celite. The celite was washed with ethanol (2×5 mL) and the combined filtrates were concentrated under reduced pressure. The residue was purified by silica gel column chromatography (100-200 mesh), using 20% ethyl acetate/hexanes as eluent, to give 4-(7-fluoro-3-methoxycarbonylmethyl-naphthalen-1-yl)-piperidine-1-carboxylic acid tert-butyl ester (0.40 g, 62%) as a sticky colorless solid. MS cald. for $C_{23}H_{29}FNO_4$ [(M+H)$^+$] 402, obsd. 402.4.

(6-Fluoro-4-piperidin-4-yl-naphthalen-2-yl)-acetic acid methyl ester trifluoroacetate salt Trifluoroacetic acid (2.9 mL, 38 mmol) was added at 0° C. to a stirred solution of 4-(7-fluoro-3-methoxycarbonylmethyl-naphthalen-1-yl)-piperidine-1-carboxylic acid tert-butyl ester (which may be prepared as described above; 1.05 g, 2.6 mmol) in dry CH$_2$Cl$_2$ (25 mL) under nitrogen. The solution was stirred at room temperature for 16 h and then the solvent was evaporated under reduced pressure. The residue was triturated with diethyl ether (3×5 mL) and dried under vacuum to give (6-fluoro-4-piperidin-4-yl-naphthalen-2-yl)-acetic acid methyl ester trifluoroacetate salt (0.80 g, 74%) as a white solid. MS cald. for $C_{18}H_{21}FNO_2$ [(M+H)$^+$] 302, obsd. 302.4.

Preparation of (6-fluoro-3-methyl-4-trifluoromethanesulfonyloxy-naphthalen-2-yl)-acetic acid methyl ester 2-[1-(4-Fluoro-phenyl)-meth-(E)-ylidene]-3-methyl-succinic acid To a suspension of sodium hydride (60% in paraffin oil, 31 g, 775 mmol) in toluene (150 mL) was added a solution of 4-fluorobenzaldehyde (30 g, 242 mmol) and dimethyl methylsuccinate (58 g, 362 mmol) in toluene (150 mL) over 1 hour at 0° C. under nitrogen. The reaction was initiated by addition of a drop of methanol at room temperature and was stirred at room temperature for 2 hours. The reaction was quenched by slow addition of 2.0 N aqueous NaOH (300 mL) at 0° C. The resulting mixture was stirred at 110° C. for 4 hours. The mixture was then cooled to room temperature and the aqueous layer was diluted with water (300 mL) and washed with Et$_2$O (2×300 mL). The aqueous phase was cooled in an ice-water bath. Addition of concentrated HCl was followed by extraction with ethyl acetate (2×100 mL). The combined organic extracts were washed with water (50 mL) followed by brine (50 mL). The organic phase was dried over anhydrous sodium sulfate and concentrated. The residue was crystallized from ethyl acetate-hexanes to give 2-[1-(4-fluoro-phenyl)-meth-(E)-ylidene]-3-methyl succinic acid. The procedure above was repeated using a separate amount of 4-fluorobenzaldehyde (30 g, 242 mmol). The products of the two reactions were combined to provide 2-[1-(4-fluoro-phenyl)-meth-(E)-ylidene]-3-methyl succinic acid as a pale yellow solid (28 g, 24% overall). MS cald. for $C_{12}H_{12}FO_4$ [(M+H)$^+$] 239, obsd. 239.2.

6-Fluoro-4-hydroxy-3-methyl-naphthalene-2-carboxylic acid

A solution of 2-[1-(4-fluoro-phenyl)-meth-(E)-ylidene]-3-methyl succinic acid (28 g, 118 mmol) in trifluoromethanesulfonic acid (140 mL) was stirred at room temperature for 16 h. The resulting mixture was carefully poured into ice cooled water with continuous stirring to obtain a solid precipitate, which was filtered, washed with water and dried in vacuo to yield 6-fluoro-4-hydroxy-3-methyl-naphthalene-2-carboxylic acid (28 g, >100% crude) as yellow solid. This crude product was used in the next step without further purification. MS cald. for $C_{12}H_8FO_3$ [(M−H)$^-$] 219, obsd. 218.9.

6-Fluoro-4-hydroxy-3-methyl-naphthalene-2-carboxylic acid methyl ester

To a 0° C. solution of crude 6-fluoro-4-hydroxy-3-methyl-naphthalene-2-carboxylic acid (28 g, approx. 118 mmol) in MeOH (240 mL) was added concentrated sulfuric acid (18.9 mL, 382 mmol) dropwise. The reaction mixture was then warmed to room temperature and refluxed overnight. After this time, the methanol was distilled off under reduced pressure, and the crude mixture was diluted with ethyl acetate. This solution was washed with saturated aqueous NaHCO$_3$. The organic phase was dried over Na$_2$SO$_4$, filtered and concentrated under reduced pressure to give the crude product. Silica gel column chromatography (6% ethyl acetate-hexane) afforded 6-fluoro-4-hydroxy-3-methyl-naphthalene-2-carboxylic acid methyl ester (14.8 g, 54%) as light yellow solid. MS cald. for $C_{13}H_{12}FO_3$ [(M+H)$^+$] 235, obsd. 235.2.

4-Benzyloxy-6-fluoro-3-methyl-naphthalene-2-carboxylic acid methyl ester

To a solution of 6-fluoro-4-hydroxy-3-methyl-naphthalene-2-carboxylic acid methyl ester (21.7 g, 92.7 mmol) in dry DMF (250 mL) was added K$_2$CO$_3$ (17.9 g, 130 mmol), benzyl bromide (13 mL, 111 mmol) and Bu$_4$NI (0.250 g) at room temperature under nitrogen. The reaction mixture was stirred for 3 hours at room temperature. The reaction mixture was diluted with water and extracted with ethyl acetate. The combined organic extracts were washed with water, brine, dried over anhydrous sodium sulfate and concentrated to give the crude product, which was purified using silica gel column chromatography (2-5% ethyl acetate-hexane) to yield 4-benzyloxy-6-fluoro-3-methyl-naphthalene-2-carboxylic acid methyl ester (25.4 g, 84%) as an off-white solid. MS cald. for $C_{20}H_{18}FO_3$ [(M+H)$^+$] 325, obsd. 325.1.

(4-Benzyloxy-6-fluoro-3-methyl-naphthalen-2-yl)-methanol

To a suspension of LiAlH$_4$ (8.8 g, 235 mmol) in dry THF (120 mL) was added a solution of 4-benzyloxy-6-fluoro-3- methyl-naphthalene-2-carboxylic acid methyl ester (25.4 g, 78.4 mmol) in THF (180 mL) dropwise at 0° C. under nitrogen. The reaction mixture was stirred at room temperature for 3 hours. After this time, the reaction mixture was cooled to 0° C. and quenched carefully via addition of cold water (10 mL) followed by 15% NaOH solution (10 mL) and additional water. The resulting solution was stirred for one hour, then filtered through a sintered glass funnel. The filter pad was washed with THF (50 mL). The combined filtrates were dried over $Na_2SO_4$, filtered, and concentrated to afford (4-benzyloxy-6-fluoro-3-methyl-naphthalen-2-yl)-methanol (21.5 g, 92%, crude) as a white solid. The crude product was used in the next step without further purification. MS cald. for $C_{19}H_{16}FO_2$ [(M−H)⁻] 295, obsd. 294.9.

1-Benzyloxy-3-chloromethyl-7-fluoro-2-methyl-naphthalene

To a solution of triphenylphosphine (41.6 g, 159 mmol) in dry THF (190 mL) was added $CCl_4$ (59 mL). The reaction mixture was stirred for 10 minutes and (4-benzyloxy-6-fluoro-3-methyl-naphthalen-2-yl)-methanol (21.5 g, 72.6 mmol) was introduced as a solid at room temperature under nitrogen. The resulting solution was refluxed for 2 hours. The solvent was distilled off under reduced pressure, and the residue was diluted with water. The resulting mixture was extracted twice with ethyl acetate. The combined organic extracts were washed with water and brine, dried over anhydrous sodium sulfate, filtered, and concentrated. Silica gel column chromatography (100-200 mesh, 5% ethyl acetate in hexanes) provided 1-benzyloxy-3-chloromethyl-7-fluoro-2-methyl-naphthalene (18.5 g, 81%) as an off-white solid.

(4-Benzyloxy-6-fluoro-3-methyl-naphthalen-2-yl)-acetic acid methyl ester

To a stirred solution of 1-benzyloxy-3-chloromethyl-7-fluoro-2-methyl-naphthalene (18.5 g, 58.9 mmol) in a THF-methanol mixture (2:3; 500 mL) was added $K_2CO_3$ (8.94 g, 64.7 mmol) and $PdCl_2(PPh_3)_2$ (2.06 g, 2.96 mmol) at room temperature. The solution was degassed by purging with argon for 5 minutes. The reaction mixture was stirred under a balloon of carbon monoxide overnight at room temperature. After this time, the reaction progress was monitored by TLC (5% ethyl acetate in hexanes). The reaction mixture was concentrated, and the obtained crude residue was diluted with water and extracted with ethyl acetate. The combined organic extracts were washed with water and brine, dried over anhydrous sodium sulfate, filtered, and concentrated to give a crude product. Silica gel chromatography (100-200 mesh, 5% ethyl acetate-hexanes) yielded (4-benzyloxy-6-fluoro-3-methyl-naphthalen-2-yl)-acetic acid methyl ester (15.8 g, 80%) as a pale yellow solid. MS cald. for $C_{21}H_{20}FO_3$ [(M+H)⁺] 339, obsd. 339.0.

(6-Fluoro-4-hydroxy-3-methyl-naphthalen-2-yl)-acetic acid methyl ester

To a stirred solution of (4-benzyloxy-6-fluoro-3-methyl-naphthalen-2-yl)-acetic acid methyl ester (15.8 g, 46.7 mmol) in MeOH (150 mL) was added 10% palladium on carbon (2.4 g). The resulting mixture was vigorously stirred under a balloon of hydrogen overnight. The reaction mixture was filtered through celite. The filtrate was concentrated to give the crude product, which was purified by silica gel chromatography (10% ethyl acetate in hexanes) to yield (6-fluoro-4-hydroxy-3-methyl-naphthalen-2-yl)-acetic acid methyl ester (9.5 g, 82%) as a white solid. MS cald. for $C_1H_{13}FO_3$ [(M+H)⁺] 249, obsd. 249.1.

(6-Fluoro-3-methyl-4-trifluoromethanesulfonyloxy-naphthalen-2-yl)-acetic acid methyl ester A light yellow solution of (6-fluoro-4-hydroxy-3-methyl-naphthalen-2-yl)-acetic acid methyl ester (which may be prepared as described above; 12.2 g, 49.1 mmol) in methylene chloride (500 mL) was cooled to 0° C. using an ice-acetone bath. Pyridine (5.17 mL, 63.9 mmol) was added and then trifluoromethanesulfonic acid anhydride (20.8 g, 73.7 mmol) was added dropwise to the cold solution over 40 minutes. The resulting light yellow solution was stirred for two hours at 0° C. before being warmed to room temperature. The reaction mixture was stirred for another 30 minutes at room temperature. The mixture was quenched with water (300 mL) and the two layers were separated. The aqueous layer was extracted with dichloromethane (200 mL). The combined organic layers were washed with brine, dried over anhydrous $MgSO_4$, filtered, and concentrated to give the crude product as a light yellow solid. The crude product was dissolved in dichloromethane (~50 mL) with heating and then the mixture was diluted with hexanes (~100 mL). Some of the solvent was removed by heating with a heat gun. The resulting light brown solution was stored in the freezer for 15 hours. A white solid precipitated, which was collected by filtration and washed with hexanes. After air drying, (6-fluoro-3-methyl-4-trifluoromethanesulfonyloxy-naphthalen-2-yl)-acetic acid methyl ester (14.32 g, 77%) was isolated. $^1H$ NMR (400 MHz, DMSO-$d_6$) δ ppm 7.83 (dd, J=9.03, 5.52 Hz, 1H), 7.75 (s, 1H), 7.65 (dd, J=10.29, 2.51 Hz, 1H), 7.31 (td, J=8.60, 2.38 Hz, 1H), 3.85 (s, 2H), 3.74 (s, 3H).

Preparation of (6-Fluoro-3-methyl-4-piperidin-4-yl-naphthalen-2-yl)-acetic acid methyl ester (4-(7-Fluoro-3-methoxycarbonylmethyl-2-methyl-naphthalen-1-yl)-piperidine-1-carboxylic acid tert-butyl ester An oven-dried 3-neck 50 mL round-bottom flask equipped with a 100 mL addition funnel, a rubber septum, and an L-shape adapter was charged with zinc dust (1.31 g, 20.0 mmol) and lithium chloride (848 mg, 20.0 mmol) under nitrogen. The solids were stirred and the mixture was heated at 171° C. under high vacuum for 1.5 hours. The flask was cooled to room temperature, backfilled with nitrogen, and dry tetrahydrofuran (2.0 mL) was added to the grey mixture. The reaction flask was equipped with a thermometer. To the reaction mixture was added 1,2-dibromoethane (376 mg, 2.00 mmol) and the suspension was heated gently with heat gun to the point of gas evolution and foaming. Upon completion of the gas evolution, the mixture was allowed to cool to 50° C. and heated again. This process was repeated three times to make sure the zinc dust was activated completely. The activated zinc dust was treated with chlorotrimethylsilane (217 mg, 2.00 mmol) and the suspension was stirred for 15 minutes at room temperature. The resulting mixture was treated with a solution of 4-iodopiperidine-1-carboxylic acid tert-butyl ester (3.112 g, 10.0 mmol) in tetrahydrofuran (5.0 mL) at room temperature. After the addition, the reaction mixture was heated with a heat gun to initiate the reaction and the temperature increased to 68° C. After cooling to 50° C., it was again heated to 60° C. (oil bath temperature) and stirred for 1.5 hours. The reaction mixture was cooled to room temperature and diluted with tetrahydrofuran (5 mL) and stirring was stopped to allow the excess zinc dust to settle over three hours.

In a separate single-neck 50 mL round bottom flask, palladium(II) acetate (112 mg, 0.5 mmol) and 2-dicyclohexylphosphino-2',6'-dimethoxybiphenyl (S-Phos) (411 mg, 1 mmol) were combined with dry tetrahydrofuran (3 mL) at room temperature under nitrogen. After stirring for 10 minutes at room temperature, a solution of (6-fluoro-3-methyl-4-trifluoromethanesulfonyloxy-naphthalen-2-yl)-acetic acid methyl ester (which may be prepared as described above; 1.52 g, 4.00 mmol) was added to the light greenish-brown solution. After 2-3 minutes, the freshly prepared and clear organozinc compound in THF (described above) (~5.0 mmol) was added at room temperature. The resulting light greenish-brown solution was stirred at 65° C. for 15 hours under nitrogen. The reaction mixture was cooled to room temperature and quenched with saturated ammonium chloride solution. The organic compound was extracted into ethyl acetate (3×50 mL) and the combined extracts were washed with brine solution and dried over anhydrous magnesium sulfate. Filtration and concentration gave the crude product which was purified by flash chromatography (150 g ISCO column, eluting with 0-50% ethyl acetate/hexanes) to give (4-(7-fluoro-3-methoxycarbonylmethyl-2-methyl-naphthalen-1-yl)-piperidine-1-carboxylic acid tert-butyl ester (1.02 g, 61%) as a light yellow solid. MS cald. for $C_{24}H_{31}FNO_4$ [(M+H)$^+$] 416, obsd. 416.2.

(6-Fluoro-3-methyl-4-piperidin-4-yl-naphthalen-2-yl)acetic acid methyl ester trifluoroacetate salt To a yellow solution of (4-(7-fluoro-3-methoxycarbonyl-methyl-2-methyl-naphthalen-1-yl)-piperidine-1-carboxylic acid tert-butyl ester (200 mg, 0.48 mmol) in dichloromethane (10 mL) was added excess trifluoroacetic acid (1.1 g, 742 μL, 9.6 mmol) at room temperature under nitrogen. The resulting dark brown solution was stirred for 2 hours at room temperature under nitrogen. The solvent was removed under vacuum and the residue (~270 mg) was purified by flash chromatography (40 g ISCO column, 0-100% ethyl acetate/hexanes then 20% MeOH/dichloromethane) to give (6-fluoro-3-methyl-4-piperidin-4-yl-naphthalen-2-yl)-acetic acid methyl ester trifluoroacetate salt as a light yellow solid (110 mg, 53%). MS cald. for $C_{19}H_{23}FNO_2$ [(M+H)$^+$] 316, obsd. 316.1.

(6-Fluoro-3-methyl-4-piperidin-4-yl-naphthalen-2-yl)-acetic acid methyl ester

A mixture of (6-fluoro-3-methyl-4-piperidin-4-yl-naphthalen-2-yl)-acetic acid methyl ester trifluoroacetate salt (50 mg, 0.116 mmol) in saturated aqueous sodium bicarbonate (10 mL) was stirred at room temperature for several minutes. The resulting solution was extracted with ethyl acetate (2×15 mL). The combined organic layers were dried over anhydrous Na$_2$SO$_4$, filtered, and concentrated to afford (6-fluoro-3-methyl-4-piperidin-4-yl-naphthalen-2-yl)-acetic acid methyl ester (36 mg, 97%).

Part II: Preparation of Certain Compounds of the Invention

Example 1

[4-(1-Benzenesulfonyl-piperidin-4-yl)-6-fluoro-naphthalen-2-yl]-acetic acid

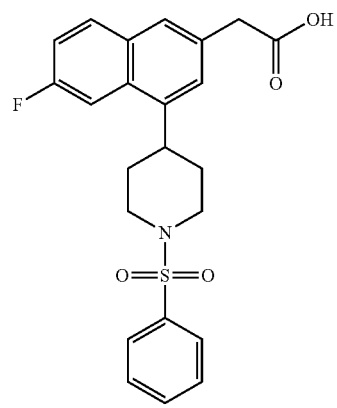 [SMILES: O=C(O)Cc1cc(C2CCN(S(=O)(=O)c3ccccc3)CC2)c2cc(F)ccc2c1]

[4-(1-Benzenesulfonyl-piperidin-4-yl)-6-fluoro-naphthalen-2-yl]-acetic acid methyl ester Diisopropylethylamine (90 μL, 0.52 mmol) was added to a solution of (6-fluoro-4-piperidin-4-yl-naphthalen-2-yl)-acetic acid methyl ester trifluoroacetate salt (which may be prepared as described above; 100 mg, 0.24 mmol) in tetrahydrofuran (6 mL). Phenylsulfonyl chloride (available from Sigma-Aldrich; 43 μL, 0.34 mmol) was added and the mixture was stirred at room temperature overnight. The solvent was evaporated under reduced pressure. Water and ethyl acetate were added and the organic layer was dried over Na$_2$SO$_4$, filtered, and evaporated under reduced pressure. The residue was purified by silica gel column chromatography (100-200 mesh) to give [441-benzenesulfonyl-piperidin-4-yl)-6-fluoro-naphthalen-2-yl]-acetic acid methyl ester (64 mg, 60%). MS cald. for $C_{24}H_{25}FNO_4S$ [(M+H)$^+$]: 442, obsd. 442.2.

[4-(1-Benzenesulfonyl-piperidin-4-yl)-6-fluoro-naphthalen-2-yl]-acetic acid

To a stirred solution of [4-(1-benzenesulfonyl-piperidin-4-yl)-6-fluoro-naphthalen-2-yl]-acetic acid methyl ester (90 mg, 0.2 mmol) in THF (8 mL) was added a solution of lithium hydroxide monohydrate (26 mg, 0.6 mmol) in water (2 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give [4-(1-benzenesulfonyl-piperidin-4-yl)-6-fluoro-naphthalen-2-yl]-acetic acid (35 mg, 40%) as an off-white solid. $^1$H NMR (400 MHz, DMSO-d$_6$) δ ppm 12.36 (br s, 1H), 7.92-7.98 (m, 1H), 7.88 (d, J=11.2 Hz, 1H), 7.81 (d, J=7.8 Hz, 2H), 7.76 (d, J=6.8 Hz, 1H), 7.65-7.73 (m, 3H), 7.33-7.42 (m, 2H), 3.82 (d, J=11.7 Hz, 2H), 3.71 (s, 2H), 1.90 (d, J=11.2 Hz, 2H), 1.69-1.82 (m, 2H); MS cald. for $C_{23}H_{23}FNO_4S$ [(M–H)⁻]: 426, obsd. 426.2.

Example 2

{6-Fluoro-4-[1-(toluene-4-sulfonyl)-piperidin-4-yl]-naphthalen-2-yl}-acetic acid

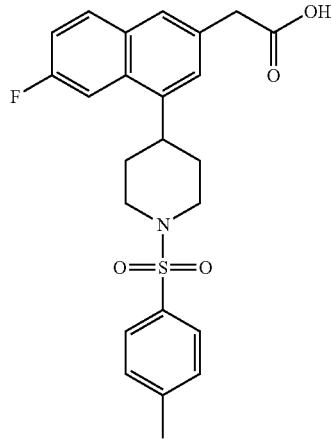 [SMILES: Cc1ccc(S(=O)(=O)N2CCC(c3cc(CC(=O)O)cc4ccc(F)cc34)CC2)cc1]

{6-Fluoro-4-[1-(toluene-4-sulfonyl)-piperidin-4-yl]-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. p-Toluenesulfonyl chloride (available from Sigma-Aldrich; 103 mg, 0.54 mmol) was added and the mixture was stirred at room temperature for 16 h. The solvent was evaporated under reduced pressure. Ethyl acetate was added and the mixture was washed with aqueous NaHCO₃ (5 mL) and water (5 mL). The organic layer was dried over Na₂SO₄, filtered, and evaporated under reduced pressure. The residue was purified by chromatography on silica gel using a Biotage purification system, eluting with 12% ethyl acetate/hexanes, to give {6-fluoro-4-[1-(toluene-4-sulfonyl)-piperidin-4-yl]-naphthalen-2-yl}-acetic acid methyl ester (76 mg, 46%) as a white solid. MS cald. for $C_{24}H_{25}FNO_4S$ [(M+H)⁺]: 456, obsd. 456.4.

{6-Fluoro-4-[1-(toluene-4-sulfonyl)-piperidin-4-yl]-naphthalen-2-yl}-acetic acid To a stirred solution of {6-fluoro-4-[1-(toluene-4-sulfonyl)-piperidin-4-yl]-naphthalen-2-yl}-acetic acid methyl ester (70 mg, 0.2 mmol) in THF (4 mL) was added a solution of lithium hydroxide monohydrate (32 mg, 0.76 mmol) in water (1 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na₂SO₄ and evaporated under reduced pressure to give [{6-fluoro-4-[1-(toluene-4-sulfonyl)-piperidin-4-yl]-naphthalen-2-yl}-acetic acid (52 mg, 77%) as an off-white solid. ¹H NMR (400 MHz, DMSO-d₆) δ ppm 12.37 (br s, 1H), 7.94 (dd, J=8.8, 6.4 Hz, 1H), 7.88 (d, J=10.3 Hz, 1H), 7.66-7.73 (m, 3H), 7.50 (d, J=8.3 Hz, 2H), 7.33-7.42 (m, 2H), 3.79 (d, J=12.2 Hz, 2H), 3.71 (s, 2H), 1.90 (d, J=11.7 Hz, 2H), 1.69-1.82 (m, 1H); MS cald. for $C_{24}H_{25}FNO_4S$ [(M–H)⁻]: 440, obsd. 440.4.

Example 3

{6-Fluoro-4-[1-(pyridine-2-sulfonyl)-piperidin-4-yl]-naphthalen-2-yl}-acetic acid

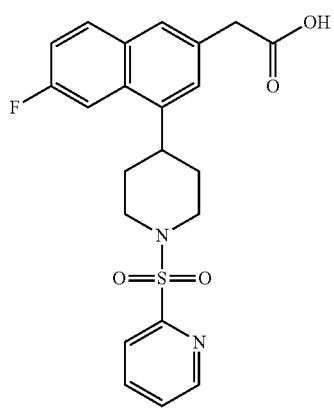 [SMILES: O=C(O)Cc1cc(C2CCN(S(=O)(=O)c3ccccn3)CC2)c2cc(F)ccc2c1]

Pyridine-2-sulfonyl chloride

2-Mercaptopyridine (available from Sigma-Aldrich; 0.25 g, 2.25 mmol) was added to H₂SO₄ (8 mL) and the mixture was cooled to about −5° C. Sodium hypochlorite (10% solution; 17 mL) was added and the reaction mixture was stirred for 30 min at about 0° C. Water (10 mL) was added and the mixture was extracted with CH₂Cl₂ (3×20 mL). The combined organic layers were dried over Na₂SO₄, filtered and evaporated under reduced pressure to give crude pyridine-2-sulfonyl chloride (0.23 g, 58%), which was used directly in the next step without further purification.

{6-Fluoro-4-[1-(pyridine-2-sulfonyl)-piperidin-4-yl]-naphthalen-2-yl}-acetic acid methyl ester Diisopropylethylamine (0.4 mL, 2.3 mmol) was added at 0° C. to a solution of (6-fluoro-4-piperidin-4-yl-naphthalen-2-yl)-acetic acid methyl ester trifluoroacetate salt (which may be prepared as described above; 100 mg, 0.24 mmol) in CH₂Cl₂ (6 mL). The solution was stirred at room temperature for 30 min and then a solution of pyridine-2-sulfonyl chloride (which may be prepared as described above; 213 mg, 1.2 mmol) in CH₂Cl₂ (1 mL) was added. The mixture was stirred at room temperature for 16 h. The solvent was evaporated under reduced pressure The residue was purified by chromatography on silica gel using a Biotage purification system, eluting with 25% ethyl acetate/hexanes, to give {6-fluoro-4-[1-(pyridine-2-sulfonyl)-piperidin-4-yl]-naphthalen-2-yl}-acetic acid methyl ester (32 mg, 30%) as a white solid. MS cald. for $C_{23}H_{24}FN_2O_4S$ [(M+H)⁺]: 443, obsd. 443.3.

{6-Fluoro-4-[1-(pyridine-2-sulfonyl)-piperidin-4-yl]-naphthalen-2-yl}-acetic acid To a stirred solution of {6-fluoro-4-[1-(pyridine-2-sulfonyl)-piperidin-4-yl]-naphthalen-2-yl}-acetic acid methyl ester (30 mg, 0.07 mmol) in THF (4 mL) was added a solution of lithium hydroxide monohydrate (14 mg, 0.33 mmol) in water (1 mL) and the reaction mixture was stirred for 24 hours at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over $Na_2SO_4$ and evaporated under reduced pressure to give {6-fluoro-4-[1-(pyridine-2-sulfonyl)-piperidin-4-yl]-naphthalen-2-yl}-acetic acid (20 mg, 69%) as a brown solid. $^1$H NMR (400 MHz, DMSO-$d_6$) δ ppm 12.38 (br s, 1H), 8.84 (d, J=3.9 Hz, 1H) 8.12-8.20 (m, 1H) 7.85-8.02 (m, 3H) 7.76 (dd, J=7.6, 4.6 Hz, 1H) 7.69 (s, 1H) 7.39 (t, J=8.6 Hz, 1H) 7.33 (s, 1H) 3.91 (d, J=11.7 Hz, 2H) 3.72 (s, 2H) 2.99 (t, J=11.7 Hz, 3H) 1.89 (d, J=12.7 Hz, 2H) 1.63-1.78 (m, 2H); MS calcd. for $C_{22}H_{22}FN_2O_4S$ [(M+H)$^+$]: 429, obsd. 429.2.

Example 4

{6-Fluoro-4-[1-(pyridine-3-sulfonyl)-piperidin-4-yl]-naphthalen-2-yl}-acetic acid

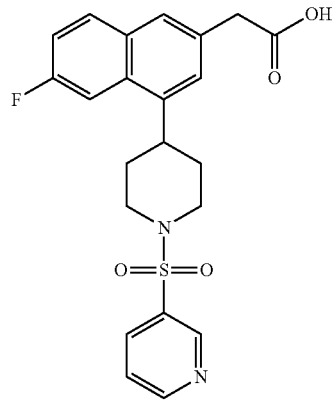 [SMILES: O=C(O)Cc1cc(C2CCN(S(=O)(=O)c3cccnc3)CC2)c2cc(F)ccc2c1]

Pyridine-3-sulfonyl chloride

Phosphorus pentachloride (1.57 g, 7.5 mmol) was added to a stirred solution of pyridine-3-sulfonic acid (1.00 g, 6.3 mmol) in toluene (5 mL). The mixture was heated at reflux for 16 hours and then cooled to room temperature. The mixture was filtered through celite, and the celite was washed with benzene (2×10 mL). The combined filtrates were concentrated under reduced pressure to give crude pyridine-3-sulfonyl chloride (0.70 g, 100%), which was used directly in the next step without further purification.

{6-Fluoro-4-[1-(pyridine-2-sulfonyl)-piperidin-4-yl]-naphthalen-2-yl}-acetic acid methyl ester Diisopropylethylamine (0.3 mL, 1.7 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in $CH_2Cl_2$ (6 mL). The solution was stirred at room temperature for 30 minutes and then a solution of pyridine-3-sulfonyl chloride (which may be prepared as described above; 320 mg, 1.8 mmol) in $CH_2Cl_2$ (1 mL) was added. The mixture was stirred at room temperature for 16 hours. The solvent was evaporated under reduced pressure. The residue was purified by chromatography on silica gel using a Biotage purification system, eluting with 30% ethyl acetate/hexanes, to give {6-fluoro-4-[1-(pyridine-3-sulfonyl)-piperidin-4-yl]-naphthalen-2-yl}-acetic acid methyl ester (85 mg, 53%) as a sticky white solid. MS calcd. for $C_{23}H_{24}FN_2O_4S$ [(M+H)$^+$]: 443, obsd. 443.2.

{6-Fluoro-4-[1-(pyridine-3-sulfonyl)-piperidin-4-yl]-naphthalen-2-yl}-acetic acid To a stirred solution of {6-fluoro-4-[1-(pyridine-3-sulfonyl)-piperidin-4-yl]-naphthalen-2-yl}-acetic acid methyl ester (85 mg, 0.19 mmol) in THF (6 mL) was added a solution of lithium hydroxide monohydrate (40 mg, 0.95 mmol) in water (1.5 mL) and the reaction mixture was stirred for 24 hours at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over $Na_2SO_4$ and evaporated under reduced pressure to give {6-fluoro-4-[1-(pyridine-3-sulfonyl)-piperidin-4-yl]-naphthalen-2-yl}-acetic acid (60 mg, 73%) as a white solid. $^1$H NMR (400 MHz, DMSO-$d_6$) δ ppm 12.38 (br s, 1H), 8.87-9.04 (m, 1H), 8.21 (d, J=7.1 Hz, 1H), 7.77-7.99 (m, 2H), 7.68 (br. s., 2H), 7.35 (br. s., 2H), 3.91 (d, J=11.6 Hz, 2H), 3.71 (s, 2H), 1.96 (d, J=12.1 Hz, 3H), 1.78 (d, J=11.6 Hz, 3H); MS calcd. for $C_{22}H_{22}FN_2O_4S$ [(M+H)$^+$]: 429, obsd. 429.2.

Example 5

{6-Fluoro-4-[1-(pyridine-4-sulfonyl)-piperidin-4-yl]-naphthalen-2-yl}-acetic acid

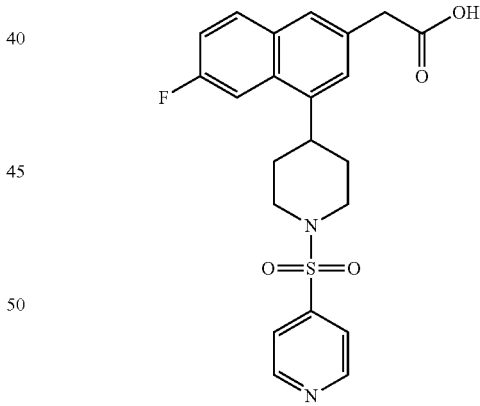

Pyridine-4-sulfonyl chloride

4-Mercaptopyridine (available from Sigma-Aldrich; 1.10 g, 1 mmol) was added to $H_2SO_4$ (7.5 mL) and the mixture was cooled to about −10° C. Chlorine gas was bubbled through the solution for 45 minutes, and then calcium carbonate (1.0 g) was added slowly. The reaction mixture was added to $CHCl_3$ (20 mL) and the mixture was cooled to −10° C. More calcium carbonate (7.0 g) was added in portions. The organic layer was decanted and the residue was washed with $CHCl_3$ (2×20 mL). The combined organic layers were dried over $Na_2SO_4$, filtered, and evaporated under reduced pressure to give crude pyridine-4-sulfonyl chloride which was used directly in the next step without further purification.

{6-Fluoro-4-[1-(pyridine-4-sulfonyl)-piperidin-4-yl]-naphthalen-2-yl}-acetic acid methyl ester Diisopropylethylamine (0.3 mL, 1.7 mmol) was added at 0° C. to a solution of (6-fluoro-4-piperidin-4-yl-naphthalen-2-yl)-acetic acid methyl ester trifluoroacetate salt (which may be prepared as described above; 100 mg, 0.24 mmol) in $CH_2Cl_2$ (6 mL). The solution was stirred at room temperature for 30 min and then a solution of pyridine-4-sulfonyl chloride (which may be prepared as described above; 213 mg, 1.2 mmol) in $CH_2Cl_2$ (1 mL) was added. The mixture was stirred at room temperature for 16 h. The solvent was evaporated under reduced pressure. The residue was purified by chromatography on silica gel to give {6-fluoro-4-[1-(pyridine-4-sulfonyl)-piperidin-4-yl]-naphthalen-2-yl}-acetic acid methyl ester (45 mg, 42%) as an orange liquid. MS calcd. for $C_{23}H_{24}FN_2O_4S$ [(M+H)$^+$]: 443, obsd. 443.4.

{6-Fluoro-4-[1-(pyridine-4-sulfonyl)-piperidin-4-yl]-naphthalen-2-yl}-acetic acid To a stirred solution of {6-fluoro-4-[1-(pyridine-4-sulfonyl)-piperidin-4-yl]-naphthalen-2-yl}-acetic acid methyl ester (which may be prepared as described above; 44.5 mg, 0.1 mmol) in THF (4 mL) was added a solution of lithium hydroxide monohydrate (20 mg, 0.48 mmol) in water (1 mL) and the reaction mixture was stirred for 24 hours at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over $Na_2SO_4$ and evaporated under reduced pressure to give {6-fluoro-4-[1-(pyridine-4-sulfonyl)-piperidin-4-yl]-naphthalen-2-yl}-acetic acid (12 mg) as a yellow solid. LCMS analysis indicated that the purity of this material was 42%. MS calcd. for $C_{22}H_{22}FN_2O_4S$ [(M+H)$^+$]: 429, obsd. 429.2.

2-yl)-acetic acid methyl ester trifluoroacetate salt (which may be prepared as described above; 150 mg, 0.36 mmol) in tetrahydrofuran (5 mL), and the mixture was stirred at room temperature for 30 min. 2-Chlorobenzenesulfonyl chloride (available from Sigma-Aldrich; 114 mg, 0.54 mmol) was added and the mixture was stirred at room temperature for 16 h. The solvent was evaporated under reduced pressure. Ethyl acetate was added and the mixture was washed with aqueous $NaHCO_3$ (5 mL) and water (5 mL). The organic layer was dried over $Na_2SO_4$, filtered, and evaporated under reduced pressure. The residue was purified by chromatography on silica gel using a Biotage purification system, eluting with 10% ethyl acetate/hexanes, to give {4-[1-(2-chloro-benzenesulfonyl)-piperidin-4-yl]-6-fluoro-naphthalen-2-yl}-acetic acid methyl ester (94 mg, 55%) as a white solid. MS calcd. for $C_{24}H_{24}ClFNO_4S$ [(M+H)$^+$]: 476, obsd. 476.2.

{4-[1-(2-Chloro-benzenesulfonyl)-piperidin-4-yl]-6-fluoro-naphthalen-2-yl}-acetic acid To a stirred solution of {4-[1-(2-chloro-benzenesulfonyl)-piperidin-4-yl]-6-fluoro-naphthalen-2-yl}-acetic acid methyl ester (90 mg, 0.19 mmol) in THF (4 mL) was added a solution of lithium hydroxide monohydrate (40 mg, 0.95 mmol) in water (1 mL) and the reaction mixture was stirred for 24 h at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over $Na_2SO_4$ and evaporated under reduced pressure to give {4-[1-(2-chloro-benzenesulfonyl)-piperidin-4-yl]-6-fluoro-naphthalen-2-yl}-acetic acid (40 mg, 46%) as an off-white solid. $^1$H NMR (400 MHz, DMSO-d$_6$) δ ppm 12.36 (br. s., 1H), 8.03 (d, J=7.8 Hz, 1H), 7.88-7.99 (m, 2H), 7.67-7.79 (m, 3H), 7.61 (t, J=8.8 Hz, 1H), 7.40 (dt, J=8.7, 1.7 Hz, 1H), 7.35 (s, 1H), 3.88 (d, J=12.2 Hz, 2H), 3.72 (s, 2H), 3.46 (t, J=11.7 Hz, 1H), 3.04 (t, J=11.7 Hz, 2H), 1.88-1.96 (m, 2H), 1.64-1.79 (m, 2H); MS calcd. for $C_{23}H_{22}ClFNO_4S$ [(M−H)$^-$]: 462, obsd. 462.2.

Example 6

{4-[1-(2-Chloro-benzenesulfonyl)-piperidin-4-yl]-6-fluoro-naphthalen-2-yl}-acetic acid

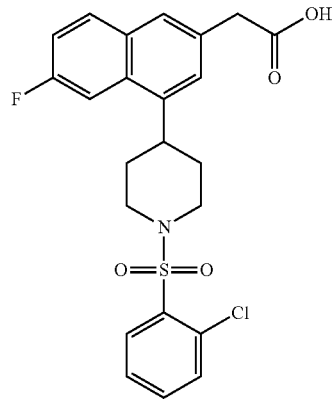 [SMILES: O=C(O)Cc1cc(C2CCN(S(=O)(=O)c3ccccc3Cl)CC2)c2cc(F)ccc2c1]

{4-[1-(2-Chloro-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen- Example 7

{4-[1-(3-Chloro-benzenesulfonyl)-piperidin-4-yl]-6-fluoro-naphthalen-2-yl}-acetic acid

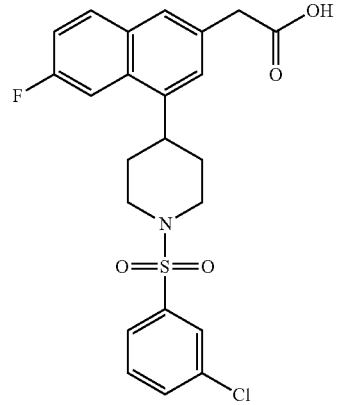 [SMILES: O=C(O)Cc1cc(C2CCN(S(=O)(=O)c3cccc(Cl)c3)CC2)c2cc(F)ccc2c1]

{4-[1-(3-Chloro-benzenesulfonyl)-piperidin-4-yl]-6-fluoro-naphthalen-2-yl}-acetic acid methyl ester Diisopropylethylamine (0.3 mL, 1.7 mmol) was added at 0° C. to a solution of (6-fluoro-4-piperidin-4-yl-naphthalen- 2-yl)-acetic acid methyl ester trifluoroacetate salt (which may be prepared as described above; 150 mg, 0.36 mmol) in tetrahydrofuran (5 mL), and the mixture was stirred at room temperature for 30 min. 3-Chlorobenzenesulfonyl chloride (available from Sigma-Aldrich; 110 mg, 0.52 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(3-chloro-benzenesulfonyl)-piperidin-4-yl]-6-fluoro-naphthalen-2-yl}-acetic acid methyl ester (97 mg, 56%) as a white solid. MS cald. for C$_{24}$H$_{24}$ClFNO$_4$S [(M+H)$^+$]: 476, obsd. 476.4.

{4-[1-(3-Chloro-benzenesulfonyl)-piperidin-4-yl]-6-fluoro-naphthalen-2-yl}-acetic acid To a stirred solution of {4-[1-(3-chloro-benzenesulfonyl)-piperidin-4-yl]-6-fluoro-naphthalen-2-yl}-acetic acid methyl ester (90 mg, 0.19 mmol) in THF (4 mL) was added a solution of lithium hydroxide monohydrate (40 mg, 0.95 mmol) in water (1 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(3-chloro-benzenesulfonyl)-piperidin-4-yl]-6-fluoro-naphthalen-2-yl}-acetic acid (57 mg, 65%) as an off-white solid. $^1$H NMR (400 MHz, DMSO-d$_6$) δ ppm 12.34 (br. s., 1H), 7.95 (dd, J=9.0, 6.1 Hz, 1H), 7.84-7.92 (m, 2H), 7.71-7.83 (m, 3H), 7.69 (s, 1H), 7.34-7.42 (m, 2H), 3.83 (d, J=11.2 Hz, 2H), 3.27-3.34 (m, 7H), 2.63 (t, J=11.2 Hz, 2H), 1.88-1.96 (m, 2H), 1.69-1.83 (m, 2H); MS cald. for C$_{23}$H$_{22}$ClFNO$_4$S [(M−H)$^+$]: 462, obsd. 462.2.

Example 8

{4-[1-(4-Chloro-benzenesulfonyl)-piperidin-4-yl]-6-fluoro-naphthalen-2-yl}-acetic acid

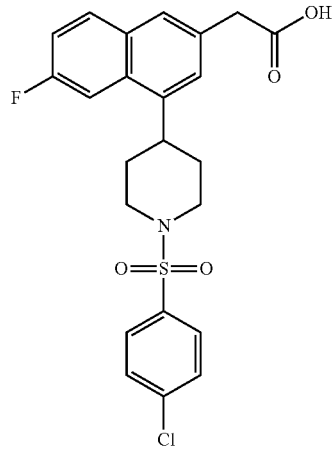 [SMILES: O=C(O)Cc1cc(C2CCN(S(=O)(=O)c3ccc(Cl)cc3)CC2)c2cc(F)ccc2c1]

{4-[1-(4-Chloro-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 4-Chlorobenzenesulfonyl chloride (available from Sigma-Aldrich; 114 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(4-chloro-benzenesulfonyl)-piperidin-4-yl]-6-fluoro-naphthalen-2-yl}-acetic acid methyl ester (86 mg, 50%) as a white solid. MS cald. for C$_{24}$H$_{24}$ClFNO$_4$S [(M+H)$^+$]: 476, obsd. 476.4.

{4-[1-(4-Chloro-benzenesulfonyl)-piperidin-4-yl]-6-fluoro-naphthalen-2-yl}-acetic acid To a stirred solution of {4-[1-(4-chloro-benzenesulfonyl)-piperidin-4-yl]-6-fluoro-naphthalen-2-yl}-acetic acid methyl ester (80 mg, 0.17 mmol) in THF (4 mL) was added a solution of lithium hydroxide monohydrate (35 mg, 0.83 mmol) in water (1 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(4-chloro-benzenesulfonyl)-piperidin-4-yl]-6-fluoro-naphthalen-2-yl}-acetic acid (57 mg, 65%) as an off-white solid. $^1$H NMR (400 MHz, DMSO-d$_6$) δ ppm 12.27 (br s, 1H), 7.95 (dd, J=9.0, 6.1 Hz, 1H), 7.88 (d, J=10.3 Hz, 1H), 7.76-7.85 (m, 4H), 7.68 (s, 1H), 7.34-7.41 (m, 2H), 3.80 (d, J=11.2 Hz, 2H), 3.71 (s, 2H), 2.59 (t, J=11.2 Hz, 2H), 1.87-1.94 (m, 3H), 1.73-1.82 (m, 2H); MS cald. for C$_{23}$H$_{20}$ClFNO$_4$S [(M−H)$^-$]: 460, obsd. 460.3.

Example 9

{6-Fluoro-4-[1-(3-methanesulfonyl-benzenesulfonyl)-piperidin-4-yl]-naphthalen-2-yl}-acetic acid

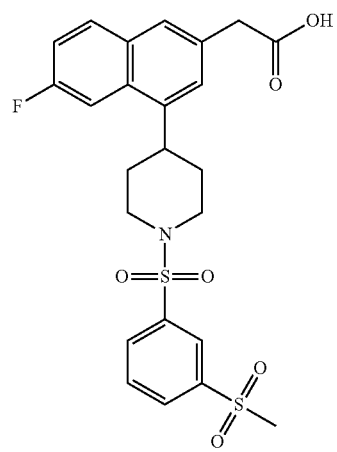 [SMILES: CS(=O)(=O)c1cccc(S(=O)(=O)N2CCC(c3cc(CC(=O)O)cc4ccc(F)cc34)CC2)c1]

{6-Fluoro-4-[1-(3-methanesulfonyl-benzenesulfonyl)-piperidin-4-yl]-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 3-Methylsulfonylbenzenesulfonyl chloride (available from Matrix Scientific; 138 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 20% ethyl acetate/hexanes, to give {6-fluoro-4-[1-(3-methanesulfonyl-benzenesulfonyl)-piperidin-4-yl]-naphthalen-2-yl}-acetic acid methyl ester (120 mg, 64%) as an off-white solid. MS calcd. for C$_{25}$H$_{27}$FNO$_6$S$_2$ [(M+H)$^+$]: 520, obsd. 520.2.

{6-Fluoro-4-[1-(3-methanesulfonyl-benzenesulfonyl)-piperidin-4-yl]-naphthalen-2-yl}-acetic acid To a stirred solution of {6-fluoro-4-[1-(3-methanesulfonyl-benzenesulfonyl)-piperidin-4-yl]-naphthalen-2-yl}-acetic acid methyl ester (115 mg, 0.22 mmol) in THF (6 mL) was added a solution of lithium hydroxide monohydrate (46 mg, 1.1 mmol) in water (1.5 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {6-fluoro-4-[1-(3-methanesulfonyl-benzenesulfonyl)-piperidin-4-yl]-naphthalen-2-yl}-acetic acid (90 mg, 80%) as an off-white solid. $^1$H NMR (400 MHz, DMSO-d$_6$) δ ppm 12.35 (br s, 1H), 8.34 (d, J=7.8 Hz, 1H), 8.23 (s, 1H), 8.18 (d, J=7.8 Hz, 1H), 7.98-8.04 (m, 1H), 7.95 (dd, J=9.3, 6.4 Hz, 1H), 7.86 (d, J=12.7 Hz, 1H), 7.69 (s, 1H), 7.35-7.41 (m, 2H), 3.87 (d, J=10.3 Hz, 2H), 3.71 (s, 2H), 3.39 (s, 3H), 2.66 (d, J=10.3 Hz, 2H), 1.89-1.96 (m, 2H), 1.73-1.83 (m, 1H); MS calcd. for C$_{24}$H$_{25}$FNO$_6$S$_2$ [(M−H)$^-$]: 506, obsd. 506.2.

Example 10

{4-[1-(2,5-Dichloro-benzenesulfonyl)-piperidin-4-yl]-6-fluoro-naphthalen-2-yl}-acetic acid

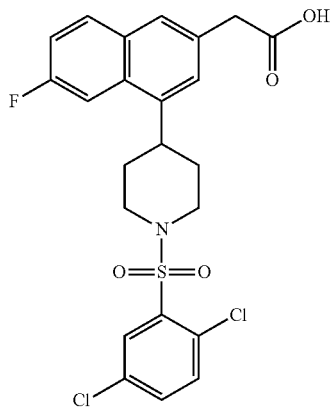 [SMILES: O=C(O)Cc1cc(C2CCN(S(=O)(=O)c3cc(Cl)ccc3Cl)CC2)c2cc(F)ccc2c1]

{4-[1-(2,5-Dichloro-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 2,5-Dichlorobenzenesulfonyl chloride (available from Sigma-Aldrich; 133 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(2,5-dichloro-benzenesulfonyl)-piperidin-4-yl]-6-fluoro-naphthalen-2-yl}-acetic acid methyl ester (126 mg, 68%) as a sticky off-white solid. MS calcd. for C$_{24}$H$_{23}$Cl$_2$FNO$_4$S [(M+H)$^+$]: 510, obsd. 510.2.

{4-[1-(2,5-Dichloro-benzenesulfonyl)-piperidin-4-yl]-6-fluoro-naphthalen-2-yl}-acetic acid To a stirred solution of {4-[1-(2,5-dichloro-benzenesulfonyl)-piperidin-4-yl]-6-fluoro-naphthalen-2-yl}-acetic acid methyl ester (120 mg, 0.24 mmol) in THF (6 mL) was added a solution of lithium hydroxide monohydrate (50 mg, 1.2 mmol) in water (1.5 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(2,5-dichloro-benzenesulfonyl)-piperidin-4-yl]-6-fluoro-naphthalen-2-yl}-acetic acid (105 mg, 90%) as an off-white solid. $^1$H NMR (400 MHz, DMSO-d$_6$) δ ppm 12.38 (br s, 1H), 7.96-8.01 (m, 2H), 7.94 (d, J=4.4 Hz, 1H), 7.80-7.83 (m, 2H), 7.69 (s, 1H), 7.41 (t, J=8.8 Hz, 1H), 7.36 (s, 1H), 3.91 (d, J=12.2 Hz, 2H), 3.72 (s, 2H), 3.08 (t, J=11.5 Hz, 2H), 1.90-1.96 (m, 2H), 1.67-1.77 (m, 2H); MS calcd. for C$_{23}$H$_{19}$Cl$_2$FNO$_4$S [(M−H)$^-$]: 494, obsd. 494.3.

Example 11

{4-[1-(2,4-Dichloro-benzenesulfonyl)-piperidin-4-yl]-6-fluoro-naphthalen-2-yl}-acetic acid

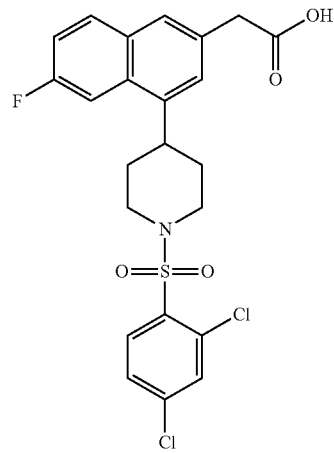 [SMILES: O=C(O)Cc1cc(C2CCN(S(=O)(=O)c3ccc(Cl)cc3Cl)CC2)c2cc(F)ccc2c1]

{4-[1-(2,4-Dichloro-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 2,4-Dichlorobenzenesulfonyl chloride (available from Sigma-Aldrich; 133 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(2,4-dichloro-benzenesulfonyl)-piperidin-4-yl]-6-fluoro-naphthalen-2-yl}-acetic acid methyl ester (120 mg, 65%) as a sticky off-white solid. MS cald. for C$_{24}$H$_{23}$Cl$_2$FNO$_4$S [(M+H)$^+$]: 510, obsd. 510.2.

{4-[1-(2,4-Dichloro-benzenesulfonyl)-piperidin-4-yl]-6-fluoro-naphthalen-2-yl}-acetic acid To a stirred solution of {4-[1-(2,4-dichloro-benzenesulfonyl)-piperidin-4-yl]-6-fluoro-naphthalen-2-yl}-acetic acid methyl ester (115 mg, 0.23 mmol) in THF (6 mL) was added a solution of lithium hydroxide monohydrate (50 mg, 1.2 mmol) in water (1.5 mL) and the reaction mixture was stirred for 24 h at RT. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(2,4-dichloro-benzenesulfonyl)-piperidin-4-yl]-6-fluoro-naphthalen-2-yl}-acetic acid (100 mg, 89%) as an off-white solid. $^1$H NMR (400 MHz, DMSO-d$_6$) δ ppm 12.35 (br s, 1H), 8.02 (d, J=8.3 Hz, 1H), 7.96-8.00 (m, 2H), 7.87-7.95 (m, 1H), 7.68-7.73 (m, 2H), 7.34-7.44 (m, 2H), 3.87 (d, J=12.2 Hz, 2H), 3.72 (s, 2H), 3.04 (t, J=11.5 Hz, 2H), 1.89-1.96 (m, 2H), 1.67-1.78 (m, 2H); MS cald. for C$_{23}$H$_{19}$Cl$_2$FNO$_4$S [(M−H)$^-$]: 494, obsd. 494.3.

Example 12

{4-[1-(3,5-Dichloro-benzenesulfonyl)-piperidin-4-yl]-6-fluoro-naphthalen-2-yl}-acetic acid

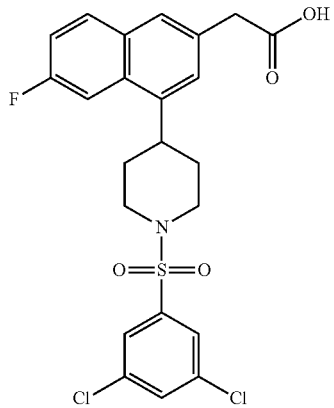 [SMILES: O=C(O)Cc1cc(C2CCN(S(=O)(=O)c3cc(Cl)cc(Cl)c3)CC2)c2cc(F)ccc2c1]

{4-[1-(3,5-Dichloro-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 3,5-Dichlorobenzenesulfonyl chloride (available from Sigma-Aldrich; 133 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(3,5-dichloro-benzenesulfonyl)-piperidin-4-yl]-6-fluoro-naphthalen-2-yl}-acetic acid methyl ester (78 mg, 42%) as a sticky off-white solid. MS cald. for C$_{24}$H$_{23}$Cl$_2$FNO$_4$S [(M+H)$^+$]: 510, obsd. 510.2.

{4-[1-(3,5-Dichloro-benzenesulfonyl)-piperidin-4-yl]-6-fluoro-naphthalen-2-yl}-acetic acid To a stirred solution of {4-[1-(3,5-dichloro-benzenesulfonyl)-piperidin-4-yl]-6-fluoro-naphthalen-2-yl}-acetic acid methyl ester (75 mg, 0.15 mmol) in THF (6 mL) was added a solution of lithium hydroxide monohydrate (30 mg, 0.7 mmol) in water (1.5 mL) and the reaction mixture was stirred for 24 hours at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(3,5-dichloro-benzenesulfonyl)-piperidin-4-yl]-6-fluoro-naphthalen-2-yl}-acetic acid (60 mg, 82%) as an off-white solid. $^1$H NMR (400 MHz, DMSO-d$_6$) δ ppm 12.35 (br s, 1H), 8.10 (s, 1H), 7.86-8.01 (m, 2H), 7.82 (s, 2H), 7.69 (s, 1H), 7.31-7.44 (m, 2H), 3.85 (d, J=12.2 Hz, 2H), 3.72 (s, 2H), 2.62-2.73 (m, 3H), 1.93 (d, J=12.2 Hz, 2H), 1.69-1.83 (m, 2H); MS cald. for C$_{23}$H$_{19}$Cl$_2$FNO$_4$S [(M−H)$^-$]: 494, obsd. 494.2.

Example 13

{4-[1-(3,5-Bis-trifluoromethyl-benzenesulfonyl)-piperidin-4-yl]-6-fluoro-naphthalen-2-yl}-acetic acid

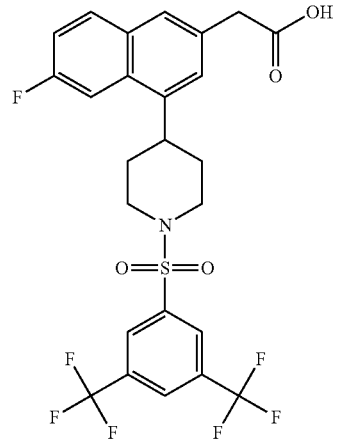 [SMILES: O=C(O)Cc1cc(C2CCN(S(=O)(=O)c3cc(C(F)(F)F)cc(C(F)(F)F)c3)CC2)c2cc(F)ccc2c1]

{4-[1-(3,5-Bis-trifluoromethyl-benzenesulfonyl)-piperidin-4-yl]-6-fluoro-naphthalen-2-yl}-acetic acid methyl ester Diisopropylethylamine (0.6 mL, 3.4 mmol) was added at 0° C. to a solution of (6-fluoro-4-piperidin-4-yl-naphthalen-2-yl)-acetic acid methyl ester trifluoroacetate salt (which may be prepared as described above; 150 mg, 0.36 mmol) in tetrahydrofuran (5 mL), and the mixture was stirred at room temperature for 30 min. 3,5-Bis(trifluoromethyl)benzenesulfonyl chloride (available from Sigma-Aldrich; 169 mg, 0.54 mmol) was added and the mixture was stirred at room temperature for 16 h. The solvent was evaporated under reduced pressure. Ethyl acetate was added and the mixture was washed with aqueous NaHCO$_3$ (5 mL) and water (5 mL). The organic layer was dried over Na$_2$SO$_4$, filtered, and evaporated under reduced pressure. The residue was purified by chromatography on silica gel using a Biotage purification system, eluting with 10% ethyl acetate/hexanes, to give {4-[1-(3,5-bis-trifluoromethyl-benzenesulfonyl)-piperidin-4-yl]-6-fluoro-naphthalen-2-yl}-acetic acid methyl ester (87 mg, 42%) as an off-white solid. MS cald. for C$_{26}$H$_{23}$F$_7$NO$_4$S [(M+H)$^+$]: 578, obsd. 578.4.

{4-[1-(3,5-Bis-trifluoromethyl-benzenesulfonyl)-piperidin-4-yl]-6-fluoro-naphthalen-2-yl}-acetic acid To a stirred solution of {4-[1-(3,5-bis-trifluoromethyl-benzenesulfonyl)-piperidin-4-yl]-6-fluoro-naphthalen-2-yl}-acetic acid methyl ester (80 mg, 0.14 mmol) in THF (4 mL) was added a solution of lithium hydroxide monohydrate (30 mg, 0.7 mmol) in water (1 mL) and the reaction mixture was stirred for 24 hours at room temperature. The reaction mixture was concentrated under reduced pressure and washed with diethyl ether (3×5 mL). The washings were discarded. Water (5 mL) was added to the residue, and the mixture acidified (pH ~2-3) with an aqueous solution of hydrochloric acid (2 N) and extracted with ethyl acetate (3×5 mL). The combined organic extracts were dried over Na$_2$SO$_4$ and evaporated under reduced pressure to give {4-[1-(3,5-bis-trifluoromethyl-benzenesulfonyl)-piperidin-4-yl]-6-fluoro-naphthalen-2-yl}-acetic acid (65 mg, 83%) as an off-white solid. $^1$H NMR (400 MHz, DMSO-d$_6$) δ ppm 12.33 (br s, 1H), 8.64 (s, 1H), 8.38 (s, 2H), 7.91-8.01 (m, 1H), 7.84 (d, J=12.7 Hz, 1H), 7.69 (s, 1H), 7.31-7.44 (m, 2H), 3.94 (d, J=11.7 Hz, 2H), 3.71 (s, 2H), 2.68 (d, J=11.2 Hz, 2H), 1.88-1.98 (m, 2H), 1.77 (d, J=8.3 Hz, 2H); MS cald. for C$_{25}$H$_{21}$F$_7$NO$_4$S [(M+H)$^+$]: 564, obsd. 564.0.

Example 14

{4-[1-(2-Chloro-benzenesulfonyl)-piperidin-4-yl]-6-fluoro-3-methyl-naphthalen-2-yl}-acetic acid

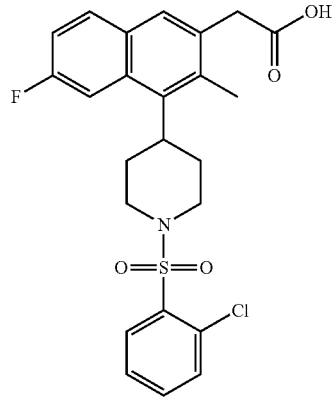 [SMILES: Cc1c(CC(=O)O)cc2ccc(F)cc2c1C1CCN(S(=O)(=O)c2ccccc2Cl)CC1]

{4-[1-(2-Chloro-benzenesulfonyl)-piperidin-4-yl]-6-fluoro-3-methyl-naphthalen-2-yl}-acetic acid methyl ester To a solution of (6-fluoro-3-methyl-4-piperidin-4-yl-naphthalen-2-yl)-acetic acid methyl ester (which may be prepared as described above; 108 mg, 0.34 mmol) and 2-chlorobenzenesulfonyl chloride (145 mg, 0.69 mmol) in THF (6 mL) was added excess N,N-diisopropylethylamine (179 μL, 1.0 mmol) at 0° C. under a nitrogen atmosphere. The resulting light brown solution was allowed to warm slowly to room temperature over 2 hours, was and then stirred for 15 hours at room temperature under a nitrogen atmosphere. The reaction mixture was diluted with water and brine solution and the organic compound was extracted with ethyl acetate (2×50 mL). The combined extracts were washed with brine solution and dried over anhydrous magnesium sulfate. Filtration and concentration gave a crude brown oil which was purified by flash chromatography (40 g ISCO column, eluting with 0-60% ethyl acetate/hexanes) to give {4-[1-(2-chloro-benzenesulfonyl)-piperidin-4-yl]-6-fluoro-3-methyl-naphthalen-2-yl}-acetic acid methyl ester (110 mg, 65%) as an off-white solid. MS cald. for C$_{25}$H$_{26}$ClFNO$_4$S [(M+H)$^+$] 490, obsd. 490.0.

{4-[1-(2-Chloro-benzenesulfonyl)-piperidin-4-yl]-6-fluoro-3-methyl-naphthalen-2-yl}-acetic acid To a clear, almost colorless solution of {4-[1-(2-chloro-benzenesulfonyl)-piperidin-4-yl]-6-fluoro-3-methyl-naphthalen-2-yl}-acetic acid methyl ester (108 mg, 0.23 mmol) in THF (8.0 mL) was added a solution of lithium hydroxide monohydrate (106 mg, 4.4 mmol) in water (2.0 mL) The mixture was heated with a heat gun to give a clear solution. The resulting solution was stirred for 15 hours at room temperature. The solvent was removed under vacuum. The residue was diluted with water (~20 mL) and the mixture was neutralized with 1.0 N HCl. The precipitated white solids were collected by filtration and washed with water and hexanes. After air drying, {4-[1-(2-chloro-benzenesulfonyl)-piperidin-4-yl]-6-fluoro-3-methyl-naphthalen-2-yl}-acetic acid (93 mg, 87%) was isolated as a white solid. $^1$H NMR (400 MHz, DMSO-d$_6$) δ ppm 12.42 (br. s, 1H), 8.07 (d, J=7.53 Hz, 2H), 783-7.96 (m, 1H), 7.65-7.82 (m, 3H), 7.56-7.64 (m, 1H), 7.28-7.40 (m, 1H), 3.91 (d, J=11.29 Hz, 4H), 3.76 (br. s, 3H), 3.05 (br. s, 2H), 2.36 (s, 3H), 1.68 (d, J=12.3 Hz, 2H). MS cald. for C$_{24}$H$_{24}$ClFNO$_4$S [(M+H)$^+$] 476, obsd. 476.1.

Example 15

[6-Fluoro-4-(1-methanesulfonyl-piperidin-4-yl)-3-methyl-naphthalen-2-yl]-acetic acid

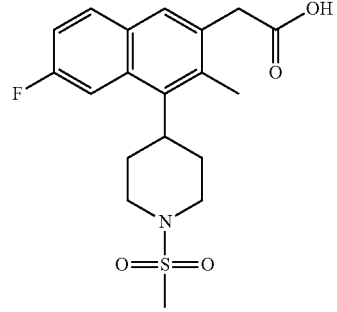 [SMILES: Cc1c(CC(=O)O)cc2ccc(F)cc2c1C1CCN(S(C)(=O)=O)CC1]

[6-Fluoro-4-(1-methanesulfonyl-piperidin-4-yl)-3-methyl-naphthalen-2-yl]-acetic acid methyl ester To a solution of (6-fluoro-3-methyl-4-piperidin-4-yl-naphthalen-2-yl)-acetic acid methyl ester (which may be prepared as described above; 82 mg, 0.26 mmol) and methanesulfonyl chloride (59.6 mg, 0.52 mmol) in THF (6.0 mL) was added N,N-diisopropylethylamine (227 µL, 1.3 mmol) at 0° C. under a nitrogen atmosphere. The resulting suspension was allowed to warm to room temperature during a period of 2 hours and then stirred for 15 hours under a nitrogen atmosphere. The reaction mixture was diluted with water and brine solution, and the organic compound was extracted with ethyl acetate (2×75 mL). The combined organic extracts were washed with brine solution and dried over anhydrous $MgSO_4$, filtered, and concentrated to give a crude brown oil which was purified by flash chromatography (40 g ISCO column, eluting with 0-100% ethyl acetate/hexanes) to give [6-fluoro-4-(1-methanesulfonyl-piperidin-4-yl)-3-methyl-naphthalen-2-yl]-acetic acid methyl ester (56 mg, 55%) as an off-white solid. MS cald. for $C_{20}H_{25}FNO_4S$ [(M+H)$^+$] 394, obsd. 393.9.

[6-Fluoro-4-(1-methanesulfonyl-piperidin-4-yl)-3-methyl-naphthalen-2-yl]-acetic acid To a solution of [6-fluoro-4-(1-methanesulfonyl-piperidin-4-yl)-3-methyl-naphthalen-2-yl]-acetic acid methyl ester (51 mg, 0.13 mmol) in THF (6.0 mL) was added a solution of lithium hydroxide monohydrate (62.1 mg, 2.6 mmol) in water (1.5 mL). The resulting solution was stirred for 15 hours at room temperature. The solvent was removed under vacuum. The residue was diluted with water (~20 mL) and neutralized with 1.0 N aqueous HCl to form a suspension. The product was extracted into ethyl acetate (2×50 mL). The combined extracts were washed with brine, dried over anhydrous $MgSO_4$, filtered, and concentrated to give a crude solid which was triturated with dichloromethane and hexanes. The solids were collected by filtration and washed with hexanes. After air drying, [6-fluoro-4-(1-methanesulfonyl-piperidin-4-yl)-3-methyl-naphthalen-2-yl]-acetic acid (48 mg, 94%) was obtained as a white solid. $^1$H NMR (400 MHz, DMSO-$d_6$) δ ppm 12.4 (br. s, 1H), 7.91 (dd, J=8.91, 6.65 Hz, 2H), 7.70 (s, 1H), 7.36 (t, J=8.41 Hz, 1H), 3.78 (br. s, 6H), 2.95 (s, 3H), 2.26-2.47 (m, 6H), 1.75 (d, J=12.05 Hz, 2H). MS cald. for $C_{19}H_{23}FNO_4S$ [(M+H)$^+$] 380, obsd. 380.0.

Example 16

{4-[1-(2,4-Dichloro-benzenesulfonyl)-piperidin-4-yl]-6-fluoro-3-methyl-naphthalen-2-yl}-acetic acid

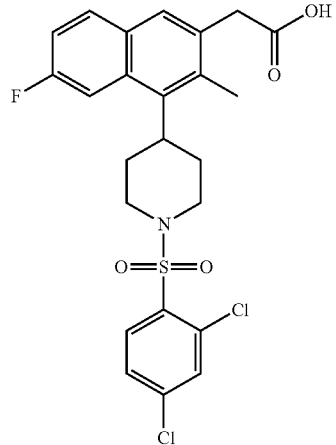 [SMILES: Cc1c(CC(=O)O)cc2ccc(F)cc2c1C1CCN(S(=O)(=O)c2ccc(Cl)cc2Cl)CC1]

{4-[1-(2,4-Dichloro-benzenesulfonyl)-piperidin-4-yl]-6-fluoro-3-methyl-naphthalen-2-yl}-acetic acid methyl ester To a 0° C. solution of (6-fluoro-3-methyl-4-piperidin-4-yl-naphthalen-2-yl)-acetic acid methyl ester (which may be prepared as described above; 110 mg, 0.35 mmol) and 2,4-dichlorobenzenesulfonyl chloride (171 mg, 0.7 mmol) in THF (6.0 mL) was added N,N-diisopropylethylamine (183 µL, 1.05 mmol). The resulting light yellow solution was allowed to warm to room temperature during 2 hours and then it was stirred for 15 hours at room temperature under nitrogen. The reaction mixture was diluted with water and brine solution and the organic compound was extracted into ethyl acetate (2×50 mL). The combined extracts were washed with brine solution and dried over $MgSO_4$. Filtration and concentration gave the crude product which was purified by flash chromatography (40 g ISCO column, eluting with 0-60% ethyl acetate in hexanes) to give {4-[1-(2,4-dichloro-benzenesulfonyl)-piperidin-4-yl]-6-fluoro-3-methyl-naphthalen-2-yl}-acetic acid methyl ester (119 mg, 65%) as an off-white solid. MS cald. for $C_{20}H_{25}FNO_4S$ [(M+H)$^+$] 524, obsd. 523.8.

{4-[1-(2,4-Dichloro-benzenesulfonyl)-piperidin-4-yl]-6-fluoro-3-methyl-naphthalen-2-yl}-acetic acid To a colorless solution of {4-[1-(2,4-dichloro-benzenesulfonyl)-piperidin-4-yl]-6-fluoro-3-methyl-naphthalen-2-yl}-acetic acid methyl ester (109 mg, 0.208 mmol) in THF (8.0 mL) was added a solution of an excess lithium hydroxide (100 mg, 4.18 mmol) in water (2.0 mL) at room temperature. The resulting light yellow solution was stirred for 15 hours. The reaction mixture was concentrated and the aqueous solution was diluted with water then neutralized with 1.0 N aqueous HCl. The resulting suspension was extracted into ethyl acetate (2×40 mL). The combined extracts were washed with brine and dried over anhydrous $MgSO_4$, filtered, and concentrated to afford {4-[1-(2,4-dichloro-benzenesulfonyl)-piperidin-4-yl]-6-fluoro-3-methyl-naphthalen-2-yl}-acetic acid (105 mg, 99%) as a light yellow solid. $^1$H NMR (400 MHz, DMSO-$d_6$) δ ppm 12.32 (br. s, 1H), 8.06 (d, J=8.5 Hz, 1H), 7.98 (d, J=2.0 Hz, 1H), 7.88 (dd, J=8.5, 6.8 Hz, 1H), 7.64-7.82 (m, 3H), 7.25-7.39 (m, 1H), 3.82-3.94 (m, 2H), 3.76 (br. s, 2H), 3.47-3.72 (m, 1H), 3.07 (br. s, 2H), 2.36 (s, 3H), 2.09-2.46 (m, 2H), 1.68 (d, J=12.0 Hz, 2H). MS cald. for $C_{24}H_{23}Cl_2FNO_4S$ [(M+H)$^+$] 510, obsd. 510.1.

Example 17

{4-[1-(2,5-Dichloro-benzenesulfonyl)-piperidin-4-yl]-6-fluoro-3-methyl-naphthalen-2-yl}-acetic acid

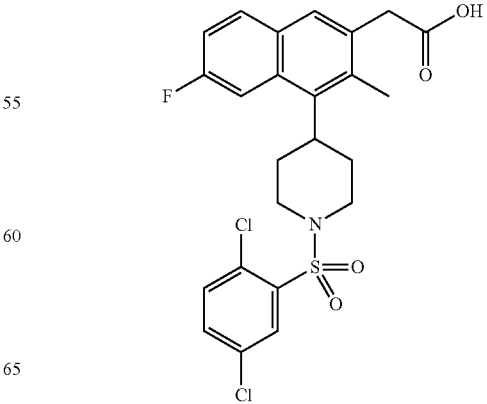

{4-[1-(2,5-Dichloro-benzenesulfonyl)-piperidin-4-yl]-6-fluoro-3-methyl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 μL, 0.711 mmol) in methylene chloride (6.0 mL) was added 2,5-dichlorobenzenesulfonyl chloride (116 mg, 0.474 mmol). After stirring for ~15 minutes at 0° C., the light yellow reaction mixture was allowed to warm to room temperature and then was stirred overnight at room temperature under nitrogen. During this time, some solvent evaporated. Methylene chloride (~10 mL) and water (~25 mL) were added. The resulting mixture was extracted with methylene chloride (2×25 mL). The combined extracts were washed with brine solution then concentrated to give the crude product which was purified by elution from a silica gel plug (20% ethyl acetate in hexanes) to give {4-[1-(2,5-dichloro-benzenesulfonyl)-piperidin-4-yl]-6-fluoro-3-methyl-naphthalen-2-yl}-acetic acid methyl ester (52 mg, 42%) as an off-white solid. MS calcd. for $C_{25}H_{25}Cl_2FNO_4S$ [(M+H)$^+$]: 524, obsd. 524.0.

{4-[1-(2,5-Dichloro-benzenesulfonyl)-piperidin-4-yl]-6-fluoro-3-methyl-naphthalen-2-yl}-acetic acid To a solution of {4-[1-(2,5-dichloro-benzenesulfonyl)-piperidin-4-yl]-6-fluoro-3-methyl-naphthalen-2-yl}-acetic acid methyl ester (52 mg, 0.099 mmol) in THF (8.0 mL) was added a solution of lithium hydroxide monohydrate (42.4 mg, 1.0 mmol) in water (2 mL). The reaction mixture was stirred at room temperature overnight under nitrogen. After this time, the reaction mixture was diluted with water (~20 mL) and then acidified with 1.0 N aqueous HCl (2 mL). The resulting mixture was extracted with ethyl acetate (2×25 mL), then the combined extracts were washed with brine (30 mL). The organic phase was dried over anhydrous MgSO$_4$, filtered, and concentrated to provide {4-[1-(2,5-dichloro-benzenesulfonyl)-piperidin-4-yl]-6-fluoro-3-methyl-naphthalen-2-yl}-acetic acid (47 mg, 93%) as a yellow film. MS calcd. for $C_{24}H_{23}Cl_2FNO_4S$ [(M+H)$^+$]: 510, obsd. 510.

Example 18

{4-[1-(2,6-Dichloro-benzenesulfonyl)-piperidin-4-yl]-6-fluoro-3-methyl-naphthalen-2-yl}-acetic acid

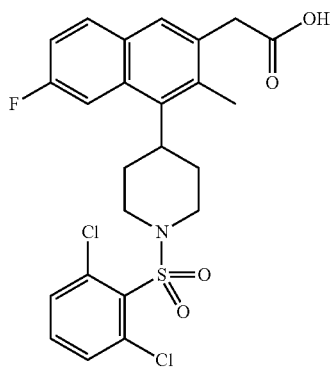 [SMILES: Cc1c(CC(=O)O)cc2ccc(F)cc2c1C1CCN(S(=O)(=O)c2c(Cl)cccc2Cl)CC1]

{4-[1-(2,6-Dichloro-benzenesulfonyl)-piperidin-4-yl]-6-fluoro-3-methyl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 μL, 0.711 mmol) in methylene chloride (6.0 mL) was added 2,6-dichlorobenzenesulfonyl chloride (116 mg, 0.47 mmol). After stirring for ~25 minutes at 0° C., the light yellow reaction mixture was allowed to warm to room temperature and then was stirred for 6.5 hours at room temperature under nitrogen. During this time, some solvent had evaporated. Methylene chloride (~10 mL) and water (~25 mL) were added and the mixture was extracted with methylene chloride (2×25 mL). The combined extracts were washed with brine solution, dried over anhydrous MgSO$_4$, filtered, concentrated, and purified by silica gel chromatography (eluting with 25% ethyl acetate/hexanes) to give {4-[1-(2,6-dichloro-benzenesulfonyl)-piperidin-4-yl]-6-fluoro-3-methyl-naphthalen-2-yl}-acetic acid methyl ester (96 mg, 77%) as a light yellow product. MS calcd. for $C_{25}H_{25}Cl_2FNO_4S$ [(M+H)$^+$]: 524, obsd. 524.1.

{4-[1-(2,6-Dichloro-benzenesulfonyl)-piperidin-4-yl]-6-fluoro-3-methyl-naphthalen-2-yl}-acetic acid To a solution of {4-[1-(2,6-dichloro-benzenesulfonyl)-piperidin-4-yl]-6-fluoro-3-methyl-naphthalen-2-yl}-acetic acid methyl ester (96 mg, 0.183 mmol) in THF (8.0 mL) was added a solution of lithium hydroxide monohydrate (87.6 mg, 2.1 mmol) in water (2 mL). The reaction mixture was stirred at room temperature overnight under nitrogen. After this time, the reaction mixture was diluted with water (~20 mL) and then acidified with 1.0 N aqueous HCl (3.66 mL). The resulting mixture was extracted with ethyl acetate (2×25 mL), then the combined extracts were washed with brine (30 mL). The organic phase was dried over anhydrous MgSO$_4$, filtered, and concentrated to provide {4-[1-(2,6-dichloro-benzenesulfonyl)-piperidin-4-yl]-6-fluoro-3-methyl-naphthalen-2-yl}-acetic acid (63 mg, 67%) as a yellow solid. MS calcd. for $C_{24}H_{23}Cl_2FNO_4S$ [(M+H)$^+$]: 510, obsd. 510.1.

Example 19

[6-Fluoro-3-methyl-4-(1-phenylmethanesulfonyl-piperidin-4-yl)-naphthalen-2-yl]-acetic acid

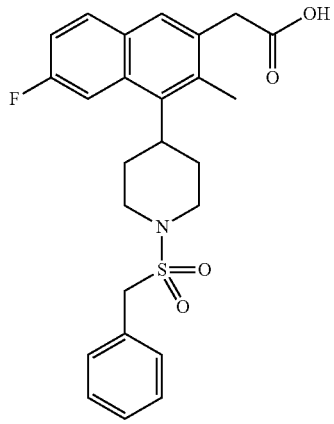 [SMILES: Cc1c(CC(=O)O)cc2ccc(F)cc2c1C1CCN(S(=O)(=O)Cc2ccccc2)CC1]

[6-Fluoro-3-methyl-4-(1-phenylmethanesulfonyl-piperidin-4-yl)-naphthalen-2-yl]-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (6.0 mL) was added α-toluenesulfonyl chloride (90.4 mg, 0.474 mmol). After stirring for ~10 minutes at 0° C., the light yellow reaction mixture was allowed to warm to room temperature and then stirred for 4 hours at room temperature under nitrogen. During this time, some solvent had evaporated. The reaction mixture was diluted with water (~25 mL) and extracted with methylene chloride (3×25 mL). The combined organic layers were washed with brine, dried over anhydrous $MgSO_4$, filtered, concentrated, and purified by silica gel chromatography (eluting with 33% ethyl acetate/hexanes) to give [6-fluoro-3-methyl-4-(1-phenylmethanesulfonyl-piperidin-4-yl)-naphthalen-2-yl]-acetic acid methyl ester (88 mg, 79%). MS calcd. for $C_{26}H_{29}FNO_4S$ [(M+H)$^+$]: 470, obsd. 470.2.

[6-Fluoro-3-methyl-4-(1-phenylmethanesulfonyl-piperidin-4-yl)-naphthalen-2-yl]-acetic acid To a solution [6-fluoro-3-methyl-4-(1-phenylmethanesulfonyl-piperidin-4-yl)-naphthalen-2-yl]-acetic acid methyl ester (82 mg, 0.175 mmol) in THF (8.0 mL) was added a solution of lithium hydroxide monohydrate (83.8 mg, 2 mmol) in water (2 mL). The reaction mixture was stirred at room temperature overnight under nitrogen. After this time, the reaction mixture was diluted with water (~20 mL) and then acidified with 1.0 N aqueous HCl (3.5 mL). The resulting white precipitate was collected by vacuum filtration, washed with hexanes, and then further dried under vacuum to provide [6-fluoro-3-methyl-4-(1-phenylmethane-sulfonyl-piperidin-4-yl)-naphthalen-2-yl]-acetic acid (50 mg, 63%). $^1$H NMR (400 MHz, DMSO-d$_6$) δ ppm 12.43 (br. s., 1H), 7.90 (dd, J=9.03, 6.53 Hz, 1H), 7.80-8.13 (m, 1H), 7.69 (s, 1H), 7.31-7.53 (m, 6H), 4.49 (br. s., 2H), 3.66-3.85 (m, 4H), 3.46-3.57 (m, 1H), 2.87-3.20 (m, 2H), 2.41 (br. s., 3H), 2.13-2.37 (m, 2H), 1.61-1.71 (m, 2H). MS calcd. for $C_{25}H_{27}FNO_4S$ [(M+H)$^+$]: 456, obsd. 456.2.

Example 20

{6-Fluoro-4-[1-(2-methoxy-benzenesulfonyl)-piperidin-4-yl]-3-methyl-naphthalen-2-yl}-acetic acid

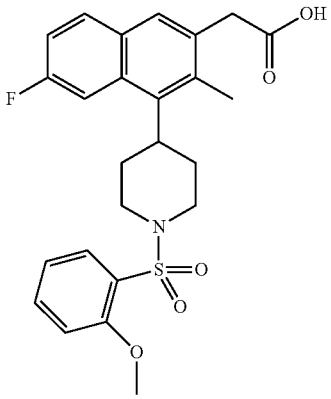 [SMILES: COc1ccccc1S(=O)(=O)N1CCC(c2c(C)c(CC(=O)O)cc3ccc(F)cc23)CC1]

{6-Fluoro-4-[1-(2-methoxy-benzenesulfonyl)-piperidin-4-yl]-3-methyl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (6.0 mL) was added 2-methoxybenzenesulfonyl chloride (98 mg, 0.474 mmol). After stirring for ~10 minutes at 0° C., the light yellow reaction mixture was allowed to warm to room temperature and then was stirred for 4 hours at room temperature under nitrogen. During this time, some solvent had evaporated. Additional methylene chloride was added. The reaction mixture was diluted with water (~25 mL) and extracted with methylene chloride (3×25 mL). The combined organic layers were washed with brine, dried over anhydrous $MgSO_4$, filtered and concentrated. Silica gel chromatography (20-33% ethyl acetate/hexanes) afforded {6-fluoro-4-[1-(2-methoxy-benzenesulfonyl)-piperidin-4-yl]-3-methyl-naphthalen-2-yl}-acetic acid methyl ester (64 mg, 55%). MS calcd. for $C_{26}H_{29}FNO_5S$ [(M+H)$^+$]: 486, obsd. 486.2.

{6-Fluoro-4-[1-(2-methoxy-benzenesulfonyl)-piperidin-4-yl]-3-methyl-naphthalen-2-yl}-acetic acid To a solution of {6-fluoro-4-[1-(2-methoxy-benzenesulfonyl)-piperidin-4-yl]-3-methyl-naphthalen-2-yl}-acetic acid methyl ester (64 mg, 0.132 mmol) in THF (8.0 mL) was added a solution of lithium hydroxide monohydrate (63.3 mg, 1.5 mmol) in water (2 mL). The reaction mixture was stirred at room temperature overnight under nitrogen. After this time, the reaction mixture was concentrated. Water (~20 mL) was added and the mixture was acidified with 1.0 N aqueous HCl (2.7 mL). The resulting white precipitate was collected by vacuum filtration, washed with hexanes, and then further dried under vacuum to provide {6-fluoro-4-[1-(2-methoxy-benzenesulfonyl)-piperidin-4-yl]-3-methyl-naphthalen-2-yl}-acetic acid (51.5 mg, 83%). $^1$H NMR (400 MHz, DMSO-d$_6$) δ ppm 12.45 (br. s, 1H), 8.04 (br. s, 1H), 7.85-7.92 (m, 1H), 7.78-7.84 (m, 1H), 7.67 (s, 2H), 7.29-7.37 (m, 2H), 7.13 (t, J=8.00 Hz, 1H), 3.94 (s, 3H), 3.82-3.92 (m, 2H), 3.70-3.80 (m, 2H), 2.82-3.02 (m, 2H), 2.35 (s, 3H), 2.13-2.32 (m, 1H), 1.60-1.71 (m, 2H). MS calcd. for $C_{25}H_{27}FNO_5S$ [(M+H)$^+$]: 472, obsd. 472.2.

Example 21

{4-[1-(3-Chloro-phenylmethanesulfonyl)-piperidin-4-yl]-6-fluoro-3-methyl-naphthalen-2-yl}-acetic acid

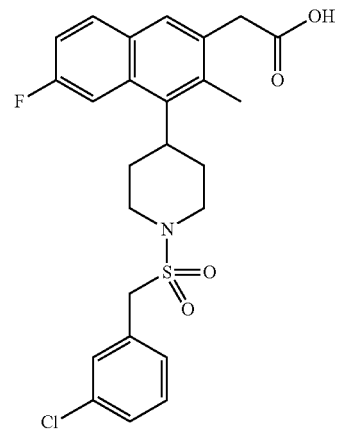 [SMILES: Cc1c(CC(=O)O)cc2ccc(F)cc2c1C1CCN(S(=O)(=O)Cc2cccc(Cl)c2)CC1]

{4-[1-(3-Chloro-phenylmethanesulfonyl)-piperidin-4-yl]-6-fluoro-3-methyl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 μL, 0.711 mmol) in methylene chloride (6.0 mL) was added (3-chloro-phenyl)-methanesulfonyl chloride (106.7 mg, 0.474 mmol). The reaction mixture was stirred at 0° C. for 10 minutes, then it was warmed to room temperature and stirred at room temperature overnight. The reaction mixture was diluted with water. The resulting mixture was extracted with ethyl acetate. The organic phase was dried over MgSO$_4$, filtered, and concentrated. Silica gel chromatography (20-25% ethyl acetate in hexanes) provided {4-[1-(3-chloro-phenylmethanesulfonyl)-piperidin-4-yl]-6-fluoro-3-methyl-naphthalen-2-yl}-acetic acid methyl ester (52.4 mg, 44%) as a colorless film. MS cald. For $C_{26}H_{28}ClFNO_4S$ [(M+H)$^+$]: 504, obsd. 504.1.

{4-[1-(3-Chloro-phenylmethanesulfonyl)-piperidin-4-yl]-6-fluoro-3-methyl-naphthalen-2-yl}-acetic acid To a solution {4-[1-(3-chloro-phenylmethanesulfonyl)-piperidin-4-yl]-6-fluoro-3-methyl-naphthalen-2-yl}-acetic acid methyl ester (52.4 mg, 0.104 mmol) in THF (8.0 mL) was added a solution of lithium hydroxide monohydrate (49.8 mg, 2.08 mmol) in water (2.0 mL) at room temperature. The resulting solution was stirred overnight under a nitrogen atmosphere. The solvent was evaporated. Water (~25 mL) was added and the mixture was acidified with 1.0 N aqueous HCl (2.1 mL). The resulting white precipitate was collected by filtration, washed with water and hexanes, and dried under high vacuum. This crude product was further purified using preparative reverse-phase HPLC to give {4-[1-(3-chloro-phenylmethanesulfonyl)-piperidin-4-yl]-6-fluoro-3-methyl-naphthalen-2-yl}-acetic acid (9 mg, 18%) as a white solid. $^1$H NMR (400 MHz, DMSO-d$_6$) δ ppm 12.44 (br. s, 1H), 7.95-8.12 (m, 1H), 7.90 (dd, J=9.03, 6.53 Hz, 1H), 7.65-7.74 (m, 2H), 7.55 (s, 1H), 7.46 (d, J=1.00 Hz, 2H), 7.36 (t, J=9.00 Hz, 1H), 4.54 (br. s., 2H), 4.13 (dd, J=5.52, 3.51 Hz, 1H), 3.78 (br. s., 4H), 3.48-3.65 (m, 1H), 2.91-3.22 (m, 3H), 2.42 (br. s., 5H), 1.69 (m, 2H). MS cald. for $C_{25}H_{26}ClFNO_4S$ [(M+H)$^+$]: 490, obsd. 490.2.

Example 22

{4-[1-(4-Chloro-phenylmethanesulfonyl)-piperidin-4-yl]-6-fluoro-3-methyl-naphthalen-2-yl}-acetic acid

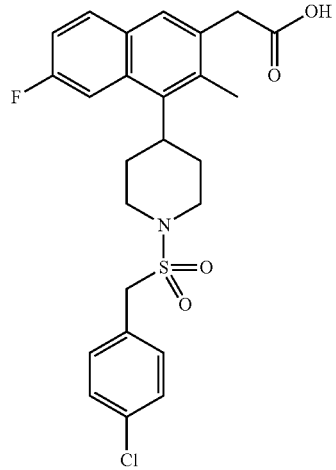 [SMILES: Cc1c(CC(=O)O)cc2ccc(F)cc2c1C1CCN(S(=O)(=O)Cc2ccc(Cl)cc2)CC1]

{4-[1-(4-Chloro-phenylmethanesulfonyl)-piperidin-4-yl]-6-fluoro-3-methyl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 μL, 0.711 mmol) in methylene chloride (6.0 mL) was added (4-chloro-phenyl)-methanesulfonyl chloride (106.7 mg, 0.474 mmol). The reaction mixture was stirred at 0° C. for 10 minutes, then it was warmed to room temperature and stirred at room temperature for four hours. The reaction mixture was diluted with water (25 mL). The resulting mixture was extracted with ethyl acetate (2×25 mL). The organic phase was dried over MgSO$_4$, filtered, and concentrated. Silica gel chromatography (20-25% ethyl acetate in hexanes) provided {4-[1-(4-chloro-phenylmethanesulfonyl)-piperidin-4-yl]-6-fluoro-3-methyl-naphthalen-2-yl}-acetic acid methyl ester (28.5 mg, 24%) as a colorless film. MS cald. For $C_{26}H_{28}ClFNO_4S$ [(M+H)$^+$]: 504, obsd. 504.2.

{4-[1-(4-Chloro-phenylmethanesulfonyl)-piperidin-4-yl]-6-fluoro-3-methyl-naphthalen-2-yl}-acetic acid To a solution {4-[1-(4-chloro-phenylmethanesulfonyl)-piperidin-4-yl]-6-fluoro-3-methyl-naphthalen-2-yl}-acetic acid methyl ester (28.5 mg, 0.057 mmol) in THF (8.0 mL) was added a solution of lithium hydroxide monohydrate (27.3 mg, 1.14 mmol) in water (2.0 mL) at room temperature. The resulting solution was stirred overnight under a nitrogen atmosphere. The solvent was evaporated. Water (~25 mL) was added and the mixture was acidified with 1.0 N aqueous HCl (1.1 mL). The resulting white precipitate was collected by filtration, washed with water and hexanes, and dried under high vacuum. This crude product was further purified using preparative reverse-phase HPLC to give {4-[1-(4-chloro-phenylmethanesulfonyl)-piperidin-4-yl]-6-fluoro-3-methyl-naphthalen-2-yl}-acetic acid (11.2 mg, 40%) as a white solid. $^1$H NMR (400 MHz, DMSO-d$_6$) δ ppm 12.42 (br. s, 1H), 7.90 (dd, J=9.00, 6.50 Hz, 1H), 7.78-8.11 (m, 1H), 7.69 (s, 1H), 7.50 (s, 4H), 7.36 (td, J=9.00, 2.50 Hz, 1H), 4.53 (br. s, 2H), 3.64-3.86 (m, 5H), 2.91-3.19 (m, 3H), 2.41 (br. s., 3H), 2.15-2.35 (br. s, 1H), 1.61-1.73 (m, 2H). MS cald. for $C_{25}H_{25}ClFNO_4S$ [(M+H)$^+$]: 490, obsd. 490.1.

Example 23

{6-Fluoro-3-methyl-4-[1-(3-trifluoromethyl-benzenesulfonyl)-piperidin-4-yl-naphthalen-2-yl}-acetic acid

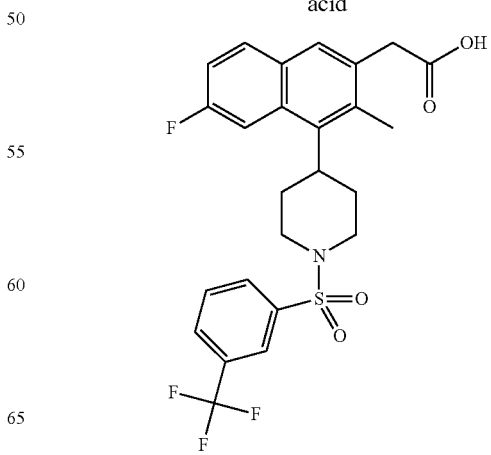

{6-Fluoro-3-methyl-4-[1-(3-trifluoromethyl-benzenesulfonyl)-piperidin-4-yl-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (6.0 mL) was added 3-(trifluoromethyl)benzenesulfonyl chloride (76 µL, 0.474 mmol). After stirring for ~10 minutes at 0° C., the light yellow reaction mixture was allowed to warm to room temperature and then was stirred for overnight at room temperature. Water (~25 mL) was added and the mixture was extracted with methylene chloride (2×30 mL). The combined organic layers were washed with brine, dried over anhydrous $MgSO_4$, filtered and concentrated. Silica gel chromatography (25-33% ethyl acetate in hexanes) afforded {6-fluoro-3-methyl-4-[1-(3-trifluoromethyl-benzenesulfonyl)-piperidin-4-yl]-naphthalen-2-yl}-acetic acid methyl ester (104 mg, 84%). MS cald. for $C_{26}H_{26}F_4NO_4S$ [$(M+H)^+$]: 524, obsd. 524.1.

{6-Fluoro-3-methyl-4-[1-(3-trifluoromethyl-benzenesulfonyl)-piperidin-4-yl-naphthalen-2-yl}-acetic acid To a solution of {6-fluoro-3-methyl-4-[1-(3-trifluoromethyl-benzenesulfonyl)-piperidin-4-yl]-naphthalen-2-yl}-acetic acid methyl ester (104.2 mg, 0.199 mmol) in THF (8.0 mL) was added a solution of lithium hydroxide monohydrate (95.3 mg, 2.3 mmol) in water (2 mL). The reaction mixture was stirred at room temperature overnight under nitrogen. After this time, the reaction mixture was concentrated. Water (~25 mL) was added and the mixture was acidified with 1.0 N aqueous HCl (4 mL). The resulting white precipitate was collected by vacuum filtration, washed with water and hexanes, and then further dried under vacuum to afford {6-fluoro-3-methyl-4-[1-(3-trifluoromethyl-benzenesulfonyl)-piperidin-4-yl]-naphthalen-2-yl}-acetic acid (92.2 mg, 91%). $^1$H NMR (400 MHz, DMSO-$d_6$) δ ppm 12.43 (br. s, 1H), 8.18-8.20 (m, 1H), 8.16-8.18 (m, 1H), 8.07 (s, 1H), 7.97 (t, J=7.80 Hz, 1H), 7.84-7.91 (m, 1H), 7.67 (s, 1H), 7.33 (t, J=9.00 Hz, 1H), 3.92 (br. s., 2H), 3.74 (s, 2H), 3.41-3.70 (m, 2H), 2.57-2.84 (m, 2H), 2.31 (s, 3H), 2.40-2.28 (m, 1H), 1.69 (m, 2H). MS cald. for $C_{25}H_{22}F_4NO_4S$ [$(M-H)^-$]: 508, obsd. 508.1.

Example 24

[4-(1-Cyclopentanesulfonyl-piperidin-4-yl)-6-fluoro-3-methyl-naphthalen-2-yl]-acetic acid

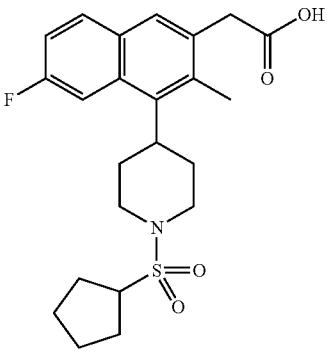 [SMILES: Cc1c(CC(=O)O)cc2ccc(F)cc2c1C1CCN(S(=O)(=O)C2CCCC2)CC1]

[4-(1-Cyclopentanesulfonyl-piperidin-4-yl)-6-fluoro-3-methyl-naphthalen-2-yl]-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (10.0 mL) was added cyclopentanesulfonyl chloride (62.5 µL, 0.474 mmol). The reaction mixture was stirred at 0° C. for 20 minutes, then it was warmed to room temperature and stirred at room temperature overnight. The reaction mixture was diluted with water (25 mL). The resulting mixture was extracted with methylene chloride (2×30 mL). The organic phase was dried over $MgSO_4$, filtered, and concentrated. Silica gel chromatography (33% ethyl acetate in hexanes) provided [4-(1-cyclopentanesulfonyl-piperidin-4-yl)-6-fluoro-3-methyl-naphthalen-2-yl]-acetic acid methyl ester (64.8 mg, 61%). MS cald. For $C_{24}H_{31}FNO_4S$ [$(M+H)^+$]: 448, obsd. 448.2.

[4-(1-Cyclopentanesulfonyl-piperidin-4-yl)-6-fluoro-3-methyl-naphthalen-2-yl]-acetic acid To a solution of [4-(1-cyclopentanesulfonyl-piperidin-4-yl)-6-fluoro-3-methyl-naphthalen-2-yl]-acetic acid methyl ester (64.8 mg, 0.145 mmol) in THF (8.0 mL) was added a solution of lithium hydroxide monohydrate (69.5 mg, 1.7 mmol) in water (2.0 mL) at room temperature. The resulting solution was stirred for three hours under a nitrogen atmosphere. The solvent was evaporated. Water (20 mL) was added and the mixture was acidified with 1.0 N aqueous HCl (3 mL). The resulting white precipitate was collected by filtration, washed with water and hexanes, and dried under high vacuum. This crude product was further purified using preparative reverse-phase HPLC to give [4-(1-cyclopentanesulfonyl-piperidin-4-yl)-6-fluoro-3-methyl-naphthalen-2-yl]-acetic acid (19 mg, 30%) as a white solid. $^1$H NMR (400 MHz, DMSO-$d_6$) δ ppm 12.43 (br. s., 1H), 7.97-8.17 (m, 1H), 7.90 (dd, J=9.03, 6.53 Hz, 1H), 7.69 (s, 1H), 7.35 (t, J=7.53 Hz, 1H), 3.78 (br. s., 6H), 3.11 (br. s., 2H), 2.42 (br. s., 4H), 1.96-2.08 (m, 2H), 1.80-1.93 (m, 2H), 1.53-1.78 (m, 6H). MS cald. for $C_{23}H_{29}FNO_4S$ [$(M+H)^+$]: 434, obsd. 434.2.

Example 25

{6-Fluoro-3-methyl-4-[1-(pyrrolidine-1-sulfonyl)-piperidin-4-yl]-naphthalen-2-yl}-acetic acid

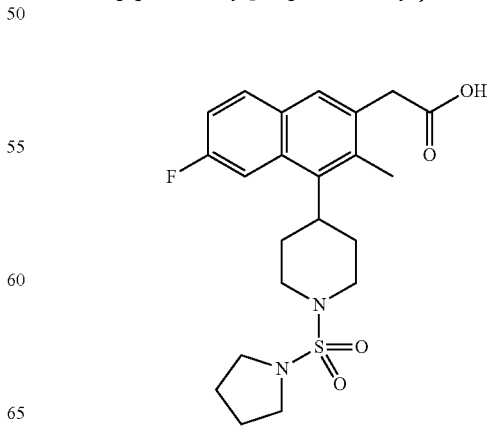

{6-Fluoro-3-methyl-4-[1-(pyrrolidine-1-sulfonyl)-piperidin-4-yl]-naphthalen-2-yl}-acetic acid methyl ester To a 0° C. solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (10.0 mL) was added pyrrolidine-1-sulfonyl chloride (80.4 mg, 0.474 mmol). The reaction mixture was stirred at 0° C. for 25 minutes, and then warmed to room temperature and stirred overnight. During this time period the solvent evaporated to dryness. Additional methylene chloride (10 mL) was added in the morning. The reaction mixture was diluted with water (25 mL). The resulting mixture was extracted with ethyl acetate (2×30 mL). The organic phase was dried over MgSO$_4$, filtered, and concentrated. Silica gel chromatography (33% ethyl acetate in hexanes) provided {6-fluoro-3-methyl-4-[1-(pyrrolidine-1-sulfonyl)-piperidin-4-yl]-naphthalen-2-yl}-acetic acid methyl ester (86.5 mg, 81%). MS cald. for $C_{23}H_{30}FN_2O_4S$ [(M+H)$^+$]: 449, obsd. 449.2.

{6-Fluoro-3-methyl-4-[1-(pyrrolidine-1-sulfonyl)-piperidin-4-yl]-naphthalen-2-yl}-acetic acid To a solution of {6-fluoro-3-methyl-4-[1-(pyrrolidine-1-sulfonyl)-piperidin-4-yl]-naphthalen-2-yl}-acetic acid methyl ester (86.5 mg, 0.193 mmol) in THF (8.0 mL) was added a solution of lithium hydroxide monohydrate (92.4 mg, 2.2 mmol) in water (2.0 mL) at room temperature. The resulting solution was stirred overnight under a nitrogen atmosphere. The solvent was evaporated. Water (20 mL) was added and the mixture was acidified with 1.0 N aqueous HCl (4 mL). The resulting white precipitate was collected by filtration, washed with water and hexanes, and dried under high vacuum to give {6-fluoro-3-methyl-4-[1-(pyrrolidine-1-sulfonyl)-piperidin-4-yl]-naphthalen-2-yl}-acetic acid (55.7 mg, 66%) as an off-white solid. $^1$H NMR (400 MHz, DMSO-d$_6$) δ 12.44 (br. s., 1H), 8.07 (br. s, 1H), 7.90 (dd, J=9.0, 6.5 Hz, 1H), 7.69 (s, 1H), 7.35 (td, J=8.5, 2.0 Hz, 1H), 3.78 (br. s., 4H), 3.22-3.43 (m, 5H), 3.09 (br. s., 2H), 2.42 (br. s., 3H), 1.81-1.97 (m, 4H), 1.67 (bd, 2H). MS cald. for $C_{22}H_{28}FN_2O_4S$ [(M+H)$^+$]: 434, obsd. 434.2.

Example 26

{6-Fluoro-3-methyl-4-[1-(2-nitro-phenylmethane-sulfonyl)-piperidin-4-yl]-naphthalen-2-yl}-acetic acid

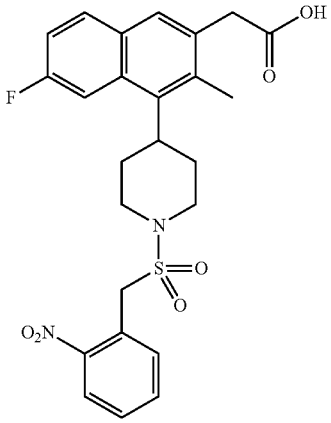

{6-Fluoro-3-methyl-4-[1-(2-nitro-phenylmethane-sulfonyl)-piperidin-4-yl]-naphthalen-2-yl}-acetic acid methyl ester A light brown solution of (6-fluoro-3-methyl-4-piperidin-4-yl-naphthalen-2-yl)-acetic acid methyl ester (which may be prepared as described above; 560 mg, 1.78 mmol) and (2-nitrophenyl)methanesulfonyl chloride (837 mg, 3.55 mmol) in THF (30 mL) was cooled to 0° C. under nitrogen and then N,N-diisopropylethylamine (930 µL, 5.34 mmol) was added. The resulting light brown solution was stirred for 2 hours at 0° C. temperature and then allowed to warm to room temperature and stirred for 36 hours. The reaction mixture was diluted with water and brine and the organic compound was extracted into ethyl acetate (2×100 mL). The combined organic layers were washed with brine and dried over MgSO$_4$, filtered, and concentrated. The crude product was purified using flash chromatography (120 g ISCO column eluting with 0-60% ethyl acetate/hexanes) to give {6-fluoro-3-methyl-4-[1-(2-nitro-phenylmethanesulfonyl)-piperidin-4-yl]-naphthalen-2-yl}-acetic acid methyl ester (645 mg, 71%) as a light yellow solid. $^1$H NMR (400 MHz, Chloroform-d) δ 8.07-8.1 (m, 1H), 7.85 (br. s, 1H), 7.55 (dd, J=8.8, 6.3 Hz, 1H), 7.67-7.72 (m, 2H), 7.56-7.64 (m, 2H), 7.16-7.24 (m, 1H), 4.83 (s, 2H), 3.89 (d, J=10.0 Hz, 2H), 3.82 (br. s, 2H), 3.72 (s, 3H), 3.43-3.63 (m, 1H), 2.90 (t, J=11.5 Hz, 2H), 2.32-2.71 (m, 5H), 1.77 (d, J=13.8 Hz, 2H). MS cald. for $C_{26}H_{27}FN_2O_6S$ [(M+H)$^+$] 514, obsd. 515.2.

{6-Fluoro-3-methyl-4-[1-(2-nitro-phenylmethane-sulfonyl)-piperidin-4-yl]-naphthalen-2-yl}-acetic acid To a light yellow solution of {6-fluoro-3-methyl-4-[1-(2-nitro-phenylmethanesulfonyl)-piperidin-4-yl]-naphthalen-2-yl}-acetic acid methyl ester (100 mg, 0.194 mmol) in THF (4 mL) was added a solution of lithium hydroxide (93.1 mg, 3.89 mmol) in water (1 mL) at room temperature. The resulting light brown solution was stirred for 15 hours at room temperature. The THF was evaporated off under vacuum and the basic aqueous layer was neutralized with 1.0 N HCl. The resulting solids were filtered using filter paper and washed with water and hexanes. The white solid (82 mg) was dissolved in ethyl acetate (~5 mL) with heating and the mixture was diluted with hexanes. During the dilution some precipitate was formed. Cooling in the refrigerator precipitated additional solids. {6-Fluoro-3-methyl-4-[1-(2-nitro-phenyl-methanesulfonyl)-piperidin-4-yl]-naphthalen-2-yl}-acetic acid (88 mg, 90%) was isolated as a white solid. $^1$H NMR (400 MHz, DMSO-d6) δ 12.44 (br. s, 1H), 8.08 (d, J=8.03 Hz, 1H), 7.90 (dd, J=8.91, 6.65 Hz, 1H), 7.74-7.86 (m, 3H), 7.64-7.73 (m, 2H), 7.36 (t, J=8.03 Hz, 1H), 4.97 (s, 2H), 3.52-3.90 (m, 7H), 2.42 (br. s, 3H), 1.60-184 (m, 4H). MS cald. for $C_{25}H_{25}FN_2O_6S$ [(M+H)$^+$] 500, obsd. 501.1.

Example 27

{4-[1-(2-Amino-phenylmethanesulfonyl)-piperidin-4-yl]-6-fluoro-3-methyl-naphthalen-2-yl}-acetic acid

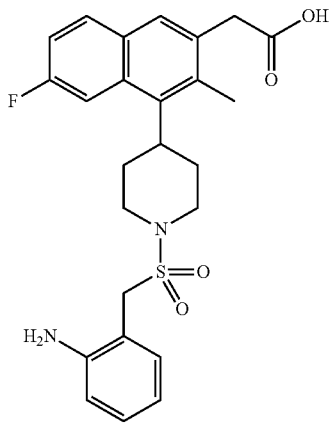 [SMILES: Cc1c(CC(=O)O)cc2ccc(F)cc2c1C1CCN(S(=O)(=O)Cc2ccccc2[N+](=O)[O-])CC1]

{4-[1-(2-Amino-phenylmethanesulfonyl)-piperidin-4-yl]-6-fluoro-3-methyl-naphthalen-2-yl}-acetic acid methyl ester A mixture of {6-fluoro-3-methyl-4-[1-(2-nitro-phenylmethanesulfonyl)-piperidin-4-yl]-naphthalen-2-yl}-acetic acid methyl ester (505 mg, 0.981 mmol), zinc dust (325 mesh) (642 mg, 9.82 mmol), and ammonium chloride (787 mg, 14.7 mmol, was combined with methanol (10 mL) and water (5 mL) under nitrogen to create a suspension. Moderate heating using a heat gun was used to bring more of the starting material into solution, and more methanol (5 mL) was added. The suspension was stirred for two hours at which time LCMS and TLC analysis (1:1 hexane-ethyl acetate) analysis indicated the presence of unreacted starting material and a more polar product. Another 20 equivalents of zinc dust (1.02 g) was added and the reaction mixture was stirred for two hours with some heating with a heat gun during this time period. TLC analysis indicated that the reaction was not complete. Another 30 equivalents of ammonium chloride (1.4 g) was added and the resulting suspension was heated to 40-50° C. with a heating mantle. The reaction mixture was cooled to room temperature and the zinc was filtered-off and washed with methanol. The filtrate was concentrated and the residue was diluted with water. The suspension was extracted with ethyl acetate (2×75 mL) and the combined extracts were washed with brine, dried over MgSO$_4$, filtered, and concentrated. Flash chromatography (80 g ISCO column, eluting with 0-70% ethyl acetate/hexanes) provided {4-[1-(2-amino-phenylmethanesulfonyl)-piperidin-4-yl]-6-fluoro-3-methyl-naphthalen-2-yl}-acetic acid methyl ester (385 mg, 81%) as a white solid. MS cald. for $C_{26}H_{30}FN_2O_4S$ [(M+H)$^+$] 484, obsd. 485.2.

{4-[1-(2-Amino-phenylmethanesulfonyl)-piperidin-4-yl]-6-fluoro-3-methyl-naphthalen-2-yl}-acetic acid To a solution of {4-[1-(2-amino-phenylmethanesulfonyl)-piperidin-4-yl]-6-fluoro-3-methyl-naphthalen-2-yl}-acetic acid methyl ester (178 mg, 0.367 mmol) in THF 8.0 mL) was added a solution of lithium hydroxide monohydrate (176 mg, 7.35 mmol) in water (2.0 mL) at room temperature. The resulting solution was stirred for 15 hours under nitrogen. The solvent was removed under vacuum and the aqueous solution was diluted with water and slowly neutralized with 1.0 N HCl until the pH was between 5 and 6. The resulting precipitated solids were collected by filtration and washed with water and hexanes. After drying in the air, {4-[1-(2-amino-phenylmethane-sulfonyl)-piperidin-4-yl]-6-fluoro-3-methyl-naphthalen-2-yl}-acetic acid (159 mg, 92%) was isolated as an off-white solid. $^1$H NMR (400 MHz, DMSO-d6) δ 12.44 (br. s, 1H), 7.86 (dd, J=8.85, 6.59 Hz, 1H), 7.61 (s, 1H), 7.31 (t, J=7.91 Hz, 1H), 7.18 (d, J=7.35 Hz, 1H), 6.99-7.12 (m, 2H), 6.68-6.78 (m, 1H), 6.53-6.67 (m, 1H), 5.14 (br. s, 2H), 4.28-4.51 (m, 4H), 3.76 (d, J=10.93 Hz, 2H), 3.61 (br. s, 5H), 2.41 (br. s, 3H), 1.66 (d, J=11.49 Hz, 2H). MS cald. for $C_{25}H_{26}FN_2O_4S$ [(M–H)$^-$] 469, obsd. 469.1.

Example 28

{4-[1-(2,4-Dichloro-benzoyl)-piperidin-4-yl]-6-fluoro-3-methyl-naphthalen-2-yl}-acetic acid

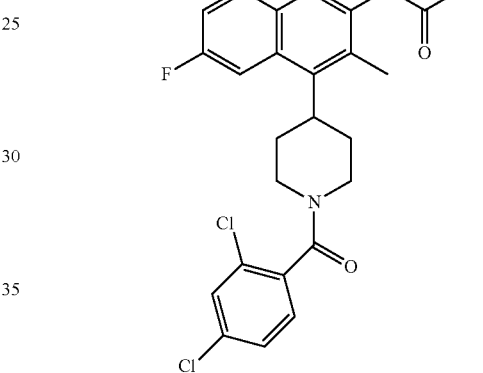

{4-[1-(2,4-Dichloro-benzoyl)-piperidin-4-yl]-6-fluoro-3-methyl-naphthalen-2-yl}-acetic acid methyl ester To a light brown solution of (6-fluoro-3-methyl-4-piperidin-4-yl-naphthalen-2-yl)-acetic acid methyl ester (which may be prepared as described above; 110 mg, 0.35 mmol) and 2,4-dichlorobenzoyl chloride (110 mg, 0.53 mmol) in dichloromethane (10 mL) was added N,N-diisopropylethylamine (183 µL, 1.05 mmol) at room temperature under a nitrogen atmosphere. The resulting light brown solution was stirred for 15 hours. The reaction mixture was diluted with water and brine and the resulting mixture was extracted into ethyl acetate (2×50 mL). The combined organic extracts were washed with brine solution, dried over MgSO$_4$, filtered, and concentrated to give the crude product. Flash chromatography (40 g ISCO column, eluting with 0-60% ethyl acetate/hexanes) provided {4-[1-(2,4-dichloro-benzoyl)-piperidin-4-yl]-6-fluoro-3-methyl-naphthalen-2-yl}-acetic acid methyl ester (111 mg, 65%) as a white solid. MS cald. for $C_{26}H_{25}Cl_2FNO_3$ [(M+H)$^-$] 488, obsd. 488.0.

{4-[1-(2,4-Dichloro-benzoyl)-piperidin-4-yl]-6-fluoro-3-methyl-naphthalen-2-yl}-acetic acid To a colorless solution of {4-[1-(2,4-dichloro-benzoyl)-piperidin-4-yl]-6-fluoro-3-methyl-naphthalen-2-yl}-acetic acid methyl ester (102 mg, 0.21 mmol) in THF (8.0 mL) was added a solution of lithium hydroxide monohydrate (100 mg, 4.2 mmol) in water (2.0 mL) at room temperature. The resulting colorless solution was stirred for 15 hours. The solvent was removed and the aqueous solution after dilution with water was neutralized with 1.0 N aqueous HCl. The resulting white precipitate was collected by filtration and washed with hexanes. After drying in the air, 62 mg of the crude product was isolated as a white solid. The crude product was dissolved in ethyl acetate (~3 mL) with heating and the resulting solution was diluted with hexanes (~20 mL). The solution was stored in the freezer for three days and the precipitated solids were collected by filtration and washed with hexanes. After drying in air, {4-[1-(2,4-dichloro-benzoyl)-piperidin-4-yl]-6-fluoro-3-methyl-naphthalen-2-yl}-acetic acid (48 mg, 48%) was isolated as an off-white solid. $^1$H NMR (400 MHz, DMSO-$d_6$) δ ppm 12.42 (br. s, 1H), 7.85-7.97 (m, 1H), 7.81 (br. s, 1H), 7.75 (s, 1H), 7.69 (s, 1H), 7.51-7.63 (m, 1H), 7.41-7.50 (m, 1H), 7.35 (t, J=8.03 Hz, 1H), 4.71 (br. s, 1H), 3.78 (br. s, 4H), 3.40 (br. s, 2H), 2.42 (br. s, 3H), 1.77 (br. s, 2H), 1.60 (d, J=9.79 Hz, 2H). MS cald. for $C_{25}H_{23}Cl_2FNO_3$ [(M+H)$^+$] 474, obsd. 474.1.

Example 29

{4-[1-(2,6-Dichloro-benzoyl)-piperidin-4-yl]-6-fluoro-3-methyl-naphthalen-2-yl}-acetic acid

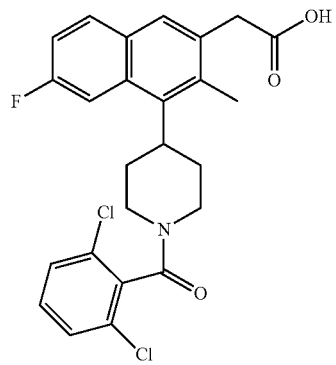 [SMILES: Cc1c(CC(=O)O)cc2ccc(F)cc2c1C1CCN(C(=O)c2c(Cl)cccc2Cl)CC1]

{4-[1-(2,6-Dichloro-benzoyl)-piperidin-4-yl]-6-fluoro-3-methyl-naphthalen-2-yl}-acetic acid methyl ester To a solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (10.0 mL) was added 2,6-dichlorobenzoyl chloride (74.4 mg, 0.355 mmol). The reaction mixture was stirred for three hours at room temperature. Water (~25 mL) was added and the mixture was extracted with methylene chloride (2×25 mL). The combined organic layers were washed with brine, dried over anhydrous MgSO$_4$, filtered and concentrated. Silica gel chromatography (25% ethyl acetate in hexanes) afforded {4-[1-(2,6-dichloro-benzoyl)-piperidin-4-yl]-6-fluoro-3-methyl-naphthalen-2-yl}-acetic acid methyl ester (100 mg, 86%). $^1$H NMR (400 MHz, DMSO-$d_6$) δ ppm 7.85-8.20 (m, 1H), 7.87-7.96 (m, 1H), 7.71 (s, 1H), 7.55-7.66 (m, 2H), 7.48 (s, 1H), 7.31-7.40 (m, 1H), 4.67-4.81 (m, 1H), 3.74-3.97 (m, 3H), 3.63 (s, 3H), 3.35-3.44 (m, 2H), 3.02-3.21 (m, 1H), 2.40 (s, 2H), 2.17-2.31 (m, 1H), 1.58-1.84 (m, 2H).

{4-[1-(2,6-Dichloro-benzoyl)-piperidin-4-yl]-6-fluoro-3-methyl-naphthalen-2-yl}-acetic acid To a solution of {4-[1-(2,6-dichloro-benzoyl)-piperidin-4-yl]-6-fluoro-3-methyl-naphthalen-2-yl}-acetic acid methyl ester (96 mg, 0.197 mmol) in THF (8.0 mL) was added a solution of lithium hydroxide monohydrate (94.2 mg, 2.2 mmol) in water (2 mL). The reaction mixture was stirred at room temperature overnight. After this time, the reaction mixture was concentrated. Water (~20 mL) was added and the mixture was acidified with 1.0 N aqueous HCl (3.9 mL). The resulting white precipitate was collected by vacuum filtration, washed with hexanes, and then further dried under vacuum to {4-[1-(2,6-dichloro-benzoyl)-piperidin-4-yl]-6-fluoro-3-methyl-naphthalen-2-yl}-acetic acid (66 mg, 71%). $^1$H NMR (300 MHz, DMSO-$d_6$) δ ppm 7.84-7.97 (m, 2H), 7.68 (s, 1H), 7.55-7.66 (m, 2H), 7.44-7.53 (m, 1H), 7.34 (s, 1H), 4.69-4.80 (m, 1H), 3.76 (br. s., 2H), 3.32 (br. s., 6H), 2.43 (s, 2H), 1.57-1.85 (m, 2H). MS cald. for $C_{25}H_{23}Cl_2FNO_3$ [(M+H)$^+$]: 474, obsd. 474.1.

Example 30

{4-[1-(2,5-Difluoro-benzoyl)-piperidin-4-yl]-6-fluoro-3-methyl-naphthalen-2-yl}-acetic acid

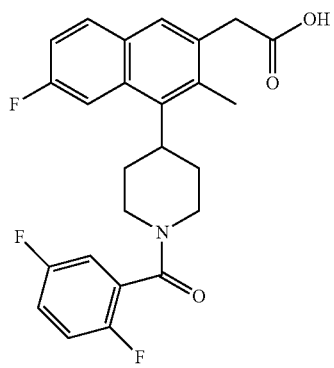 [SMILES: Cc1c(CC(=O)O)cc2ccc(F)cc2c1C1CCN(C(=O)c2cc(F)ccc2F)CC1]

{4-[1-(2,5-Difluoro-benzoyl)-piperidin-4-yl]-6-fluoro-3-methyl-naphthalen-2-yl}-acetic acid methyl ester To a solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 µL, 0.711 mmol) in methylene chloride (10.0 mL) was added 2,5-difluorobenzoyl chloride (62.7 mg, 0.355 mmol). The reaction mixture was stirred for three hours at room temperature Water (~25 mL) was added and the mixture was extracted with methylene chloride (2×25 mL). The combined organic layers were washed with brine, dried over anhydrous MgSO$_4$, filtered and concentrated. Silica gel chromatography (25% ethyl acetate in hexanes) afforded {4-[1-(2,5-difluoro-benzoyl)-piperidin-4-yl]-6-fluoro-3-methyl-naphthalen-2-yl}-acetic acid methyl ester (73 mg, 68%).

{4-[1-(2,5-Difluoro-benzoyl)-piperidin-4-yl]-6-fluoro-3-methyl-naphthalen-2-yl}-acetic acid To a solution of {4-[1-(2,5-difluoro-benzoyl)-piperidin-4-yl]-6-fluoro-3-methyl-naphthalen-2-yl}-acetic acid methyl ester (73 mg, 0.160 mmol) in THF (8.0 mL) was added a solution of lithium hydroxide monohydrate (76.6 mg, 1.8 mmol) in water (2 mL). The reaction mixture was stirred at room temperature overnight. After this time, the reaction mixture was concentrated. Water (~20 mL) was added and the mixture was acidified with 1.0 N aqueous HCl (3.2 mL). The resulting white precipitate was collected by vacuum filtration, washed with hexanes, and then further dried under vacuum to give {4-[1-(2,5-difluoro-benzoyl)-piperidin-4-yl]-6-fluoro-3-methyl-naphthalen-2-yl}-acetic acid (57.5 mg, 81%). $^1$H NMR (400 MHz, DMSO-$d_6$) δ ppm 12.46 (br. s, 1H), 7.80-8.20 (m, 1H), 7.90 (dd, J=9.00, 6.50 Hz, 1H), 7.69 (s, 1H), 7.31-7.52 (m, 4H), 4.62-4.77 (m, 1H), 3.68-4.08 (m, 4H), 3.48-3.60 (m, 1H), 2.95-3.21 (m, 1H), 2.43 (br. s., 3H), 2.11-2.34 (m, 2H), 1.57-1.82 (m, 2H). MS cald. for $C_{25}H_{23}F_3NO_3$ [(M+H)$^+$]: 442, obsd. 442.2.

Example 31

[6-Fluoro-3-methyl-4-(1-phenylacetyl-piperidin-4-yl)-naphthalen-2-yl]-acetic acid

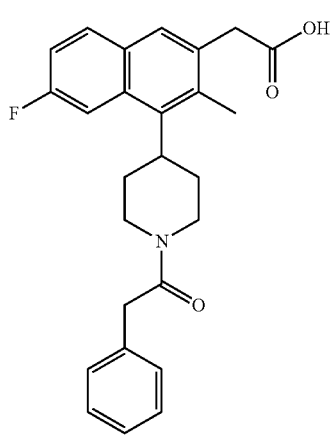 [SMILES: Cc1c(CC(=O)O)cc2ccc(F)cc2c1C1CCN(C(=O)Cc2ccccc2)CC1]

[6-Fluoro-3-methyl-4-(1-phenylacetyl-piperidin-4-yl)-naphthalen-2-yl]-acetic acid methyl ester To a solution of (6-fluoro-3-methyl-4-piperidin-4-yl-naphthalen-2-yl)-acetic acid methyl ester trifluoroacetate salt (which may be prepared as described above; 102 mg, 0.237 mmol) and N,N-diisopropylethylamine (124 μL, 0.711 mmol) in methylene chloride (10.0 mL) was added phenylacetyl chloride (47 μL, 0.355 mmol). The reaction mixture was stirred for four hours at room temperature. Water (~25 mL) was added and the mixture was extracted with methylene chloride (2×25 mL). The combined organic layers were washed with brine, dried over anhydrous MgSO$_4$, filtered and concentrated. Silica gel chromatography (25-33% ethyl acetate in hexanes) afforded [6-fluoro-3-methyl-4-(1-phenylacetyl-piperidin-4-yl)-naphthalen-2-yl]-acetic acid methyl ester (77 mg, 75%). MS cald. for $C_{27}H_{29}FNO_3$ [(M+H)$^+$]: 434, obsd. 434.2.

[6-Fluoro-3-methyl-4-(1-phenylacetyl-piperidin-4-yl)-naphthalen-2-yl]-acetic acid To a solution of [6-fluoro-3-methyl-4-(1-phenylacetyl-piperidin-4-yl)-naphthalen-2-yl]-acetic acid methyl ester (77 mg, 0.178 mmol) in THF (8.0 mL) was added a solution of lithium hydroxide monohydrate (74.7 mg, 1.8 mmol) in water (2 mL). The reaction mixture was stirred at room temperature overnight. After this time, the reaction mixture was concentrated. Water (~20 mL) was added and the mixture was acidified with 1.0 N aqueous HCl (3.1 mL). The resulting white precipitate was collected by vacuum filtration, washed with water and hexanes, and then further dried under vacuum to give [6-fluoro-3-methyl-4-(1-phenylacetyl-piperidin-4-yl)-naphthalen-2-yl]-acetic acid (52.5 mg, 70%). $^1$H NMR (400 MHz, DMSO-$d_6$) δ ppm 12.5 (br. s, 1H), 7.88 (dd, J=9.00, 6.50 Hz, 1H), 7.66 (s, 1H), 7.46-7.61 (m, 1H), 7.27-7.43 (m, 5H), 7.18-7.26 (m, 1H), 4.48-4.74 (m, 1H), 4.00-4.20 (m, 1H), 3.57-3.99 (m, 6H), 2.65-2.97 (m, 1H), 2.11-2.46 (m, 3H), 1.70-2.10 (m, 1H), 1.42-1.69 (m, 2H). MS cald. for $C_{26}H_{27}FNO_3$ [(M+H)$^+$]: 420, obsd. 420.2.

Example 32

{4-[1-(2,6-Difluoro-phenylcarbamoyl)-piperidin-4-yl]-6-fluoro-3-methyl-naphthalen-2-yl}-acetic acid

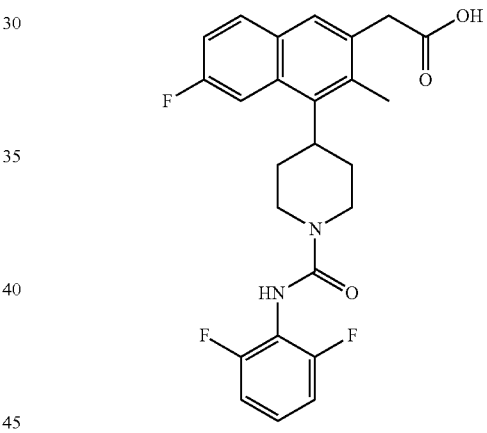

{4-[1-(2,6-Difluoro-phenylcarbamoyl)-piperidin-4-yl]-6-fluoro-3-methyl-naphthalen-2-yl}-acetic acid methyl ester To a solution of (6-fluoro-3-methyl-4-piperidin-4-yl-naphthalen-2-yl)-acetic acid methyl ester (which may be prepared as described above; 75.5 mg, 0.239 mmol) in methylene chloride (8.0 mL) was added neat 2,6-difluorophenyl isocyanate (74.1 mg, 0.478 mmol) at room temperature under nitrogen. The resulting light brown solution was stirred overnight. The reaction mixture was diluted with water (~20 mL) and the resulting mixture was extracted with methylene chloride (2×30 mL). The combined organic layers were washed with saturated aqueous NaHCO$_3$, dried over anhydrous Na$_2$SO$_4$, filtered, then concentrated to a yellowish film. Silica gel chromatography (33% ethyl acetate in hexanes) provided {4-[1-(2,6-difluoro-phenylcarbamoyl)-piperidin-4-yl]-6-fluoro-3-methyl-naphthalen-2-yl}-acetic acid methyl ester (95.4 mg, 85%) as a colorless film. MS cald. for $C_{26}H_{26}F_3N_2O_3$ [(M+H)$^+$]: 471, obsd. 471.2.

{4-[1-(2,6-Difluoro-phenylcarbamoyl)-piperidin-4-yl]-6-fluoro-3-methyl-naphthalen-2-yl}-acetic acid To a solution of {4-[1-(2,6-difluoro-phenylcarbamoyl)-piperidin-4-yl]-6-fluoro-3-methyl-naphthalen-2-yl}-acetic acid methyl ester (95.4 mg, 0.203 mmol) in THF (8.0 mL) was added a solution of lithium hydroxide monohydrate (97.2 mg, 2.3 mmol) in water (2.0 mL) at room temperature. The resulting solution was stirred overnight at room temperature under a nitrogen atmosphere. Then, the solvent was removed and the residue was combined with water (25 mL). The mixture was neutralized with 1.0 N HCl. The resulting white precipitate was collected by filtration and dried under high vacuum to provide {4-[1-(2,6-difluoro-phenyl-carbamoyl)-piperidin-4-yl]-6-fluoro-3-methyl-naphthalen-2-yl}-acetic acid (59.2 mg, 64%) as a white solid. $^1$H NMR (400 MHz, DMSO-$d_6$) δ ppm 12.46 (br. s, 1H), 8.38 (br. s, 1H), 7.90 (dd, J=9.00, 6.40 Hz, 1H), 7.75-7.85 (m, 1H), 7.65-7.74 (m, 1H), 7.24-7.42 (m, 2H), 7.14 (m, 2H), 4.17-4.38 (m, 2H), 3.79 (m, 3H), 2.99-3.24 (m, 2H), 2.44 (s, 3H), 2.13-2.36 (m, 1H), 1.57-1.73 (m, 2H). MS cald. for $C_{25}H_{24}F_3N_2O_3$ [(M+H)$^+$]: 457, obsd. 457.2.

Example 33

{4-[1-(2,4-Dichloro-phenylcarbamoyl)-piperidin-4-yl]-6-fluoro-3-methyl-naphthalen-2-yl}-acetic acid

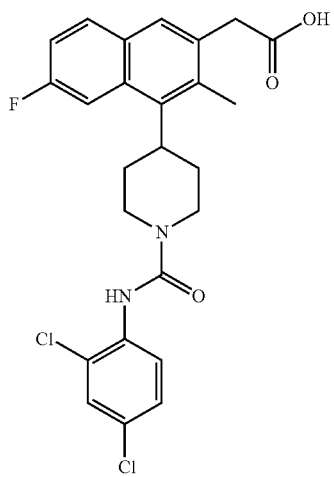 [SMILES: Cc1c(CC(=O)O)cc2ccc(F)cc2c1C1CCN(C(=O)Nc2ccc(Cl)cc2Cl)CC1]

{4-[1-(2,4-Dichloro-phenylcarbamoyl)-piperidin-4-yl]-6-fluoro-3-methyl-naphthalen-2-yl}-acetic acid methyl ester To a solution of (6-fluoro-3-methyl-4-piperidin-4-yl-naphthalen-2-yl)-acetic acid methyl ester (which may be prepared as described above; 47.2 mg, 0.150 mmol) in methanol (6.0 mL) was added neat 2,4-dichlorophenyl isocyanate (56.4 mg, 0.300 mmol) at room temperature under nitrogen. The resulting light brown solution was stirred at room temperature for 15 minutes. The reaction mixture was diluted with water (~25 mL) and the resulting mixture was extracted with ethyl acetate (2×30 mL). The combined organic layers were washed with saturated aqueous NaHCO$_3$, dried over anhydrous Na$_2$SO$_4$, filtered and concentrated to a colorless film. Silica gel chromatography (20-25% ethyl acetate in hexanes) provided {4-[1-(2,4-dichloro-phenylcarbamoyl)-piperidin-4-yl]-6-fluoro-3-methyl-naphthalen-2-yl}-acetic acid methyl ester (74.8 mg, 99%) as a colorless film. MS cald. for $C_{26}H_{26}Cl_2FN_2O_3$ [(M+H)$^+$]: 503, obsd. 503.1.

{4-[1-(2,4-Dichloro-phenylcarbamoyl)-piperidin-4-yl]-6-fluoro-3-methyl-naphthalen-2-yl}-acetic acid To a solution of {4-[1-(2,4-dichloro-phenylcarbamoyl)-piperidin-4-yl]-6-fluoro-3-methyl-naphthalen-2-yl}-acetic acid methyl ester (74.8 mg, 0.149 mmol) in THF (8.0 mL) was added a solution of lithium hydroxide monohydrate (71.4 mg, 1.7 mmol) in water (2.0 mL) at room temperature. The resulting solution was stirred overnight at room temperature under a nitrogen atmosphere. The solvent was evaporated. Water (~20 mL) was added and the mixture was neutralized with 1.0 N HCl (30 mL). The resulting white precipitate was collected by filtration and dried under high vacuum overnight to provide {4-[1-(2,4-dichloro-phenylcarbamoyl)-piperidin-4-yl]-6-fluoro-3-methyl-naphthalen-2-yl}-acetic acid (57.8 mg, 80%) as a white solid. $^1$H NMR (400 MHz, DMSO-$d_6$) δ ppm 12.5 (br. s, 1H), 8.46 (br. s, 1H), 7.90 (dd, J=8.80, 6.50 Hz, 1H), 7.76-7.86 (m, 1H), 7.68 (m, 2H), 7.50 (d, J=8.78 Hz, 1H), 7.40 (dd, J=8.70, 2.30 Hz, 1H), 7.30-7.37 (m, 1H), 4.20-4.32 (m, 2H), 3.68-3.97 (m, 4H), 3.02-3.24 (m, 2H), 2.43 (s, 3H), 2.16-2.40 (m, 2H), 1.61-1.70 (m, 2H). MS cald. for $C_{25}H_{24}Cl_2FN_2O_3$ [(M+H)$^+$]: 489, obsd. 489.1.

Example 34

{4-[1-(2-Chloro-phenylcarbamoyl)-piperidin-4-yl]-6-fluoro-3-methyl-naphthalen-2-yl}-acetic acid

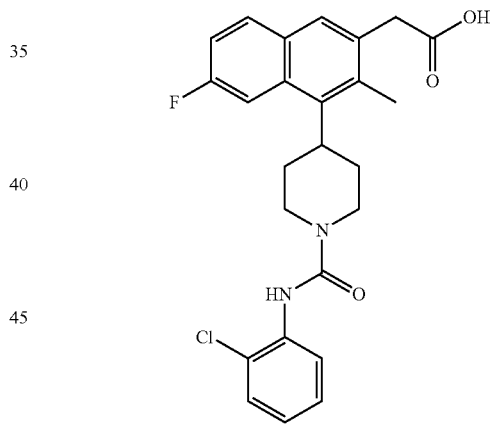

{4-[1-(2-Chloro-phenylcarbamoyl)-piperidin-4-yl]-6-fluoro-3-methyl-naphthalen-2-yl}-acetic acid methyl ester A solution of (6-fluoro-3-methyl-4-piperidin-4-yl-naphthalen-2-yl)-acetic acid methyl ester (which may be prepared as described above; 153 mg, 0.485 mmol) in methanol (6.0 mL) was added to neat 1-chloro-2-isocyanatobenzene (81.9 mg, 0.534 mmol) at room temperature under nitrogen. The resulting light brown solution was heated at reflux for 15 hours at which time LCMS analysis indicated the presence of significant starting material. Reflux was continued over the weekend. LCMS analysis indicated little change in the reaction progress. To the reaction mixture was added N,N-diisopropylethylamine (93.2 μL, 0.534 mmol) at room temperature and the reaction mixture was then refluxed again for 24 hours. Significant starting material still remained. The reaction mixture was diluted with water (25 mL) and resulting mixture was extracted with ethyl acetate (2×50 mL). The combined extracts were washed with brine, dried over anhydrous MgSO$_4$, filtered, and concentrated to give the crude product as a semi-solid (230 mg). Flash chromatography (40 g ISCO column, eluting with 0-100% ethyl acetate/hexanes and finally 25% MeOH/dichloromethane) provided {4-[1-(2-chloro-phenylcarbamoyl)-piperidin-4-yl]-6-fluoro-3-methyl-naphthalen-2-yl}-acetic acid methyl ester (10.5 mg, 4.6%) as a viscous oil. MS cald. for $C_{26}H_{27}ClFN_2O_3$ [(M+H)$^+$] 469, obsd. 469.0.

{4-[1-(2-Chloro-phenylcarbamoyl)-piperidin-4-yl]-6-fluoro-3-methyl-naphthalen-2-yl}-acetic acid To a solution of {4-[1-(2-chloro-phenylcarbamoyl)-piperidin-4-yl]-6-fluoro-3-methyl-naphthalen-2-yl}-acetic acid methyl ester (10 mg, 0.021 mmol) in THF (2.0 mL) was added a solution of lithium hydroxide monohydrate (10.2 mg, 0.426 mmol) in water (0.5 mL) at room temperature. The resulting solution was stirred for 15 hours at room temperature under nitrogen atmosphere. The solvent was removed and the aqueous layer was neutralized with 1.0N HCl. The resulting white solids were collected by filtration, washed with water and hexanes, and dried in the air to give {4-[1-(2-chloro-phenylcarbamoyl)-piperidin-4-yl]-6-fluoro-3-methyl-naphthalen-2-yl}-acetic acid (4.5 mg, 46%) as a white solid. $^1$H NMR (400 MHz, DMSO-d$_6$) δ ppm 12.42 (br. s, 1H), 7.9 (dd, J=8.91, 6.65 Hz, 1H), 7.69 (s, 1H), 7.48 (d, J=8.03 Hz, 2H), 7.25-7.42 (m, 3H), 7.09-7.23 (m, 1H), 4.27 (d, J=10.79 Hz, 2H), 3.79 (br. s, 4H), 2.43 (s, 4H), 1.65 (d, J=12.05 Hz, 3H), 1.23 (s, 2H). MS cald. for $C_{25}H_{25}ClFN_2O_3$ [(M+H)$^+$] 455, obsd. 455.0.

Example 35

{6-Fluoro-4-[1-(2-methoxy-phenylcarbamoyl)-piperidin-4-yl]-3-methyl-naphthalen-2-yl}-acetic acid

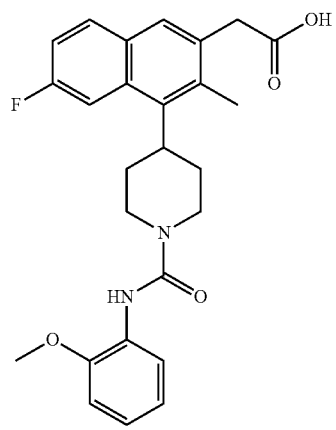 [SMILES: COc1ccccc1NC(=O)N1CCC(c2c(C)c(CC(=O)O)cc3ccc(F)cc23)CC1]

{6-Fluoro-4-[1-(2-methoxy-phenylcarbamoyl)-piperidin-4-yl]-3-methyl-naphthalen-2-yl}-acetic acid methyl ester To a solution of (6-fluoro-3-methyl-4-piperidin-4-yl-naphthalen-2-yl)-acetic acid methyl ester (which may be prepared as described above; 83.6 mg, 0.265 mmol) in methylene chloride (8.0 mL) was added 2-methoxyphenyl isocyanate (71 µL, 0.53 mmol) at room temperature under nitrogen. The resulting light brown solution was stirred at room temperature for 10 minutes. The reaction mixture was diluted with water (~25 mL) and the resulting mixture was extracted with methylene chloride (2×30 mL). The combined organic layers were washed with saturated aqueous NaHCO$_3$, dried over anhydrous Na$_2$SO$_4$, filtered and concentrated to a light yellow film. Flash chromatography (0-60% ethyl acetate in hexanes) provided {6-fluoro-4-[1-(2-methoxy-phenylcarbamoyl)-piperidin-4-yl]-3-methyl-naphthalen-2-yl}-acetic acid methyl ester (107.6 mg, 87%) as a colorless film. MS cald. for $C_{27}H_{30}FN_2O_4$ [(M+H)$^+$]: 465, obsd. 465.3.

{6-Fluoro-4-[1-(2-methoxy-phenylcarbamoyl)-piperidin-4-yl]-3-methyl-naphthalen-2-yl}-acetic acid methyl ester To a solution of {6-fluoro-4-[1-(2-methoxy-phenylcarbamoyl)-piperidin-4-yl]-3-methyl-naphthalen-2-yl}-acetic acid methyl ester (107.6 mg, 0.232 mmol) in THF (8.0 mL) was added a solution of lithium hydroxide monohydrate (111.1 mg, 2.6 mmol) in water (2.0 mL) at room temperature. The resulting solution was stirred overnight at room temperature under a nitrogen atmosphere. The solvent was evaporated. Water (~25 mL) was added and the mixture was acidified with 1.0 N aqueous HCl (4.6 mL). The resulting white precipitate was collected by filtration and dried under high vacuum to provide {6-fluoro-4-[1-(2-methoxy-phenylcarbamoyl)-piperidin-4-yl]-3-methyl-naphthalen-2-yl}-acetic acid (86.4 mg, 83%) as a white powder. $^1$H NMR (300 MHz, DMSO-d$_6$) δ ppm 12.45 (b. s, 1H), 7.90 (dd, J=9.23, 6.59 Hz, 1H), 7.78 (br. s., 1H), 7.65-7.72 (m, 2H), 7.35 (t, J=8.01 Hz, 1H), 6.99-7.06 (m, 2H), 6.86-6.95 (m, 1H), 4.23 (m, 2H), 3.82 (s, 3H), 3.78 (br. s., 2H), 3.32 (br. s., 3H), 3.09 (br. s., 2H), 2.43 (s, 3H), 1.66 (m, 2H). MS cald. for $C_{26}H_{28}FN_2O_4$ [(M+H)$^+$]: 451, obsd. 451.2.

Example 36

{6-Fluoro-3-methyl-4-[1-(3-trifluoromethyl-phenyl-carbamoyl)-piperidin-4-yl-naphthalen-2-yl}-acetic acid

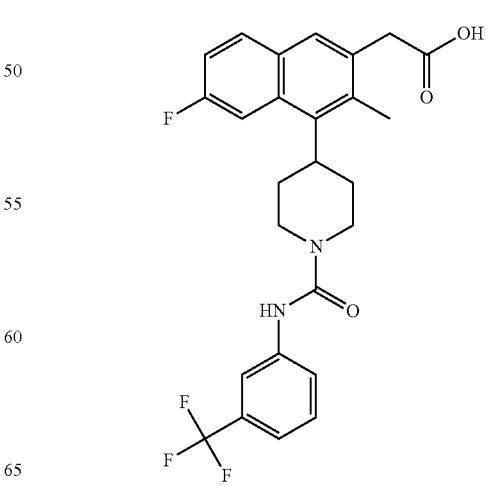

{6-Fluoro-3-methyl-4-[1-(3-trifluoromethyl-phenyl-carbamoyl)-piperidin-4-yl-naphthalen-2-yl}-acetic acid methyl ester To a solution of (6-fluoro-3-methyl-4-piperidin-4-yl-naphthalen-2-yl)-acetic acid methyl ester (which may be prepared as described above; 94 mg, 0.298 mmol) in methylene chloride (6.0 mL) was added trifluoro-m-tolyl isocyanate (82 µL, 0.596 mmol) at room temperature under nitrogen. The resulting light brown solution was stirred at room temperature for 40 minutes. The reaction mixture was diluted with water (~25 mL) and the resulting mixture was extracted with methylene chloride (3×25 mL). The combined organic layers were washed with saturated aqueous $NaHCO_3$, dried over anhydrous $Na_2SO_4$, filtered and concentrated to a yellow-orange film. Silica gel chromatography (20-25% ethyl acetate in hexanes) provided {6-fluoro-3-methyl-4-[1-(3-trifluoromethyl-phenylcarbamoyl)-piperidin-4-yl]-naphthalen-2-yl}-acetic acid methyl ester (97 mg, 65%) as a colorless film. MS cald. for $C_{27}H_{27}F_4N_2O_3$ $[(M+H)^+]$: 503, obsd. 503.2.

{6-Fluoro-4-[1-(2-methoxy-phenylcarbamoyl)-piperidin-4-yl]-3-methyl-naphthalen-2-yl}-acetic acid methyl ester To a solution of {6-fluoro-3-methyl-4-[1-(3-trifluoromethyl-phenylcarbamoyl)-piperidin-4-yl]-naphthalen-2-yl}-acetic acid methyl ester (97 mg, 0.193 mmol) in THF (8.0 mL) was added a solution of lithium hydroxide monohydrate (92.4 mg, 2.2 mmol) in water (2.0 mL) at room temperature. The resulting solution was stirred for four hours under a nitrogen atmosphere. The solvent was evaporated. Water (~25 mL) was added and the mixture was acidified with 1.0 N aqueous HCl (3.9 mL). The resulting white precipitate was collected by filtration, washed with water and hexanes, and dried under high vacuum to provide {6-fluoro-3-methyl-4-[1-(3-trifluoromethyl-phenylcarbamoyl)-piperidin-4-yl]-naphthalen-2-yl}-acetic acid (65.8 mg, 70%). $^1H$ NMR (400 MHz, DMSO-$d_6$) δ ppm 12.50 (br. s, 1H), 8.97 (br. s, 1H), 8.00-8.22 (m, 1H), 7.97 (s, 1H), 7.90 (dd, J=9.10, 6.50 Hz, 1H), 7.78 (d, J=8.50 Hz, 1H), 7.66-7.73 (m, 1H), 7.49 (t, J=8.30 Hz, 1H), 7.30-7.38 (m, 1H), 7.28 (d, J=8.30 Hz, 1H), 4.28-4.36 (m, 2H), 3.71-3.85 (m, 3H), 3.01-3.18 (m, 2H), 2.43 (s, 3H), 2.17-2.34 (m, 1H), 1.64-1.73 (m, 2H). MS cald. for $C_{26}H_{25}F_4N_2O_3$ $[(M+H)^+]$: 489, obsd. 489.2.

Example 37

Activity and Use of the Compounds

The compounds of formula I possess valuable pharmacological properties. It has been found that said compounds are antagonists at the CRTH2 receptor and may be useful in treating diseases and disorders associated with that receptor such as asthma. The activity of the present compounds as CRTH2 receptor antagonists is demonstrated by the following biological assays.
Calcium Flux Assay Using Fluorometric Imaging Plate Reader (FLIPR)
Cell Culture Conditions:
CHO-K1 cells previously transfected with G-alpha 16 were subsequently transfected with the human CRTH2 receptor and the neomycin resistance gene. Following selection in 800 µg/mL G418 (geneticin), individual clones were assayed for their receptor expression based on staining with an anti human CRTH2 IgG, followed by assaying for their response to 13,14-dihydro-15-keto Prostaglandin $D_2$ (DK-$PDG_2$) (ligand) in the $Ca^{2+}$ Flux assay. Positive clones were then cloned by limiting dilution cloning. The transfected cells were cultured in Ham's F-12 medium supplemented with 10% fetal bovine serum, 2 mM glutamine, 100 U/mL penicillin/100 µg/mL streptomycin, 200 µg/mL hygromycin B, and 800 µg/mL G418 (geneticin). Cells were harvested with trypsin-EDTA (trypsin-ethylenediaminetetraacetic acid) and counted using ViaCount® reagent (from Guava Technologies, Inc. which contains two DNA-binding dyes that enable the reagent user to distinguish between viable and non-viable cells). The cell suspension volume was adjusted to $2.5 \times 10^5$ cells/mL with complete growth media. Aliquots of 50 µL were dispensed into BD Falcon™ 384 well black/clear microplates (from BD Biosciences, a division of Becton, Dickinson and Company) and the microplates were placed in a 37° C. $CO_2$ incubator overnight. The following day, the microplates were used in the assay.
Dye Loading and Assay:
Loading Buffer containing dye (from the FLIPR® Calcium 3 Assay Kit from Molecular Devices, a division of MDS Analytical Technologies and MDS Inc.) was prepared by dissolving the contents of one bottle into 200 mL Hank's Balanced Salt Solution containing 20 mM HEPES (4-(2-hydroxyethyl)-1-piperazineethanesulfonic acid) and 2.5 mM probenecid. Growth media was removed from the cell plates and 25 µL of Hank's Balanced Salt Solution (HBSS) containing 20 mM HEPES, 0.05% BSA and 2.5 mM probenecid was added to each well followed by 25 µL of diluted dye using a Multidrop dispenser. The plates were then incubated for 1 hour at 37° C.

During the incubation, test compound plates were prepared by adding 90 µL of HBSS/20 mM HEPES/0.005% BSA buffer to the 2 µL of serial diluted compounds. To prepare serial diluted compounds, 20 mM stocks of compounds were dissolved in 100% DMSO. The compound dilution plate was set up as follows: well #1 received 5 µL of compound plus 10 µL of DMSO. Wells 2-10 received 10 µL of DMSO. 5 µL was mixed and transferred from well #1 into well #2. 1:3 serial dilutions were continued out 10 steps. 2 µL of diluted compound was transferred into duplicate wells of a 384 well "assay plate" and then 90 µL of buffer was added.

After incubation, both the cell and "assay plate" plates were brought to the fluorometric imaging plate reader (FLIPR®) and 20 µL of the diluted compounds were transferred to the cell plates by the FLIPR®. Plates were then incubated for 1 hour at room temperature. After the 1 hour incubation, plates were returned to the FLIPR® and 20 µL of 4.5× concentrated ligand was added to the cell plates. During the assay, fluorescence readings were taken simultaneously from all 384 wells of the cell plate every 1.5 seconds. Five readings were taken to establish a stable baseline, then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following agonist addition were determined. The initial fluorescence reading from each well, prior to ligand stimulation, was used as a zero baseline value for the data from that well. The responses were expressed as % inhibition of the buffer control. The $IC_{50}$ value, defined as the concentration of a compound that was required for 50% inhibition of the buffer control, was calculated by fitting the percent inhibition data for 10 concentrations to a sigmoidal dose-response (4 parameter logistic) model using Genedata Screener® Condoseo software program [from Genedata AG, model 205, where $F(x)=(A+(B-A)/(1+((C/x)^D)))$].

Activity data for example compounds tested in the above described FLIPR assay are shown in Table 1 below:

TABLE 1

| Example No. | FLIPR Assay IC$_{50}$ (μM) |
|---|---|
| 1 | 0.018 |
| 2 | 0.053 |
| 3 | 0.104 |
| 4 | 1.74 |
| 5 | 0.898 |
| 6 | 0.0025 |
| 7 | 0.095 |
| 8 | 0.042 |
| 9 | 1.15 |
| 10 | 0.0035 |
| 11 | 0.0048 |
| 12 | 0.404 |
| 13 | 1.35 |

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4$^+$ cell purification using a CD4$^+$ T Cell Isolation Kit II (from Miltenyi Biotec Inc.). The CD4$^+$ T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to Alexa Fluor 647.

To determine cellular inhibitory potency, compounds at various concentrations were incubated with 2.5×10$^4$ Th2 cells and 500 nM DK-PGD$_2$ for 4 hrs at 37° C. in 200 μL of X-VIVO 15® medium containing 10° A human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and IC$_{50}$ calculations.

The percent inhibition of interleukin 13 (IL-13) production for a compound at various concentrations was calculated according to the following formula, [1-(IL-13 production in the presence of compound)/(IL-13 production in the presence of 0.15% DMSO)]×100. The IC$_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where F(x)=(A+(B−A)/(1+((C/x)^D)))].

Activity data for example compounds tested in the above described DK-PGD$_2$-induced IL-13 production assay are shown in Table 2 below:

TABLE 2

| Example No. | TH2 IL-13 IC$_{50}$ (μM) |
|---|---|
| 14 | 0.033 |
| 15 | 0.142 |
| 16 | 0.022 |
| 17 | 0.12 |
| 18 | 0.058 |
| 19 | 0.008 |
| 20 | 0.009 |
| 21 | 0.045 |
| 22 | 0.023 |
| 23 | 0.266 |
| 24 | 0.023 |
| 25 | 0.014 |
| 26 | 0.032 |
| 27 | 0.027 |
| 28 | 0.060 |
| 29 | 0.020 |
| 30 | 0.083 |
| 31 | 0.117 |
| 32 | 0.371 |
| 33 | 0.030 |
| 34 | 0.059 |
| 35 | 0.241 |
| 36 | 0.437 |

It is to be understood that the invention is not limited to the particular embodiments of the invention described above, as variations of the particular embodiments may be made and still fall within the scope of the appended claims.

The invention claimed is:

1. A compound of formula (I):

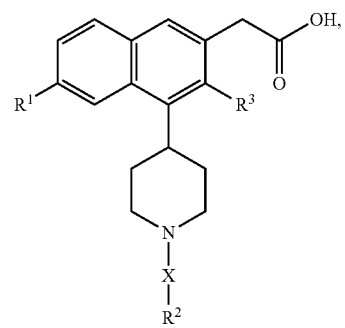

wherein:

X is —SO$_2$— or —C(O)—;

R$^1$ is halogen;

R$^2$ is phenyl, unsubstituted or mono- or bi-substituted independently with lower alkyl, halogen, alkoxy, —SO$_2$-lower alkyl or haloalkyl, unsubstituted heteroaryl, lower alkyl, unsubstituted or substituted with unsubstituted phenyl or phenyl substituted with halogen, NO$_2$ or NH$_2$, unsubstituted cycloalkyl, unsubstituted heterocycloalkyl, or NH-phenyl, said phenyl being unsubstituted or substituted with halogen, lower alkyl, haloalkyl, —SO$_2$-lower alkyl or alkoxy; and R³ is lower alkyl or hydrogen,
or a pharmaceutically acceptable salt thereof.

2. The compound according to claim 1, wherein X is —SO₂—.

3. The compound according to claim 1, wherein X is —C(O)—.

4. The compound according to claim 1, wherein R¹ is fluorine.

5. The compound according to claim 1, wherein X is —SO₂— and R² is phenyl, unsubstituted or mono- or bi-substituted independently with lower alkyl, halogen, alkoxy, —SO₂-lower alkyl or —CF₃; unsubstituted heteroaryl; or lower alkyl, unsubstituted or substituted with unsubstituted phenyl or phenyl substituted with halogen, NO₂ or NH₂.

6. The compound according to claim 1, wherein X is —SO₂— and R² is unsubstituted cycloalkyl; unsubstituted heterocycloalkyl; or NH-phenyl, said phenyl being unsubstituted or substituted with halogen, lower alkyl, haloalkyl, —SO₂-lower alkyl or alkoxy.

7. The compound according to claim 1, wherein R² is phenyl, methylphenyl, chlorophenyl, methanesulfonylphenyl, dichlorophenyl, difluorophenyl, trifluoromethylphenyl, bis-trifluoromethylphenyl, methoxyphenyl, nitrophenyl or aminophenyl.

8. The compound according to claim 1, wherein R² is pyridinyl.

9. The compound according to claim 1, wherein R² is methyl or methyl substituted with phenyl, chlorophenyl, nitrophenyl or aminophenyl.

10. The compound according to claim 1, wherein R² is cyclopentyl.

11. The compound according to claim 1, wherein R² is pyrrolidinyl.

12. The compound according to claim 1, wherein R² is —NH-difluorophenyl, —NH-dichlorophenyl, —NH-chlorophenyl, —NH-phenylmethoxy or —NH-trifluoromethylphenyl.

13. The compound according to claim 1, wherein R³ is methyl.

14. The compound according to claim 1, wherein R³ is hydrogen.

15. The compound according to claim 1, wherein said compound is:
[4-(1-Benzenesulfonyl-piperidin-4-yl)-6-fluoro-naphthalen-2-yl]-acetic acid;
{6-Fluoro-4-[1-(toluene-4-sulfonyl)-piperidin-4-yl]-naphthalen-2-yl}-acetic acid;
{6-Fluoro-4-[1-(pyridine-2-sulfonyl)-piperidin-4-yl]-naphthalen-2-yl}-acetic acid;
{6-Fluoro-4-[1-(pyridine-3-sulfonyl)-piperidin-4-yl]-naphthalen-2-yl}-acetic acid;
{6-Fluoro-4-[1-(pyridine-4-sulfonyl)-piperidin-4-yl]-naphthalen-2-yl}-acetic acid;
{4-[1-(2-Chloro-benzenesulfonyl)-piperidin-4-yl]-6-fluoro-naphthalen-2-yl}-acetic acid;
{4-[1-(3-Chloro-benzenesulfonyl)-piperidin-4-yl]-6-fluoro-naphthalen-2-yl}-acetic acid;
{4-[1-(4-Chloro-benzenesulfonyl)-piperidin-4-yl]-6-fluoro-naphthalen-2-yl}-acetic acid;
{6-Fluoro-4-[1-(3-methanesulfonyl-benzenesulfonyl)-piperidin-4-yl]-naphthalen-2-yl}-acetic acid;
{4-[1-(2,5-Dichloro-benzenesulfonyl)-piperidin-4-yl]-6-fluoro-naphthalen-2-yl}-acetic acid;
{4-[1-(2,4-Dichloro-benzenesulfonyl)-piperidin-4-yl]-6-fluoro-naphthalen-2-yl}-acetic acid;
{4-[1-(3,5-Dichloro-benzenesulfonyl)-piperidin-4-yl]-6-fluoro-naphthalen-2-yl}-acetic acid;
{4-[1-(3,5-Bis-trifluoromethyl-benzenesulfonyl)-piperidin-4-yl]-6-fluoro-naphthalen-2-yl}-acetic acid;
{4-[1-(2-Chloro-benzenesulfonyl)-piperidin-4-yl]-6-fluoro-3-methyl-naphthalen-2-yl}-acetic acid;
[6-Fluoro-4-(1-methanesulfonyl-piperidin-4-yl)-3-methyl-naphthalen-2-yl]-acetic acid;
{4-[1-(2,4-Dichloro-benzenesulfonyl)-piperidin-4-yl]-6-fluoro-3-methyl-naphthalen-2-yl}-acetic acid;
{4-[1-(2,5-Dichloro-benzenesulfonyl)-piperidin-4-yl]-6-fluoro-3-methyl-naphthalen-2-yl}-acetic acid;
{4-[1-(2,6-Dichloro-benzenesulfonyl)-piperidin-4-yl]-6-fluoro-3-methyl-naphthalen-2-yl}-acetic acid;
[6-Fluoro-3-methyl-4-(1-phenylmethanesulfonyl-piperidin-4-yl)-naphthalen-2-yl]-acetic acid;
{6-Fluoro-4-[1-(2-methoxy-benzenesulfonyl)-piperidin-4-yl]-3-methyl-naphthalen-2-yl}-acetic acid;
{4-[1-(3-Chloro-phenylmethanesulfonyl)-piperidin-4-yl]-6-fluoro-3-methyl-naphthalen-2-yl}-acetic acid;
{4-[1-(4-Chloro-phenylmethanesulfonyl)-piperidin-4-yl]-6-fluoro-3-methyl-naphthalen-2-yl}-acetic acid;
{6-Fluoro-3-methyl-4-[1-(3-trifluoromethyl-benzenesulfonyl)-piperidin-4-yl]-naphthalen-2-yl}-acetic acid;
[4-(1-Cyclopentanesulfonyl-piperidin-4-yl)-6-fluoro-3-methyl-naphthalen-2-yl]-acetic acid;
{6-Fluoro-3-methyl-4-[1-(pyrrolidine-1-sulfonyl)-piperidin-4-yl]-naphthalen-2-yl}-acetic acid;
{6-Fluoro-3-methyl-4-[1-(2-nitro-phenylmethanesulfonyl)-piperidin-4-yl]-naphthalen-2-yl}-acetic acid;
{4-[1-(2-Amino-phenylmethanesulfonyl)-piperidin-4-yl]-6-fluoro-3-methyl-naphthalen-2-yl}-acetic acid;
{4-[1-(2,4-Dichloro-benzoyl)-piperidin-4-yl]-6-fluoro-3-methyl-naphthalen-2-yl}-acetic acid;
{4-[1-(2,6-Dichloro-benzoyl)-piperidin-4-yl]-6-fluoro-3-methyl-naphthalen-2-yl}-acetic acid;
{4-[1-(2,5-Difluoro-benzoyl)-piperidin-4-yl]-6-fluoro-3-methyl-naphthalen-2-yl}-acetic acid;
[6-Fluoro-3-methyl-4-(1-phenylacetyl-piperidin-4-yl)-naphthalen-2-yl]-acetic acid;
{4-[1-(2,6-Difluoro-phenylcarbamoyl)-piperidin-4-yl]-6-fluoro-3-methyl-naphthalen-2-yl}-acetic acid;
{4-[1-(2,4-Dichloro-phenylcarbamoyl)-piperidin-4-yl]-6-fluoro-3-methyl-naphthalen-2-yl}-acetic acid;
{4-[1-(2-Chloro-phenylcarbamoyl)-piperidin-4-yl]-6-fluoro-3-methyl-naphthalen-2-yl}-acetic acid;
{6-Fluoro-4-[1-(2-methoxy-phenylcarbamoyl)-piperidin-4-yl]-3-methyl-naphthalen-2-yl}-acetic acid; or
{6-Fluoro-3-methyl-4-[1-(3-trifluoromethyl-phenylcarbamoyl)-piperidin-4-yl-naphthalen-2-yl}-acetic acid.

16. A pharmaceutical composition, comprising a therapeutically effective amount of a compound according to claim 1 and a pharmaceutically acceptable carrier.

17. A method for treating a respiratory disorder selected from chronic obstructive pulmonary disorder (COPD), asthma, and bronchospasm, comprising the step of administering a therapeutically effective amount of a compound according to claim 1 to a subject in need thereof.

* * * * *